| United States Patent [19] | [11] | 4,134,974 |
|---|---|---|
| Melloni et al. | [45] | Jan. 16, 1979 |

[54] IMIDAZO[5,1-c][1,4]BENZOXAZIN-1-ONE

[75] Inventors: Piero Melloni, Bresso, Milan; Nicola Mongelli, Milan; Francesco Lauria, Milan; Alessandro Rossi, Milan; Raffaele Tommasini, Milan, all of Italy

[73] Assignee: Carlo Erba S. p. A., Milan, Italy

[21] Appl. No.: 749,031

[22] Filed: Dec. 8, 1976

[30] Foreign Application Priority Data

Dec. 30, 1975 [IT] Italy ............................. 30829 A/75

[51] Int. Cl.² ................. C07D 498/14; A61K 31/535
[52] U.S. Cl. ............................ 424/248.54; 424/248.5; 424/248.55; 424/248.56; 544/101; 544/34; 544/52; 544/105

[58] Field of Search ...................... 424/248.54, 248.56, 424/248.57, 248.5, 248.55; 544/101

[56] References Cited

U.S. PATENT DOCUMENTS

| 3,929,783 | 12/1974 | Krapcho | 544/101 |
|---|---|---|---|
| 4,035,495 | 7/1977 | Jirkovsky et al. | 544/101 |

*Primary Examiner*—John M. Ford
*Attorney, Agent, or Firm*—Murray & Whisenhunt

[57] ABSTRACT

Cyclic derivatives of 1,4-benzoxazine and 1,4-benzothiazine are disclosd, such as, for instance, 1H,2,3,3a,4-tetrahydro-2-carbamoylmethyl-imidazo[5,1-c][1,4]benzoxazin-1-one and 1H,2,3,3a,4-tetrahydro-2-carbamoylmethyl-8-chloro-imidazo[5,1-c][1,4]benzoxazin-1-one. These compounds are active on the central nervous system, and function as antidepressant agents.

65 Claims, No Drawings

IMIDAZO[5,1-c][1,4]BENZOXAZIN-1-ONE

The present invention relates to cyclic derivatives of 1,4-benzoxazine and 1,4-benzothiazine, to a process for their preparation and to pharmaceutical compositions containing them. The compounds of the invention have the following formula (I)

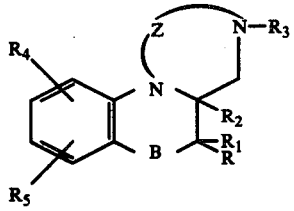

(I)

wherein

B is an oxygen or sulphur atom;

R and $R_1$ are independently selected from the group consisting of hydrogen, $C_1$-$C_6$ alkyl and

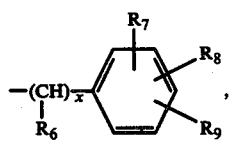

wherein $x$ is zero or an integer of 1 to 6, $R_6$ is hydrogen or $C_1$-$C_6$ alkyl and $R_7$, $R_8$ and $R_9$ are independently selected from the group consisting of hydrogen, halogen, $C_1$-$C_6$ alkyl, $C_1$-$C_6$ trihaloalkyl, hydroxy, carboxy and one of the radicals —$OR_{10}$, —$SO_2R_{10}$ and —$COOR_{10}$, wherein $R_{10}$ is $C_1$—$C_6$ alkyl;

$R_2$ is hydrogen, $C_1$-$C_6$ alkyl or

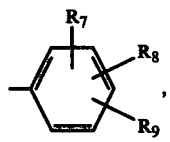

wherein $R_7$, $R_8$ and $R_9$ are as defined above;

$R_3$ is hydrogen; carbamoyl; thiocarbamoyl; $C_1$-$C_6$ alkyl, $C_2$-$C_6$ alkenyl or $C_2$-$C_6$ alkynyl, being each of the alkyl, alkenyl and alkynyl groups unsubstituted or substituted by one or more substituents selected from the group consisting of (a) halogen; (b) carboxy; (c) hydroxy; (d) $C_1$-$C_6$ alkoxy; (e) one of the radicals —$SO_2R_{11}$, —$COOR_{11}$ and —$COR_{11}$, wherein $R_{11}$ is $C_1$—$C_6$ alkyl or

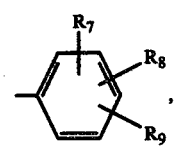

wherein $R_7$, $R_8$ and $R_9$ are as defined above;

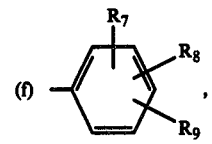

wherein $R_7$, $R_8$ and $R_9$ are as defined above; (g) one of the radicals

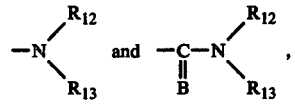

wherein B is as defined above and $R_{12}$ and $R_{13}$ are independently selected from the group consisting of hydrogen and $C_1$-$C_6$ alkyl, or $R_{12}$ and $R_{13}$, taken together with the nitrogen atom, form a pentatomic or hexatomic saturated or unsaturated heteromonocyclic ring, optionally containing another heteroatom selected from the group consisting of N,S and O and optionally substituted by one or more substituents selected from the group consisting of $C_1$-$C_6$ alkyl and

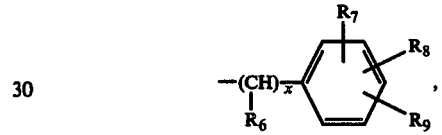

wherein $x$, $R_6$, $R_7$, $R_8$ and $R_9$ are as defined above;

$R_4$ and $R_5$ are independently selected from the group consisting of hydrogen; halogen; amino; acylamino; $C_1$-$C_6$ alkyl; $C_1$-$C_6$ trihaloalkyl; hydroxy; carboxy; $C_1$-$C_6$ alkoxy; $R_{10}$—$SO_2$—NH—, wherein $R_{10}$ is as defined above; one of the radicals —$SO_2R_{11}$ and —$COOR_{11}$, wherein $R_{11}$ is as defined above; or $R_4$ and $R_5$, taken together, form a radical —$CH_2$—O—$CH_2$— or, $R_4$ and $R_5$, taken together with two adjacent carbon atoms of the benzene ring, form a carbocyclic ring;

Z is

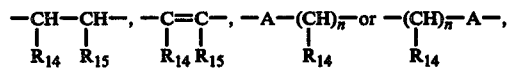

wherein $R_{14}$ and $R_{15}$ are independently selected from the group consisting of hydrogen, $C_1$-$C_6$ alkyl and

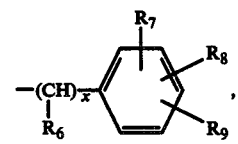

wherein $x$, $R_6$, $R_7$, $R_8$ and $R_9$ are as defined above, $n$ is zero or 1 and A is

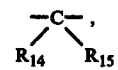

wherein $R_{14}$ and $R_{15}$ are as defined above, or >C=B, wherein B is as defined above; provided that (a) when Z is

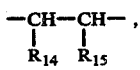

at least one of $R_{14}$ and $R_{15}$ is different from hydrogen;
(b) when A is

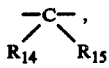

being $n=1$, in the radical

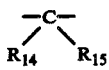

at least one of $R_{14}$ and $R_{15}$ is hydrogen; and (c) when Z is

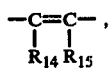

$R_3$ is different from hydrogen.

From the above, it is evident that when A is

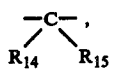

being $n=1$, then Z is

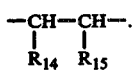

Object of the present invention are also the pharmaceutically acceptable salts of the compounds of formula (I), as well as all the possible stereoisomers and the mixtures thereof. The alkyl, alkenyl, alkynyl and alkoxy groups may be either branched or straight chain groups.

When in the radical

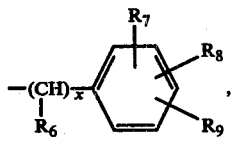

$x$ is different from zero, it is preferably 1 or 2, in particular 1. In the same radical, $R_6$ is preferably hydrogen. A $C_1-C_6$ trihaloalkyl group is preferably a trifluoromethyl group.

When $R_{12}$ and $R_{13}$, taken together with the nitrogen atom, form a heteromonocyclic ring, this ring is preferably selected from the group consisting of piperidyl, pirrolidinyl, piperazinyl, oxazolinyl, thiazolinyl and imidazolinyl.

When $R_4$ and/or $R_5$ are acylamino, the acylamino group is preferably a straight or branched chain aliphatic acylamino group, in particular a $C_1-C_6$ alkanoylamino group.

When $R_4$ and $R_5$, taken together with two adjacent carbon atoms of the benzene ring, form a carbocyclic ring, this ring preferably contains 5 or 6 ring carbon atoms and preferably one or two double bonds.

The pharmaceutically acceptable salts of the compounds of formula (I) are either those with inorganic acids, such as hydrochloric and sulphuric acid, or with organic acids, such as citric, tartaric, maleic, mandelic, fumaric and methanesulfonic acid, or with inorganic bases, such as sodium, potassium, calcium and aluminium hydroxides, or with organic bases, such as organic amines, e.g., lysine, triethylamine, procaine, dibenzylamine, N-benzyl-β-phenethylamine, N,N'-dibenzylethylenediamine, dehydrobietilamine, N-ethylpiperidine and the like. Preferred compounds are those of formula (II)

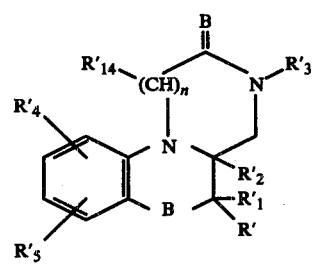

wherein
B and $n$ are as defined above;
$R'$ and $R'_1$ are independently selected from the group consisting of hydrogen, $C_1-C_6$ alkyl and

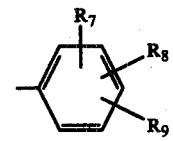

wherein $R_7$, $R_8$ and $R_9$ are as defined above; $R'_2$ is hydrogen, $C_1-C_6$ alkyl or

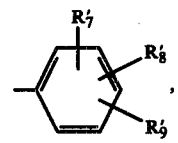

wherein $R'_7$, $R'_8$ and $R'_9$ are independently selected from the group consisting of hydrogen, halogen, $C_1-C_6$ alkyl, trifluoromethyl, hydroxy and $C_1-C_6$ alkoxy; $R'_3$ is hydrogen or $C_1-C_6$ alkyl, unsubstituted or substituted by one or more substituents selected from the group consisting of (a') carboxy; (b') hydroxy; (c') $C_1-C_6$ alkoxy; (d') -COOR$_{10}$, wherein R$_{10}$ is as defined above;

(e') 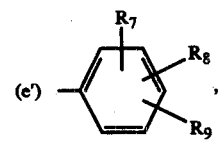

wherein $R_7$, $R_8$ and $R_9$ are as defined above; and (f') one of the radicals 1H,2,3,3a,4-tetrahydro-2-(2'-dimethylaminoethyl)-4-phenyl-imidazo[5,1-c][1,4]benzoxazin-1-one;
1H,2,3,3a,4-tetrahydro-2-(3'-dimethylaminopropyl)-4-phenyl-8-chloro-imidazo[5,1-c][1,4]benzoxazin-1-one;
1H,2,3,3a,4-tetrahydro-2-carbamoylmethyl-4-phenyl-8-chloro-imidazo[5,1-c][1,4]benzoxazin-1-one;
1H,2,3,3a,4-tetrahydro-2-carbamoylmethyl-4-phenyl-8-fluoro-imidazo[5,1-c][1,4]benzoxazin-1-one;
1H,2,3,3a,4-tetrahydro-2-carbamoylmethyl-4-phenyl-8-hydroxy-imidazo[5,1-c][1,4]benzoxazin-1-one;
1H,2,3,3a,4-tetrahydro-2-carbamoylmethyl-4-phenyl-8-amino-imidazo[5,1-c][1,4]benzoxazin-1-one;
1H,2,3,3a,4-tetrahydro-2-carbamoylmethyl-4-phenyl-8-methyl-imidazo[5,1-c][1,4]benzoxazin-1-one;
1H,2,3,3a,4-tetrahydro-2-carbamoylmethyl-4-phenyl-8-trifluoromethyl-imidazo[5,1-c][1,4]benzoxazin-1-one;
1H,2,3,3a,4-tetrahydro-2-carbamoylmethyl-4-phenyl-8-methoxy-imidazo[5,1-c][1,4]benzoxazin-1-one;
1H,2,3,3a,4-tetrahydro-2-carbamoylmethyl-4-phenyl-8-carboxy-imidazo[5,1-c][1,4]benzoxazin-1-one;
1H,2,3,3a,4-tetrahydro-2-carbamoylmethyl-4-phenyl-8-acetamido-imidazo[5,1-c][1,4]benzoxazin-1-one;
1H,2,3,3a,4-tetrahydro-2-carbamoylmethyl-4-phenyl-8-methylsulfonyl-imidazo[5,1-c][1,4]benzoxazin-1-one;
1H,2,3,3a,4-tetrahydro-2-carbamoylmethyl-4-phenyl-8-methylsulfonamido-imidazo[5,1-c][1,4]benzoxazin-1-one;
1H,2,3,3a,4-tetrahydro-2-carbamoylmethyl-4-(2'-methoxyphenyl)-imidazo[5,1-c][1,4]benzoxazin-1-one;
1H,2,3,3a,4-tetrahydro-2-carbamoylmethyl-4-(4'-chlorophenyl)-imidazo[5,1-c][1,4]benzoxazin-1-one;
1H,2,3,3a,4-tetrahydro-2-methyl-3a-phenyl-imidazo[5,1-c][1,4]benzoxazin-1-one;
1H,2,3,3a,4-tetrahydro-2-(2'-carbamoyl-ethyl)-3a-phenyl-imidazo[5,1-c][1,4]benzoxazin-1-one;
1H,2,3,3a,4-tetrahydro-2-(1'-carbamoyl-ethyl)-3a-phenyl-imidazo[5,1-c][1,4-benzoxazin-1-one;
1H,2,3,3a,4-tetrahydro-2-(1'-methyl-1'-carbamoyl-ethyl)-3a-phenyl-imidazo[5,1-c][1,4]benzoxazin-1-one;
1H,2,3,3a,4-tetrahydro-2-(2'-dimethylaminoethyl)-3a-phenyl-imidazo[5,1-c][1,4]benzoxazin-1-one;
1H,2,3,3a,4-tetrahydro-2-(3'-dimethylaminopropyl)-3a-phenyl-imidazo[5,1-c][1,4]benzoxazin-1-one;
1H,2,3,3a,4-tetrahydro-2-carbamoylmethyl-3a-phenyl-8-chloro-imidazo[5,1-c][1,4]benzoxazin-1-one;
1H,2,3,3a,4-tetrahydro-2-carbamoylmethyl-3a-phenyl-8-fluoro-imidazo[5,1-c][1,4]benzoxazin-1-one;
1H,2,3,3a,4-tetrahydro-2-carbamoylmethyl-3a-phenyl-8-hydroxy-imidazo[5,1-c][1,4]benzoxazin-1-one;
1H,2,3,3a,4-tetrahydro-2-carbamoylmethyl-3a-phenyl-8-amino-imidazo[5,1-c][1,4]benzoxazin-1-one;
1H,2,3,3a,4-tetrahydro-2-carbamoylmethyl-3a-phenyl-8-methyl-imidazo[5,1-c][1,4]benzoxazin-1-one;
1H,2,3,3a,4-tetrahydro-2-carbamoylmethyl-3a-phenyl-8-trifluoromethyl-imidazo[5,1-c][1,4]benzoxazin-1-one;
1H,2,3,3a,4-tetrahydro-2-carbamoylmethyl-3a-phenyl-8-methoxy-imidazo[5,1-c][1,4]benzoxazin-1-one;
1H,2,3,3a,4-tetrahydro-2-carbamoylmethyl-3a-phenyl-8-carboxy-imidazo[5,1-c][1,4]benzoxazin-1-one;
1H,2,3,3a,4-tetrahydro-2-carbamoylmethyl-3a-phenyl-8-acetamido-imidazo[5,1-c][1,4]benzoxazin-1-one;
1H,2,3,3a,4-tetrahydro-2-carbamoylmethyl-3a-phenyl-8-methylsulfonyl-imidazo[5,1-c][1,4]benzoxazin-1-one;
1H,2,3,3a,4-tetrahydro-2-carbamoylmethyl-3a-phenyl-8-methylsulfonamido-imidazo[5,1-c][1,4]benzoxazin-1-one;
1H,2,3,3a,4-tetrahydro-2-carbamoylmethyl-imidazo[5,1-c][1,4]benzothiazin-1-one;
1H,2,3,3a,4-tetrahydro-2-carbamoylmethyl-8-chloro-imidazo[5,1-c][1,4]benzothiazin-1-one;
1,2,3,4,4a,5-hexahydro-1-phenyl-3-methyl-pyrazo[2,1-c][1,4]benzoxazine;
1,2,3,4,4a,5-hexahydro-1-phenyl-3-carbamoylmethyl-pyrazo[2,1-c][1,4]benzoxazine;
1,2,3,4,4a,5-hexahydro-1-phenyl-3-carbamoylmethyl-9-chloro-pyrazo[2,1-c][1,4]benzoxazine;
1,2,3,4,4a,5-hexahydro-1-phenyl-3-carbamoylmethyl-pyrazo[2,1-c][1,4]benzoxazin-2-one;
1,2,3,4,4a,5-hexahydro-1-phenyl-3-carbamoylmethyl-9-chloro-pyrazo[2,1-c][1,4]benzoxazin-2-one;
1,2,3,4,4a,5-hexahydro-3-carbamoylmethyl-pyrazo[2,1-c][1,4]benzoxazin-2-one;
1,2,3,4,4a,5-hexahydro-3-carbamoylmethyl-9-chloro-pyrazo[2,1-c][1,4]benzoxazin-2-one;
1,2,3,4,4a,5-hexahydro-3-carbamoylmethyl-pyrazo[2,1-c][1,4]benzoxazin-1-one;
1,2,3,4,4a,5-hexahydro-3-carbamoylmethyl-9-chloro-pyrazo[2,1-c][1,4]benzoxazin-1-one;
3,4,4a,5-tetrahydro-3-carbamoylmethyl-pyrazo[2,1-c][1,4]benzoxazine;
1H,2,3,3a,4-tetrahydro-2-carbamoylmethyl-imidazo[5,1-c][1,4]-benzoxazin-1-thione;
1H,2,3,3a,4-tetrahydro-2-(2'-carbamoyl-ethyl)-imidazo[5,1-c][1,4]benzoxazin-1-thione;
1H,2,3,3a,4-tetrahydro-2-(1'-carbamoyl-ethyl)imidazo[5,1-c][1,4]benzoxazin-1thione;
1H,2,3,3a,4-tetrahydro-2-(1'-methyl-1'-carbamoyl-ethyl)-imidazo[5,1-c][1,4]benzoxazin-1-thione;
1H,2,3,3a,4-tetrahydro-2-carbamoylmethyl-8-chloro-imidazo[5,1-c][1,4]benzoxazin-1-thione;
1H,2,3,3a,4-tetrahydro-2-carbamoylmethyl-imidazo[5,1-c][1,4]benzothiazin-1-thione;
1H,2,3,3a,4-tetrahydro-2-carbamoylmethyl-8-chloro-imidazo[5,1-c][1,4]benzothiazin-1-thione;
1H,2,3,3a,4-tetrahydro-2-carbamoylmethyl-3a-phenyl-imidazo[5,1-c][1,4]benzothiazin-1-thione;
1H,2,3,3a,4-tetrahydro-2-carbamoylmethyl-4-phenyl-imidazo[5,1-c][1,4]benzoxazin-1-thione;
1H,2,3,3a,4-tetrahydro-2-carbamoylmethyl-4,4-dimethyl-imidazo[5,1-c][1,4]benzoxazin-1-thione;
1H,2,3,3a,4-tetrahydro-2-carbamoylmethyl-3a-phenyl-imidazo[5,1-c][1,4]benzothiazin-1-thione;
1H,2,3,3a,4-tetrahydro-2-carbamoylmethyl-4-phenyl-imidazo[5,1-c][1,4]benzothiazin-1-thione;
1H,2,3,3a, 4-tetrahydro-2-carbamoylmethyl-4,4-dimethyl-imidazo[5,1-c][1,4]benzothiazin-1-thione;
1H,2,3,3a,4-tetrahydro-2-thiocarbamoylmethyl-imidazo[5,1-c][1,4]benzoxazin-1-thione;
1H,2,3,3a,4-tetrahydro-2-thiocarbamoylmethyl-imidazo[5,1-c][1,4]benzothiazin-1-thione;
1H,2,3,3a,4-tetrahydro-2-thiocarbamoylmethyl-3a-phenyl-imidazo[5,1-c][1,4]benzoxazin-1-thione;
1H,2,3,3a,4-tetrahydro-2-thiocarbamoylmethyl-4-phenyl-imidazo[5,1-c][1,4]benzoxazin-1-thione;
1H,2,3,3a,4-tetrahydro-2-thiocarbamoylmethyl-4,4-dimethyl-imidazo[5,1-c][1,4]benzoxazin-1-thione;
1H,2,3,3a,4-tetrahydro-2-thiocarbamoylmethyl-3a-phenyl-imidazo[5,1-c][1,4]benzothiazin-1-thione;
1H,2,3,3a,4-tetrahydro-2-thiocarbamoylmethyl-4-phenyl-imidazo[5,1-c][1,4]benzothiazin-1-thione;

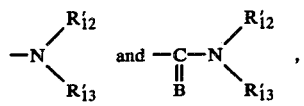

wherein B is as defined above and R'$_{12}$ and R'$_{13}$ are independently selected from the group consisting of hydrogen and C$_1$-C$_6$ alkyl, or R'$_{12}$ and R'$_{13}$, taken together with the nitrogen atom, form a heteromonocyclic ring selected from the group consisting of pirrolidinyl, piperidyl, piperazinyl, oxazolinyl, thiazolinyl and imidazolinyl, optionally substituted by a C$_1$-C$_6$ alkyl group, preferably a methyl or ethyl group; R'$_4$ and R'$_5$ are independently selected from the group consisting of hydrogen, halogen, amino, C$_1$-C$_6$ alkanoylamino, trifluoromethyl, hydroxy, carboxy, C$_1$-C$_6$ alkyl, C$_1$-C$_6$ alkoxy and one of the radicals R$_{10}$—SO$_2$-NH— and —SO$_2$R$_{11}$, wherein R$_{10}$ and R$_{11}$ are as defined above; and R'$_{14}$ is hydrogen, C$_1$-C$_6$ alkyl or

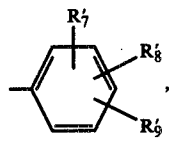

wherein R'$_7$, R'$_8$ and R'$_9$ are as defined above, and the pharmaceutically acceptable salts thereof.

Particularly preferred compounds are those of formula (III)

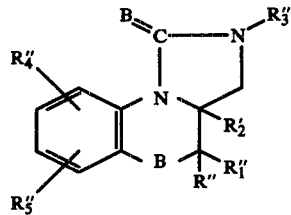

(III)

wherein B and R'$_2$ are as defined above;

R'' and R''$_1$ are independently selected from the group consisting of hydrogen, C$_1$-C$_6$ alkyl and

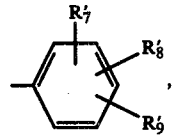

wherein R'$_7$, R'$_8$ and R'$_9$ are as defined above;

R''$_3$ is hydrogen or C$_1$-C$_6$ alkyl, unsubstituted or substituted by one or more substituents selected from the group consisting of (a'') carboxy; (b'') hydroxy; (c'') C$_1$-C$_6$ alkoxy; (d'') —COOR$_{10}$, wherein R$_{10}$ is as defined above; and (e'') one of the radicals

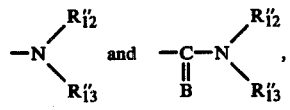

wherein B is as defined above and R''$_{12}$ and R''$_{13}$ are independently selected from the group consisting of hydrogen and C$_1$-C$_6$ alkyl; R''$_4$ and R''$_5$ are independently selected from the group consisting of hydrogen, halogen, amino, acetamido, trifluoromethyl, hydroxy, carboxy, C$_1$-C$_6$ alkyl, C$_1$-C$_6$ alkoxy, CH$_3$—SO$_2$—NH— and —SO$_2$R'$_{11}$, wherein R'$_{11}$ is C$_1$-C$_6$ alkyl or

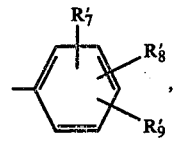

wherein R'$_7$, R'$_8$ and R'$_9$ are as defined above, as well as the pharmaceutically acceptable salts thereof.

Examples of the specific compounds of the invention are the following:

1H,2,3,3a,4-tetrahydro-2-carbamoylmethyl-imidazo[5,1-c][1,4]benzoxazin-1-one;

1H,2,3,3a,4-tetrahydro-2-methyl-imidazo[5,1-c][1,4]benzoxazin-1-one;

1H,2,3,3a,4-tetrahydro-2-(2'-carbamoyl-ethyl)-imidazo[5,1-c][1,4]benzoxazin-1-one;

1H,2,3,3a,4-tetrahydro-2-(1'-carbamoyl-ethyl)-imidazo[5,1-c][1,4]benzoxazin-1-one;

1H,2,3,3a,4-tetrahydro-2-(1'-methyl-1'-carbamoyl-ethyl)-imidazo[5,1-c][1,4]benzoxazin-1-one;

1H,2,3,3a,4-tetrahydro-2-(2'-dimethylaminoethyl)-imidazo [5,1-c][1,4]benzoxazin-1-one;

1H,2,3,3a,4-tetrahydro-2-(3'-dimethylaminopropyl)-imidazo [5,1-c][1,4]benzoxazin-1-one;

1H,2,3,3a,4-tetrahydro-2-carbamoylmethyl-8-chloro-imidazo 5,1-c][1,4]benzoxazin-1-one;

1H,2,3,3a,4-tetrahydro-2-(2'-carbamoyl-ethyl)-8-chloro-imidazo[5,1-c][1,4]benzoxazin-1-one;

1H,2,3,3a,4-tetrahydro-2-carbamoylmethyl-8-fluoro-imidazo [5,1-c][1,4]benzoxazin-1-one;

1H,2,3,3a,4-tetrahydro-2-carbamoylmethyl-8-hydroxy-imidazo [5,1-c][1,4]benzoxazin-1-one;

1H,2,3,3a,4-tetrahydro-2-carbamoylmethyl-8-amino-imidazo [5,1-c][1,4]benzoxazin-1-one;

1H,2,3,3a,4-tetrahydro-2-carbamoylmethyl-8-methyl-imidazo [5,1-c][1,4]benzoxazin-1-one;

1H,2,3,3a,4-tetrahydro-2-carbamoylmethyl-8-trifluoromethyl-imidazo[5,1-c][1,4]benzoxazin-1-one;

1H,2,3,3a,4-tetrahydro-2-carbamoylmethyl-8-methoxy-imidazo [5,1-c][1,4]benzoxazin-1-one;

1H,2,3,3a,4-tetrahydro-2-carbamoylmethyl-8-carboxy-imidazo [5,1-c][1,4]benzoxazin-1-one;

1H,2,3,3a,4-tetrahydro-2-carbamoylmethyl-8-acetamido-imidazo [5,1-c][1,4]benzoxazin-1-one;

1H,2,3,3a,4-tetrahydro-2-carbamoylmethyl-8-methylsulfonyl-imidazo[5,1-c][1,4]benzoxazin-1-one;

1H,2,3,3a,4-tetrahydro-2-carbamoylmethyl-8-methylsulfonamido-imidazo[5,1-c][1,4]benzoxazin-1-one;

1H,2,3,3a,4-tetrahydro-2-(3'-dimethylaminopropyl)-4-phenyl-imidazo[5,1-c][1,4]benzoxazin-1-one;

1H,2,3,3a,4-tetrahydro-1,1-dimethyl-2-carbamoylmethyl-imidazo[5,1-c][1,4]benzoxazine;

1H,2,3,3a,4-tetrahydro-2-carbamoylmethyl-4-phenyl-imidazo[5,1-c][1,4]benzoxazin-1-one;

1H,2,3,3a,4-tetrahydro-2-(2'-carbamoyl-ethyl)-4-phenyl-imidazo[5,1-c][1,4]benzoxazin-1-one;

1H,2,3,3a,4-tetrahydro-2-(1'-carbamoyl-ethyl)-4-phenyl-imidazo[5,1-c][1,4]benzoxazin-1-one;

1H,2,3,3a,4-tetrahydro-2-(1'-methyl-1'-carbamoyl-ethyl)-4-phenyl-imidazo[5,1-c][1,4]benzoxazin-1-one;

1H,2,3,3a,4-tetrahydro-2-thiocarbamoylmethyl-4,4-dimethyl-imidazo[5,1-c][1,4]benzothiazin-1-thione, as well as the pharmaceutically acceptable salts thereof.

The compounds of the present invention are prepared by a process comprising:

(a) reacting a compound of formula (IV)

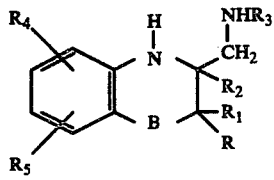  (IV)

wherein

B, R, $R_1$, $R_2$, $R_3$, $R_4$ and $R_5$ are as defined above, with a compound of formula $R_{14}$—CO—$R_{15}$, wherein $R_{14}$ and $R_{15}$ are as defined above, so obtaining compounds of formula (I) wherein Z is

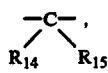

wherein $R_{14}$ and $R_{15}$ are as defined above; or (b) cyclizing a compound of formula (IV), wherein B, R, $R_1$, $R_2$, $R_3$, $R_4$ and $R_5$ are as defined above, so obtaining compounds of formula (I) wherein Z is >C=B, wherein B is as defined above; or (c) cyclizing a compound of formula (V)

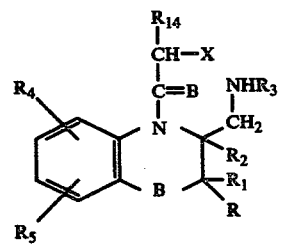  (V)

wherein

B, R, $R_1$, $R_2$, $R_4$, $R_5$ and $R_{14}$ are as defined above and $R_3$ does not contain the radical

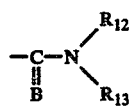

and X is a halogen atom, so obtaining compounds of formula (I) wherein Z is

wherein A is >C=B, wherein B is as defined above, and $R_{14}$ is as defined above; or (d) cyclizing a compound of formula (VI)

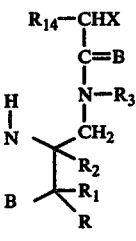  (VI)

wherein

B, R, $R_1$, $R_2$, $R_4$, $R_5$, $R_{14}$ and X are as defined above and $R_3$ does not contain the radical

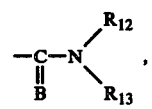

so obtaining compounds of formula (I) wherein Z is

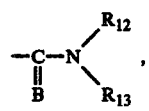

wherein A is >C=B, wherein B is as defined above, and $R_{14}$ is as defined above; or (e) cyclizing a compound of formula (VII)

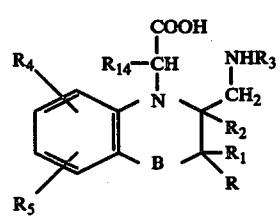  (VII)

wherein

B, R, $R_1$, $R_2$, $R_4$, $R_5$ and $R_{14}$ are as defined above, or a reactive derivative thereof, and $R_3$ does not contain the radical

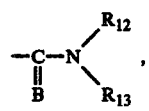

so obtaining compounds of formula (I) wherein Z is

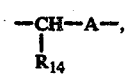

wherein A is >C=O, and $R_{14}$ is as defined above; or (f) cyclizing a compound of formula (VIII)

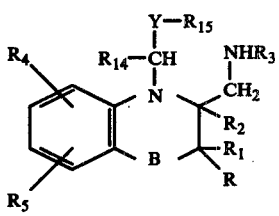
(VIII)

wherein
B, R, $R_1$, $R_2$, $R_4$, $R_5$, $R_{14}$ and $R_{15}$ are as defined above, and $R_3$ is different from hydrogen and does not contain the radical

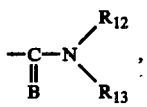

and Y is a protected aldehyde or keto group, so obtaining compounds of formula (I) wherein Z is

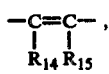

wherein $R_{14}$ and $R_{15}$ are as defined above and $R_3$ is different from hydrogen; or (g) reducing a compound of formula (IX)

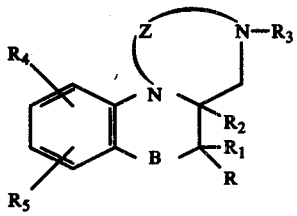
(IX)

wherein
B, R, $R_1$, $R_2$, $R_4$ and $R_5$ are as defined above, Z is

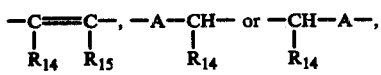

wherein A is $>C=B$, wherein B is as defined above and $R_{14}$ and $R_{15}$ are as defined above and wherein $R_3$ is as defined above, provided that when Z is

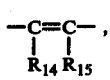

$R_3$ is different from hydrogen, so obtaining compounds of formula (I) wherein Z is

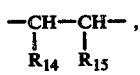

wherein $R_{14}$ and $R_{15}$ are as defined above; and/or, if desired, reacting a compound of formula (X)

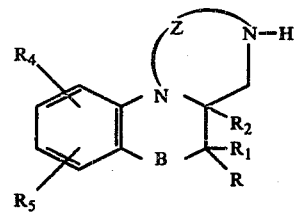
(X)

wherein
Z, B, R, $R_1$, $R_2$, $R_4$ and $R_5$ are as defined above, or a salt thereof, with a compound of formula (XI)

$R_3-W$ (XI)

wherein
$R_3$ is as defined above, except hydrogen and W is halogen or the residue of an active ester of an alcohol, and/or, if desired, converting a compound of formula (I) into another compound of formula (I) and/or, if desired, salifying a compound of formula (I) and/or, if desired, obtaining a free compound of formula (I) from a salt and/or, if desired, resolving a mixture of stereoisomers into the single isomers. The reaction of the compound of formula (IV) with the compound of formula $R_{14}-CO-R_{15}$ may be preferably carried out at the boiling temperature in an organic solvent, which forms an azeotrope with water, such as benzene and toluene: the formed water is continuously removed by distilling off the formed azeotrope; the same reaction may be also carried out at the reflux temperature in other organic solvents, such as, acetic acid or lower aliphatic alcohols. The reaction may be carried out either in the presence or in the absence of a catalyst, depending on the reactivity of the carbonyl group: when used, the catalyst is preferably an acid, e.g., p-toluenesulphonic acid.

The cyclization of the compound of formula (IV) is preferably performed by reaction with an alkyl haloformate, carbonyldiimidazole, phosgene or urea or the corresponding thio-derivatives. When the cyclization of the compound of formula (IV) is carried our by reaction with an alkyl haloformate, carbonyldiimidazole, phosgene or the corresponding thio-derivatives, it is preferably performed in organic solvents, such as, toluene, benzene, xylene, at temperatures ranging between about 50° C. to about 100° C. The alkyl haloformate is preferably ethyl chloroformate. The cyclization of the compound of formula (IV) may be also effected by fusion of the compound of formula (II) either with the stoichiometric amount of urea or thiourea, so obtaining, starting from compounds of formula (IV) wherein $R_3$ is hydrogen, compounds of formula (I) wherein $R_3$ is hydrogen, or with an excess of the same reagents, so obtaining, starting from compounds of formula (IV) wherein $R_3$ is hydrogen, compounds of formula (I) wherein $R_3$ is carbamoyl or thiocarbamoyl.

In all the other cases, the meaning of $R_3$ in the compounds of formula (I) obtained by the cyclization, using both an excess and a stoichiometric amount of urea and thiourea, is always that already present in the compound of formula (IV) employed as starting material. The cyclization of the compound of formula (V) is preferably performed by heating the compound of formula (V) in organic solvents, such as, dimethylacetamide, dimethylformamide, dimethylsulphoxide, in the presence of an acceptor of the hydrohalic acid formed during the reaction, such as, for example an alkaline or alkaline-earth metal carbonate or bicarbonate. The cyclization of the compound of formula (VI) may be preferably performed by heating this compound at temperatures ranging from about 40° C. to about 150° C. in dipolar aprotic solvents, such as, dimethylformamide and dimethylacetamide, in the presence of an acceptor of the hydrohalic acid, as mentioned above.

The cyclization of the compound of formula (VII) may be preferably carried out at the boiling temperature either in water, preferably at a pH varying between 7.5 and 8.5 or in organic solvents, such as, lower aliphatic alcohols, dimethylacetamide and dimethylformamide. The compound of formula (VII) may be also reacted as a reactive derivative, such as, e.g., an acid halide, an anhydride, a mixed anhydride or a reactive ester. The cyclization of the compound of formula (VIII) may be preferably effected at the boiling temperature in water, using an acid, preferably an inorganic acid, such as, hydrochloric acid, as a catalyst. In the compound of formula (VIII) $R_{14}$ is preferably phenyl, optionally substituted as stated above.

In the compound of formula (VIII) the protection of the aldehyde or keto group is performed by making the acetal or the ketal thereof by the usual methods of organic chemistry. At the end of the reaction, the protecting groups are removed, e.g., by acid hydrolysis, e.g., with HCl or diluted $H_2SO_4$ in an aqueous or alcoholic-/aqueous solution.

The reduction of the compound of formula (IX) wherein Z is

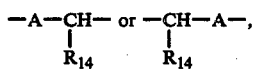

wherein $R_{14}$ is as defined above and A is $>C=B$, wherein B is as defined above, may be preferably carried out by using mixed hydrides, for example, lithium aluminium hydride, in organic solvents, such as, ethyl ether, tetrahydrofuran and dioxane, at temperatures ranging from about 40° C. to about 60° C.

The reduction of the compound (IX), wherein Z is

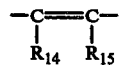

is preferably carried out by catalytic way, using Pd/C or Pt/C in a solvent such as water, an aliphatic alcohol, acetic acid or a mixture thereof, at temperatures ranging from the room temperature to about 100° C., at 1-7 atmospheres.

In the compound of formula (XI), when W is an halogen atom, it is preferably chlorine, bromine, or iodine; when W is the residue of an active ester of an alcohol, it is preferably the radical $-O-SO_2-R_{16}$, wherein $R_{16}$ is an alkyl, e.g., $C_1-C_6$ alkyl, or an aryl group: when $R_{16}$ is alkyl, it is preferably methyl, while when $R_{16}$ is aryl, it is preferably phenyl, preferably substituted by an alkyl group, in particular a methyl group, in the para-position, i.e., a tosyl group.

When in the compound of formula (X) Z is

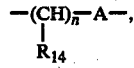

wherein $n$ is as defined above and A is $>C=O$, the compound of formula (X) is preferably reacted with the compound of formula (XI) as a salt, in particular an alkaline salt, which can be prepared by known methods, for example, by reacting a compound of formula (X), wherein Z is as hereabove defined, with an alkaline hydride, e.g., sodium hydride, or with lithium diethylamine or diisopropylamide or directly with an alkaline metal, and the reaction with the compound of formula (XI) is preferably carried out either in anhydrous aprotic solvents, such as, e.g., dimethylformamide, dimethylacetamide or dimethylsulphoxide, or in other solvents, such as, e.g., benzene, toluene, dioxane or tetrahydrofuran, at temperatures ranging from about 50° C. to about 150° C.

When in the compound of formula (X) Z has the other meanings indicated above, the compound of formula (X) is preferably reacted with the compound of formula (XI) in the free, i.e., unsalified form and the reaction is preferably effected in the presence of a strong acid acceptor, such as, for example, an alkaline or alkaline-earth metal carbonate or bicarbonate, in an organic solvent, such as, dimethylformamide, dimethylacetamide, dimethylsulphoxide or aliphatic alcohols, for example, t.butyl alcohol at temperatures ranging from about 50° C. to about 150° C.

When in the above described reactions as well as in the reactions that will be described subsequently, the starting materials contain one or more groups which may interfere in the reaction, these groups are protected, if necessary, in a conventional manner and are then removed, at the end of the reaction, in a conventional manner too.

For example, when $R_3$ is a $C_1-C_6$ alkyl group substituted by a $-COR_{11}$ group, wherein $R_{11}$ is as defined above, and it is desired to make a reduction with LiAlH$_4$ without reducing the keto group, the keto group may be protected by conversion into a ketal group; this conversion may be effected by reaction with ethylene glycol, using an acid, e.g., p-toluenesulphonic acid as a catalyst, either in the absence or in the presence of solvents, such as, benzene or toluene. The ketal group may be converted again into a keto group by acid hydrolysis, for example, with a strong acid, such as, hydrochloric acid.

When $R_3$ is $C_2-C_6$ alkenyl and a catalytic reduction with Pd/C at room temperature and atmospheric pressure is effected, the alkenyl group may be protected from the reduction by converting it into an epoxide by reaction with a peracid, such as, for example, peracetic or m-chloro-perbenzoic acid, in organic solvents, such as, methylene chloride, chloroform and then converting again the epoxide into a double bond by hydrolysis with alkalies or acids and subsequent dehydration.

As stated above, a compound of formula (I) may be converted into another compound of formula (I) by the usual methods of organic chemistry.

For example, a compound of formula (I), wherein Z is $>C=O$, may be converted into a compound of formula (I), wherein Z is $>C=S$, by reaction with phosphorus pentasulphide; this reaction may be effected either by fusion of the two compounds or by heating under reflux a solution thereof in a solvent, such as, for example, benzene or toluene.

A compound of formula (I), wherein $R_3$ is an alkyl group substituted by a radical

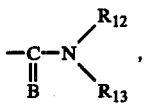

wherein B is as defined above and $R_{12}$ and $R_{13}$ are independently selected from the group consisting of hydrogen and $C_1$–$C_6$ alkyl, may be converted into a compound of formula (I), wherein $R_3$ is an alkyl group substituted by a radical

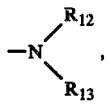

wherein $R_{12}$ and $R_{13}$ are as defined above, by reduction e.g., with $LiAlH_4$ in the usual conditions for this kind of reduction.

A compound of formula (I), wherein $R_3$ is an alkyl group substituted by a radical

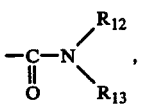

wherein $R_{12}$ and $R_{13}$ are as defined above, may be converted into a compound of formula (I), wherein $R_3$ is an alkyl group substituted by a radical

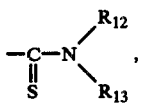

wherein $R_{12}$ and $R_{13}$ are as defined above, by reaction e.g., with phosphorus pentasulphide, either by fusion or by heating under reflux as described above. A compound of formula (I), wherein $R_3$ is an alkyl group substituted by a radical —$COR_{11}$ or —$COOR_{11}$, wherein $R_{11}$ is as defined above, may be converted into a compound of formula (I), wherein $R_3$ is an alkyl group substituted by a hydroxy group by reduction, e.g., with $LiAlH_4$. A compound of formula (I), wherein $R_3$ is an alkyl group substituted by a radical —$COOR_{11}$, wherein $R_{11}$ is as defined above, or by a radical

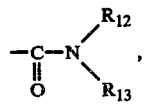

wherein $R_{12}$ and $R_{13}$ are as defined above, may be converted into a compound of formula (I), wherein $R_3$ is an alkyl group substituted by a carboxyl group, by acid or alkaline hydrolysis, for example, with sodium or potassium hydroxide or with hydrochloric or sulphuric acid.

Also the salification of the compound of formula (I) as well as the conversion of a salt into a free compound and the resolution of a mixture of stereoisomers, may be carried out by conventional methods, as is known to those skilled in the art. So racemic compounds may be resolved into the optical antipodes, for example, by resolution, e.g., by means of fractionated crystallization, of mixtures of diastereoisomeric salts and, is desired, liberating the optical antipodes from the salts.

The compound of formula (IV), wherein $R_3$, $R_4$, $R_5$ and B are as defined above, $R_2$ is hydrogen, R and $R_1$ are as defined above provided that, when one of R and $R_1$ is hydrogen, the other is different from optionally substituted phenyl, may be prepared, for example, by hydrolysis of a compound of formula (XII)

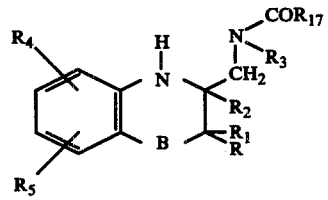

wherein B, R, $R_1$, $R_2$, $R_3$, $R_4$ and $R_5$ are as hereabove defined and $R_{17}$ is hydrogen, or trihaloalkyl, or —$COR_{17}$ and $R_3$, taken together, form a cyclic imide having one of the following formulae

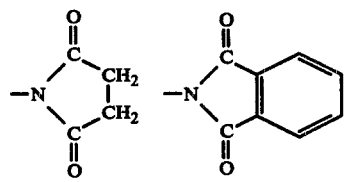

In the compound of formula (XII) as well as in the compounds mentioned below, when $R_{17}$ is trihaloalkyl, it is preferably trifluoromethyl.

The hydrolysis of the compound of formula (XII) may be carried out by using an acid, for example, a concentrated hydrohalic acid in an aqueous medium.

When in the compound of formula (XII), the radicals —$COR_{17}$ and $R_3$, taken together, form a cyclic imide, having one of the above formulae, the hydrolysis of the compound of formula (XII) gives a compound of formula (IV), wherein $R_3$ is hydrogen.

The compound of formula (XII), wherein $R_2$ is hydrogen, may be obtained by reduction and simultaneous cyclization of a compound of formula (XIII)

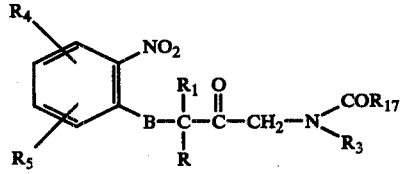

wherein B, R, $R_1$, $R_3$, $R_4$, $R_5$ and $R_{17}$ are as defined above. The compound of formula (XIII) may be, in turn, prepared by a method analogous to that described in Synthesis, 9, 660 (1974) or by reaction of a compound of formula (XIV)

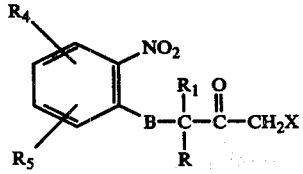

wherein B, R, $R_1$, $R_4$ and $R_5$ are as defined above and X is as defined above, with a compound of formula (XV)

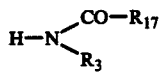  (XV)

wherein $R_3$ and $R_{17}$ are as defined above, using a method analogous to that described in J.Med.Chem., 19, 632 (1976).

The reduction with simultaneous cyclization of a compound of formula (XIII) is preferably effected, when B is an oxygen atom, by catalytic way, using Pd/C, e.g., 10% Pd/C, at a temperature ranging from about 30° C. to about 80° C., at a pressure ranging from about 3 to about 4 atmospheres, in an organic solvent, such as, lower aliphatic alcohols or acetic acid. When in the compound of formula (XIII) B is a sulphur atom, the same reaction is preferably carried out by treatment with metals in an acidic medium, for example, zinc or iron in hydrochloric acid, or with stannous chloride in hydrochloric and/or acetic acid.

The compound of formula (IV) wherein R, $R_1$, $R_2$, $R_3$, $R_4$, $R_5$ and B have all the meanings indicated above, may be prepared by reduction of a compound of formula (XVI)

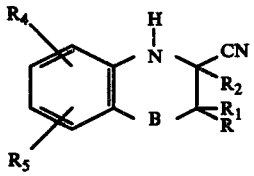  (XVI)

wherein

B, R, $R_1$, $R_2$, $R_4$ and $R_5$ have all the meanings indicated above, so obtaining a compound of formula (IV), wherein B, R, $R_1$, $R_2$, $R_4$ and $R_5$ have all the meanings indicated above and $R_3$ is hydrogen, followed by alkylation, with a compound of formula (XI), in the reaction conditions described above.

The reduction of the compound of formula (XVI) wherein B is an oxygen atom, may be carried out, for example, by using Ni/Raney in a solvent, such as, for example, a lower aliphatic alcohol. The reduction of the compound of formula (XVI) wherein B is a sulphur atom, is preferably effected by treatment with a metal in an acidic medium, for example, zinc or iron in hydrochloric acid, or with stannous chloride in hydrochloric and/or acetic acid.

The alkylation of the compound of formula (IV), wherein $R_3$ is hydrogen, may be carried out, for example, in an anhydrous aprotic solvent, such as, dimethylformamide, dimethylacetamide and dimethylsulphoxide or in other solvents, such as, benzene, toluene, dioxane and tetrahydrofuran, at temperatures ranging from about 50° C. to about 150° C., in the presence of an acceptor of hydrohalic acids, such as, for example, an alkaline carbonate or bicarbonate.

The compound of formula (XVI) may be prepared by reacting a compound of formula (XVII)

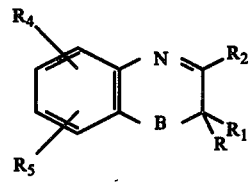  (XVII)

wherein B, R, $R_1$, $R_2$, $R_4$ and $R_5$ are as defined above, with HCN, following, for example, the method described in J.Org.Chem., 24, 1905 (1959).

The compound of formula (IV), wherein B, R, $R_1$, $R_2$, $R_3$, $R_4$ and $R_5$ have all the above mentioned meanings, may also be prepared starting from a compound of formula (IV), wherein B, R, $R_1$, $R_2$, $R_4$ and $R_5$ are as defined above, and $R_3$ is hydrogen, by simultaneous acylation of both the amino groups, so obtaining a compound of formula (XVIII)

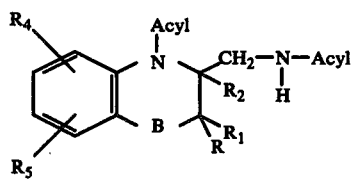  (XVIII)

wherein B, R, $R_1$, $R_2$, $R_4$ and $R_5$ are as defined above, and by subsequent alkylation of the compound of formula (XVIII) with a compound of formula (XI), followed by hydrolysis of the so obtained compound, in order to remove the acyl groups.

The alkylation of the compound of formula (XVIII) may be performed by the usual methods of the organic chemistry, e.g., as stated above, either in anhydrous aprotic solvents, such as, dimethylformamide, dimethylacetamide, dimethylsulphoxide, or in other solvents, such as, benzene, toluene, dioxane, tetrahydrofuran, at temperatures ranging from about 50° C. to about 150° C., in the presence of the usual acceptors of strong acids.

Both the acylation and the subsequent hydrolysis are also effected by known methods, such as, e.g. those herebelow reported. The compound of formula (V) may be prepared by hydrolysis of a a compound of formula (XIX)

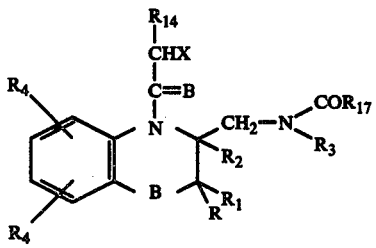  (XIX)

wherein B, R, $R_1$, $R_2$, $R_3$, $R_4$, $R_5$, $R_{14}$, X are as defined above, and $R_{17}$ is hydrogen or trihaloalkyl.

The hydrolysis is effected under mild reaction conditions, for example, with hydrohalic acids in aqueous-alcoholic solutions or, when $R_{17}$ is trihaloalkyl, in particular, trifluoromethyl, by reduction with $NaBH_4$.

The compound of formula (XIX) may be, in turn, prepared by acylation of a compound of formula (XII), wherein B, R, $R_1$, $R_2$, $R_3$, $R_4$, $R_5$ are as defined above, and $R_{17}$ is hydrogen or trihaloalkyl, with an acid of formula

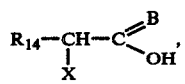

wherein $R_{14}$, X and B are as defined above, or a reactive derivative thereof.

The compound of formula (XII) wherein B, R, $R_1$, $R_2$, $R_3$, $R_4$, $R_5$ have all the meanings indicated above and $R_{17}$ is hydrogen or trihaloalkyl, may be prepared starting from a compound of formula (IV) by acylation with a compound of formula $R_{17}$—COOH or a reactive derivative thereof, such as, e.g., an acid halide, a mixed anhydride or a reactive ester thereof.

Both the acylation reactions may be carried out in an organic solvent, such as, chloroform, ethyl ether, tetrahydrofuran, acetone or in aprotic dipolar solvents, in the presence of an acceptor of hydrohalic acids, such as, for example, an alkaline or alkaline-earth carbonate or bicarbonate, or an organic basis, such as, triethylamine or N,N-dimethylaniline or, when $R_{17}$ is hydrogen, with formic acid in ethyl or methyl formate.

The reactive derivative of the acid of formula

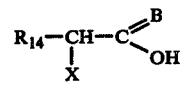

may be a halide, a mixed anhydride or a reactive ester. The compound of formula (VI) may be prepared by acylation of the compound of formula (IV) with an acid of formula

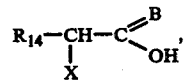

wherein $R_{14}$, X and B are as defined above, or a reactive derivative thereof, for example, a halide, an anhydride, a mixed anhydride or a reactive ester.

The acylation may be performed as usual, in an organic solvent, such as, chloroform, methylene chloride, ethyl ether, tetrahydrofuran or acetone in the presence of the usual acceptors of hydrohalic acids, under stirring and taking care to add slowly, at a law temperature, e.g. $-50°$ C., the reactive derivative of the acid to a solution containing an excess of the compound of formula (IV).

The compound of formula (VII) may be prepared by hydrolysis of a compound of formula (XX)

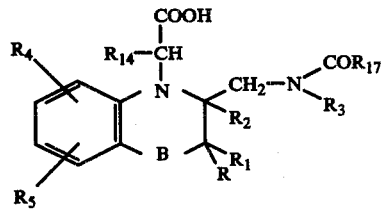

wherein B, R, $R_1$, $R_2$, $R_3$, $R_4$, $R_5$ and $R_{14}$ are as defined above, and $R_{17}$ is hydrogen or trihaloalkyl or the radicals —$COR_{17}$ and $R_3$, taken together, form an imide having one of the formulas hereabove reported.

The hydrolysis may be carried out, for example, with 37% hydrochloric acid at the reflux temperature in an aqueous-alcoholic solution for 14–16 hours, or with $NaBH_4$ when $R_{17}$ is trihaloalkyl, in particular, trifluoromethyl.

The compound of formula (XX) may be, in turn, prepared starting from a compound of formula (XII), by alkylation with a compound of formula

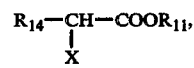

wherein $R_{11}$, $R_{14}$ and X are as defined above, and by subsequent mild alkaline hydrolysis of the obtained compound. The alkylation may be effected in aprotic dipolar solvents, in the presence of the usual acceptors of hydrohalic acids and the mild hydrolysis may be performed, for example, with sodium or potassium hydroxide in an alcoholic solution, at room temperature for about 12–24 hours.

The compound of formula (VIII) may be prepared by basic hydrolysis of a compound of formula (XXI)

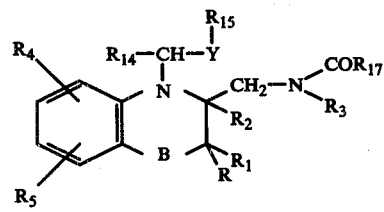

wherein B, R, $R_1$, $R_2$, $R_3$, $R_4$, $R_5$, $R_{14}$, $R_{15}$ and Y are as defined above, and $R_{17}$ is trihaloalkyl or the radicals —$COR_{17}$ and $R_3$, taken together, form an imide having one of the formulae hereabove reported. The hydrolysis is preferably carried out with boric acid, according to the method described in Ann.Chem.(1973), 87 or with trifluoroacetic acid in chloroform.

The compound of formula (XXI) may be, in turn, prepared by alkylation of a corresponding compound of formula (XII) with an α-halo-ketone or with an α-haloaldehyde in the form of a protected derivative thereof, such as, for example, an acetal or a ketal, preferably in an aprotic dipolar solvent, e.g., dimethylformamide, and in the presence of the usual acceptors of hydrohalic acids.

The protecting groups are then removed at the end of the reaction by known methods, e.g., by acid hydrolysis, e.g., with HCl in an aqueous or alcoholic/aqueous solution.

The compound of formula (IX) may be prepared according to each of the methods from (c) to (f) reported above.

The compound of formula (X) may be prepared by each of the methods from (a) to (g) reported above.

The compound of formula (XI) may be prepared according to the usual methods of organic chemistry.

The compounds of the present invention are active on the central nervous system, in particular as antidepressant agents. The antidepressant activity was evaluated in mice on the basis of the prevention of reserpine-induced blepharospasm and hypothermia. Reserpine was administered endoperitoneally at a dosage of 2.5 mg/kg, and the tested compounds were orally administered 30 minutes before the administration of reserpine. Recording of blepharospasm [evaluated in scores according to the technique described by Rubin B. et al. in J.Pharmacol., 120, 125 (1957)] and measurement of body temperature (by means of a rectal thermocouple) were taken an hour, and respectively four hours after the administration of reserpine. The compounds of the present invention are preferably administered orally, although they can be administered also in other conventional ways, for example, by injection or by rectal way.

The dosage suitable for the oral administration to adult humans of the compounds of the invention, for example, 1H,2,3,3a,4-tetrahydro-2-carbamoylmethyl-imidazo[5,1-c][1,4]benzoxazin-1-one and 1H,2,3,3a,4-tetrahydro-2-carbamoylmethyl-8-chloroimidazo[5,1-c][1,4]benzoxazin-1-one, is preferably 20–50 mg pro dose 2–4 times a day.

The pharmaceutical compositions containing the compounds of the invention are prepared according to conventional methods with the usual ingredients.

Thus, for oral administration, the pharmaceutical compositions containing the compounds of the invention are preferably tablets, pills or capsules which contain the active substance together with diluents, such as, for example, lactose, dextrose, sucrose, mannitol, sorbitol, cellulose; lubricants, for instance, silica, talc, stearic acid, magnesium or calcium stearate and/or polyethylene glycols; or they may also contain binders, such as, for example, starches, gelatine, methylcellulose, gum-arabic, tragacanth, polyvinylpyrrolidone; disintegrating agents, such as, for instance, starches, alginic acid, alginates; effervescing mixtures; dyestuffs; sweeteners; wetting agents, such as, for instance, lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

Also the other pharmaceutical formulations containing the compounds of the invention may be prepared by known methods and they can be, for example, syrups or drops for the oral administration, sterile solutions for injection, or suppositories.

The following examples illustrate but do not limit the present invention.

EXAMPLE 1

To a solution of 1H,2,3,3a,4-tetrahydro-imidazo[5,1-c][1,4]benzoxazin-1-one (3.5 g; $1.85 \cdot 10^{-2}$ moles) in dimethylformamide (70 ml), 50% NaH (0.89 g; $1.85 \cdot 10^{-2}$ moles) was added. The solution was stirred for 1 hour at room temperature, then chloroacetamide (1.75 g; $1.85 \cdot 10^{-2}$ moles) dissolved in dimethylformamide (20 ml) was added. The mixture was stirred 20 hours at room temperature then poured in water and extracted with CHCl$_3$. By evaporation to dryness, 1H,2,3,3a,4-tetrahydro-2-carbamoylmethyl-imidazo[5,1-c][1,4]benzoxazin-1-one, (2.8 g; m.p. 224°–225° C.) was obtained.

Analogously, the following compounds were obtained:

1H,2,3,3a,4-tetrahydro-2-methyl-imidazo[5,1-c][1,4]benzoxazin-1-one, m.p. 135°–136° C.;
1H,2,3,3a,4-tetrahydro-2-(2'-carbamoyl-ethyl)-imidazo[5,1-c][1,4]benzoxazin-1-one;
1H,2,3,3a,4-tetrahydro-2-(1'-carbamoyl-ethyl)-imidazo[5,1-c][1,4]benzoxazin-1-one;
1H,2,3,3a,4-tetrahydro-2-(1'-methyl-1'-carbamoyl-ethyl)-imidazo[5,1-c][1,4]benzoxazin-1-one;
1H,2,3,3a,4-tetrahydro-2-(2'-dimethylaminoethyl)-imidazo[5,1-c][1,4]benzoxazin-1-one, m.p. 218°–221° C. (hydrochloride);
1H,2,3,3a,4-tetrahydro-2-(3'-dimethylaminopropyl)-imidazo[5,1-c][1,4]benzoxazin-1-one, m.p. 54°–57° C.;
1H,2,3,3a,4-tetrahydro-2-propargyl-imidazo[5,1-c][1,4]benzoxazin-1-one, m.p. 113°–115° C.;
1H,2,3,3a,4-tetrahydro-2-benzyl-imidazo[5,1-c][1,4]benzoxazin-1-one;
1H,2,3,3a,4-tetrahydro-2-(p-methylsulfonyl-benzyl)-imidazo[5,1-c][1,4]benzoxazin-1-one;
1H,2,3,3a,4-tetrahydro-2-(3'-t-amylsulfonylpropyl)-imidazo[5,1-c][1,4]benzoxazin-1-one;
1H,2,3,3a,4-tetrahydro-2-carbamoylmethyl-8-chloro-imidazo[5,1-c][1,4]benzoxazin-1-one, m.p. 214°–216° C.;
1H,2,3,3a,4-tetrahydro-2-carbamoylmethyl-8-fluoro-imidazo[5,1-c][1,4]benzoxazin-1-one;
1H,2,3,3a,4-tetrahydro-2-carbamoylmethyl-8-hydroxy-imidazo[5,1-c][1,4]benzoxazin-1-one;
1H,2,3,3a,4-tetrahydro-2-carbamoylmethyl-8-amino-imidazo[5,1-c][1,4]benzoxazin-1-one;
1H,2,3,3a,4-tetrahydro-2-carbamoylmethyl-8-methyl-imidazo[5,1-c][1,4]benzoxazin-1-one, m.p. 235°–237° C.;
1H,2,3,3a,4-tetrahydro-2-carbamoylmethyl-8-trifluoromethyl-imidazo[5,1-c][1,4]benzoxazin-1-one;
1H,2,3,3a,4-tetrahydro-2-carbamoylmethyl-8-methoxy-imidazo[5,1-c][1,4]benzoxazin-1-one;
1H,2,3,3a,4-tetrahydro-2-carbamoylmethyl-8-carboxy-imidazo[5,1-c][1,4]benzoxazin-1-one;
1H,2,3,3a,4-tetrahydro-2-carbamoylmethyl-8-acetamido-imidazo[5,1-c][1,4]benzoxazin-1-one;
1H,2,3,3a,4-tetrahydro-2-carbamoylmethyl-8-methylsulfonyl-imidazo[5,1-c][1,4]benzoxazin-1-one;
1H,2,3,3a,4-tetrahydro-2-carbamoylmethyl-8-methylsulfonamido-imidazo[5,1-c][1,4]benzoxazin-1-one.

EXAMPLE 2

To 1H,2,3,3a,4-tetrahydro-imidazo[5,1-c][1,4]benzoxazine (4 g; $2.1 \cdot 10^{-2}$ moles) in anhydrous dimethylformamide (80 ml), NaH (0.05 g) was added; after 30 minutes at room temperature, ethyl acrylate (1.05 g; $2.1 \cdot 10^{-2}$ moles) was added. The mixture was kept 2 hours at room temperature and other 2 hours at 50° C., then poured in water, extracted with ethyl acetate, evaporated to dryness and the residue was hydrolyzed in methanolic 2N KOH (100 ml) at room temperature for 12 hours. After evaporation to dryness, the residue was taken up with water, the obtained solution was acidified with 8% HCl and extracted with CHCl$_3$; after drying on Na$_2$SO$_4$, SOCl$_2$ (5 ml) was added and the mixture stirred overnight at room temperature. The chloroform was evaporated, the residue was taken up twice with toluene and twice evaporated to dryness, then takep up again with an ethanolic ammonia solution; the mixture was allowed to rest for 12 hours and then, after evaporation to dryness, crystallization from 95% ethanol, 1H,2,3,3a,4-tetrahydro-2-(2'-carbamoyl-ethyl)-imidazo[5,-c][1,4]benzoxazin-1-one, (2.3 g) was obtained.

Analogously, the following compounds were obtained:

1H,2,3,3a,4-tetrahydro-2-(2'-carbamoyl-ethyl)-8-chloro-imidazo[5,1-c][1,4]benzoxazin-1-one;
1H,2,3,3a,4-tetrahydro-2-(2'-carbamoyl-ethyl)-8-amino-imidazo[5,1-c][1,4]benzoxazin-1-one;

1H,2,3,3a,4-tetrahydro-2-(2'-carbamoyl-ethyl)-8-methyl-imidazo[5,1-c][1,4]benzoxazin-1-one;
1H,2,3,3a,4-tetrahydro-2-(2'-carbamoyl-ethyl)-8-methoxy-imidazo[5,1-c][1,4]benzoxazin-1-one.

EXAMPLE 3

A mixture of 2H-3,4-dihydro-3-aminomethyl[1,4]benzoxazine (22.4 g; $1.36.10^{-1}$ moles) and urea (9.74 g; $1.62.10^{-1}$ moles) was heated to fusion for 2 hours and 30 minutes at 160° C. in an oil bath, then cooled and the solid ground in water. By filtration and crystallization from ethyl acetate, 1H,2,3,3a,4-tetrahydro-imidazo[5,1-c][1,4]benzoxazin-1-one (15.5 g; yield = 60%; m.p. 168°-170° C.) was obtained.

Analogously, the following compounds were obtained:
1H,2,3,3a,4-tetrahydro-8-chloro-imidazo[5,1-c][1,4]benzoxazin-1-one, m.p. 201°-203° C.;
1H,2,3,3a,4-tetrahydro-8-fluoro-imidazo[5,1-c][1,4]benzoxazin-1-one;
1H,2,3,3a,4-tetrahydro-8-hydroxy-imidazo[5,1-c][1,4]benzoxazin-1-one;
1H,2,3,3a,4-tetrahydro-8-amino-imidazo[5,1-c][1,4]benzoxazin-1-one;
1H,2,3,3a,4-tetrahydro-8-methyl-imidazo[5,1-c][1,4]benzoxazin-1-one, m.p. 190°-193° C.;
1H,2,3,3a,4-tetrahydro-8-trifluoromethyl-imidazo[5,1-c][1,4]benzoxazin-1-one;
1H,2,3,3a,4-tetrahydro-8-methoxy-imidazo[5,1-c][1,4]benzoxazin-1-one;
1H,2,3,3a,4-tetrahydro-8-carboxy-imidazo[5,1-c][1,4]benzoxazin-1-one;
1H,2,3,3a,4-tetrahydro-8-acetamido-imidazo[5,1-c][1,4]benzoxazin-1-one;
1H,2,3,3a,4-tetrahydro-8-methylsulfonyl-imidazo[5,1-c][1,4]benzoxazin-1-one;
1H,2,3,3a,4-tetrahydro-8-methylsulfonamido-imidazo[5,1-c][1,4]benzoxazin-1-one.

EXAMPLE 4

To a solution of 2H-3,4-dihydro-3-aminomethyl[1,4]benzoxazine (3.28 g; $2.10^{-2}$ moles) dissolved in anhydrous tetrahydrofuan, carbonyldiimidazole (3.25 g; $2.10^{-2}$ moles) was added under a nitrogen steam and stirred a week at room temperature. After evaporation to dryness, the residue was ground more times in water so obtaining, after crystallization from ethyl acetate, 1H,2,3,3a,4-tetrahydro-imidazo[5,1-c][1,4]benzoxazin-1-one (g 3; m.p. 168°-170° C.).

Analogously, the following compounds were obtained:
1H,2,3,3a,4-tetrahydro-8-chloro-imidazo[5,1-c][1,4]benzoxazin-1-one, m.p. 201°-203° C.;
1H,2,3,3a,4-tetrahydro-8-fluoro-imidazo[5,1-c][1,4]benzoxazin-1-one;
1H,2,3,3a,4-tetrahydro-8-hydroxy-imidazo[5,1-c][1,4]benzoxazin-1-one;
1H,2,3,3a,4-tetrahydro-8-amino-imidazo[5,1-c][1,4]benzoxazin-1-one;
1H,2,3,3a,4-tetrahydro-8-methyl-imidazo[5,1-c][1,4]benzoxazin-1-one, m.p. 190°-193° C.;
1H,2,3,3a,4-tetrahydro-8-trifluoromethyl-imidazo[5,1-c][1,4]benzoxazin-1-one;
1H,2,3,3a,4-tetrahydro-8-methoxy-imidazo[5,1-c][1,4]benzoxazin-1-one;
1H,2,3,3a,4-tetrahydro-8-carboxy-imidazo[5,1-c][1,4]benzoxazin-1-one;
1H,2,3,3a,4-tetrahydro-8-acetamido-imidazo[5,1-c][1,4]benzoxazin-1-one;
1H,2,3,3a,4-tetrahydro-8-methylsulfonyl-imidazo[5,1-c][1,4]benzoxazin-1-one;
1H,2,3,3a,4-tetrahydro-8-methylsulfonamido-imidazo[5,1-c][1,4]benzoxazin-1-one.

EXAMPLE 5

A mixture of 2H-3,4-dihydro-2-phenyl-3-[N-(3'-dimethylaminopropyl)-aminomethyl]-6-chloro-[1,4]benzoxazine (36 g; $1.10^{-1}$ moles) and urea (7.2 g; $1.2.10^{-2}$ moles) was heated to fusion at 200° C. for 3 hours in an oil bath, then cooled and ground in water. After filtration, the mixture was washed with water and the solid dissolved in ethanol (300 ml); 7% ethanolic HCl was added and after evaporation to dryness and crystallization from dimethylacetamide/water, 1H,2,3,3a,4-tetrahydro-2-(3'-dimethylaminopropyl)-4-phenyl-8-chloro-imidazo[5,1-c][1,4]benzoxazin-1-one hydrochloride (28.5 g) was obtained.

Analogously, the following compounds were obtained:
1H,2,3,3a,4-tetrahydro-2-(3'-dimethylaminopropyl)-4-phenyl-imidazo[5,1-c][1,4]benzoxazin-1-one;
1H,2,3,3a,4-tetrahydro-2-(3'-dimethylaminopropyl)-4-phenyl-8-fluoro-imidazo[5,1-c][1,4]benzoxazin-1-one;
1H,2,3,3a,4-tetrahydro-2-(3'-dimethylaminopropyl)-4-phenyl-8-hydroxy-imidazo[5,1-c][1,4]benzoxazin-1-one;
1H,2,3,3a,4-tetrahydro-2-(3'-dimethylaminopropyl)-4-phenyl-8-amino-imidazo[5,1-c][1,4]benzoxazin-1-one;
1H,2,3,3a,4-tetrahydro-2-(3'-dimethylaminopropyl)-4-phenyl-8-methyl-imidazo[5,1-c][1,4]benzoxazin-1-one;
1H,2,3,3a,4-tetrahydro-2-(3'-dimethylaminopropyl)-4-phenyl-8-trifluoromethyl-imidazo[5,1-c][1,4]benzoxazin-1-one;
1H,2,3,3a,4-tetrahydro-2-(3'-dimethylaminopropyl)-4-phenyl-8-methoxy-imidazo[5,1-c][1,4]benzoxazin-1-one;
1H,2,3,3a,4-tetrahydro-2-(3'-dimethylaminopropyl)-4-phenyl-8-carboxy-imidazo[5,1-c][1,4]benzoxazin-1-one;
1H,2,3,3a,4-tetrahydro-2-(3'-dimethylaminopropyl)-4-phenyl-8-acetamido-imidazo[5,1-c][1,4]benzoxazin-1-one;
1H,2,3,3a,4-tetrahydro-2-(3'-dimethylaminopropyl)-4-phenyl-8-methylsulfonyl-imidazo[5,1-c][1,4]benzoxazin-1-one;
1H,2,3,3a,4-tetrahydro-2-(3'-dimethylaminopropyl)-4-phenyl-8-methylsulfonamido-imidazo[5,1-c][1,4]benzoxazine-1-one.

EXAMPLE 6

A mixture of 2H-3,4-dihydro-3-aminomethyl-[1,4]benzoxazine (1.64 g; $1.10^{-2}$ moles) and urea (1.8 g; $3.10^{-2}$ moles) was heated to fusion for 2 hours at 160° C., then cooled and from the obtained solid ground in water, after filtration and crystallization from ethyl acetate, 1,2,3,3a,4-tetrahydro-2-carbamoyl-imidazo[5,1-c][1,4benzoxazin-1-one (1.65 g; m.p. 243°-246° C.), was obtained.

Analogously, the following compounds were obtained:
1,2,3,3a,4-tetrahydro-2-carbamoyl-8-chloro-imidazo[5,1-c][1,4]benzoxazin-1-one;
1,2,3,3a,4-tetrahydro-2-carbamoyl-8-fluoro-imidazo[5,1-c][1,4]benzoxazin-1-one;

1,2,3,3a,4-tetrahydro-2-carbamoyl-8-methyl-
  imidazo[5,1-c][1,4]benzoxazin-1-one;
1,2,3,3a,4-tetrahydro-2-carbamoyl-8-trifluoromethyl-
  imidazo[5,1-c][1,4]benzoxazin-1-one;
1,2,3,3a,4-tetrahydro-2-carbamoyl-8-methoxy-
  imidazo[5,1-c][1,4]benzoxazin-1-one;
1,2,3,3a,4-tetrahydro-2-carbamoyl-8-carboxy-
  imidazo[5,1-c][1,4]benzoxazin-1-one;
1,2,3,3a,4-tetrahydro-2-carbamoyl-8-acetamido-
  imidazo[5,1-c][1,4]benzoxazin-1-one;
1,2,3,3a,4-tetrahydro-2-carbamoyl-8-methylsulfonyl-
  imidazo[5,1-c][1,4]benzoxazin-1-one;
1,2,3,3a,4-tetrahydro-2-carbamoyl-8-methylsul-
  fonamido-imidazo[5,1-c][1,4]benzoxazin-1-one.

EXAMPLE 7

A mixture of 2H-3,4-dihydro-3-succinimidomethyl-[1,4]benzoxazine (5 g; $2.10^{-2}$ moles) and 37% HCl (50 ml) was kept for 8 hours at the reflux temperature, then cooled; the succinic acid was filtered off, the solution evaporated to dryness and the solid residue was neutralized with 20% sodium hydroxide and extracted with chloroform so obtaining, after drying on $Na_2SO_4$ and evaporation to dryness, 2H-3,4-dihydro-3-aminomethyl-[1,4]benzoxazine (3.1 g; m.p. 83°–86° C.).

Analogously, the following compounds were obtained:
2H-3,4-dihydro-3-aminomethyl-6-chloro-[1,4]benzoxazine, m.p. 50°–52° C.;
2H-3,4-dihydro-3-aminomethyl-6-fluoro-[1,4]benzoxazine;
2H-3,4-dihydro-3-aminomethyl-6-hydroxy-[1,4]benzoxazine,
2H-3,4-dihydro-3-aminomethyl-6-amino-[1,4]benzoxazine;
2H-3,4-dihydro-3-aminomethyl-6-methyl-[1,4]benzoxazine, m.p. 90°–95° C.;
2H-3,4-dihydro-3-aminomethyl-6-trifluoromethyl-[1,4]benzoxazine;
2H-3,4-dihydro-3-aminomethyl-6-methoxy-[1,4]benzoxazine;
2H-3,4-dihydro-3-aminomethyl-6-carboxy-[1,4]benzoxazine;
2H-3,4-dihydro-3-aminomethyl-6-methylsulfonyl-[1,4]benzoxazine.

EXAMPLE 8

A mixture of 2H-3,4-dihydro-2-phenyl-3-[N-(3'-dimethylaminopropyl)-N-trifluoroacetyl)-aminomethyl]-6-chloro[1,4]benzoxazine (3 g; $5.8.10^{-3}$ moles) in methanolic KOH (100 ml) was kept under nitrogen atmosphere for 8 hours at room temperature. The solution was evaporated to dryness, the residue extracted with ethyl ether; after drying on $Na_2SO_4$, evaporation to dryness and crystallization from isopropyl alcohol, 2H-3,4-dihydro-2-phenyl-3-[N-(3'-dimethylaminopropyl)-aminomethyl]-6-chloro[1,4]benzoxazine was obtained.

Analogously, the following compounds were obtained:
2H-3,4-dihydro-2-phenyl-3-methyl-aminomethyl-[1,4]benzoxazine;
2H-3,4-dihydro-2-phenyl-3-carbamoylmethyl-aminomethyl-[1,4]benzoxazine;
2H-3,4-dihydro-2-phenyl-3-(2'-carbamoyl-ethyl)-aminomethyl-[1,4]benzoxazine;
2H-3,4-dihydro-2-phenyl-3-(1'-carbamoyl-ethyl)-aminomethyl-[1,4]benzoxazine;
2H-3,4-dihydro-2-phenyl-3-(1'-methyl-1'-carbamoyl-ethyl)-aminomethyl-[1,4]benzoxazine;
2H-3,4-dihydro-2-phenyl-3-(2'-dimethylaminoethyl)-aminomethyl-[1,4]benzoxazine;
2H-3,4-dihydro-2-phenyl-3-propargyl-aminomethyl-[1,4]benzoxazine;
2H-3,4-dihydro-2-phenyl-3-benzyl-aminomethyl-[1,4]benzoxazine;
2H-3,4-dihydro-2-phenyl-3-(p-methylsulfonyl-benzyl)-aminomethyl-[1,4]benzoxazine;
2H-3,4-dihydro-2-phenyl-3-(3'-t-amylsulfonylpropyl)-aminomethyl-[1,4]benzoxazine;
2H-3,4-dihydro-2-phenyl-3-carbamoylmethyl-aminomethyl-6-chloro-[1,4]benzoxazine;
2H-3,4-dihydro-2-phenyl-3-carbamoylmethyl-aminomethyl-6-fluoro-[1,4]benzoxazine;
2H-3,4-dihydro-2-phenyl-3-carbamoylmethyl-aminomethyl-6-hydroxy-[1,4]benzoxazine;
2H-3,4-dihydro-2-phenyl-3-carbamoylmethyl-aminomethyl-6-amino-[1,4]benzoxazine;
2H-3,4-dihydro-2-phenyl-3-carbamoylmethyl-aminomethyl-6-methyl-[1,4]benzoxazine;
2H-3,4-dihydro-2-phenyl-3-carbamoylmethyl-aminomethyl-6-trifluoromethyl-[1,4]benzoxazine;
2H-3,4-dihydro-2-phenyl-3-carbamoylmethyl-aminomethyl-6-methoxy-[1,4benzoxazine;
2H-3,4-dihydro-2-phenyl-3-carbamoylmethyl-aminomethyl-6-carboxy-[1,4]benzoxazine;
2H-3,4-dihydro-2-phenyl-3-carbamoylmethyl-aminomethyl-6-acetamido-[1,4]benzoxazine;
2H-3,4-dihydro-2-phenyl-3-carbamoylmethyl-aminomethyl-6-methylsulfonyl-[1,4]benzoxazine;
2H-3,4-dihydro-2-phenyl-3-carbamoylmethyl-aminomethyl-6-methylsulfonamido-[1,4]benzoxazine.

EXAMPLE 9

To a solution of 2H-3,4-dihydro-2-phenyl-3-trifluoroacetylaminomethyl-6-chloro-[1,4]benzoxazine (3.71 g; $1.10^{-2}$ moles) in anhydrous dimethylacetamide (50 ml), 50% NaH (0.58 g; $1.10^{-2}$ moles) was added slowly and under stirring at room temperature. After stirring for 30 minutes, 1-chloro-3-dimethylaminopropane (1.5 g) was added at room temperature; the mixture was heated at 60° C. for 6 hours, then poured in water and extracted with ethyl ether. After washing with water, evaporation to dryness, an oil remained which was dissolved in ethyl acetate. By treatment with methanolic HCl 2H-3,4-dihydro-2-phenyl-3-[N-trifluoroacetyl)-N-(3'-dimethylaminopropyl)-aminomethyl]-6-chloro-[1,4]benzoxazine hydrochloride (3.2 g) precipitated.

Analogously, the following compounds were obtained:
2H-3,4-dihydro-2-phenyl-3-[N-(trifluoroacetyl)-N-methyl-aminomethyl]-[1,4]benzoxazine;
2H-3,4-dihydro-2-phenyl-3-[N-(trifluoroacetyl)-N-carbamoylmethyl-aminomethyl]-[1,4]benzoxazine;
2H-3,4-dihydro-2-phenyl-3-[N-(trifluoroacetyl)-N-(2'-carbamoyl-ethyl)-aminomethyl]-[1,4]benzoxazine;
2H-3,4-dihydro-2-phenyl-3-[N-(trifluoroacetyl)-N-(1'-carbamoyl-ethyl)-aminomethyl]-[1,4]benzoxazine;
2H-3,4-dihydro-2-phenyl-3-[N-(trifluoroacetyl)-N-(1'-methyl-1'-carbamoyl-ethyl)-aminomethyl]-[1,4]benzoxazine;
2H-3,4-dihydro-2-phenyl-3-[N-(trifluoroacetyl)-N-(2'-dimethylaminoethyl)-aminomethyl]-[1,4]benzoxazine;

2H-3,4-dihydro-2-phenyl-3-[N-(trifluoroacetyl)-N-(3'-dimethylaminopropyl)-aminomethyl]-[1,4benzoxazine;

2H-3,4-dihydro-2-phenyl-3-[N-(trifluoroacetyl)-N-propargyl-aminomethyl]-[1,4]benzoxazine;

2H-3,4-dihydro-2-phenyl-3-[N-(trifluoroacetyl)-N-benzyl-aminomethyl]-[1,4]benzoxazine;

2H-3,4-dihydro-2-phenyl-3-[N-(trifluoroactyl)-N-(p-methylsulfonyl-benzyl)-aminomethyl]-[1,4]benzoxazine;

2H-3,4-dihydro-2-phenyl-3-[N-(trifluoroacetyl)-N-(3'-t-amylsulfonylpropyl)-aminomethyl]-[1,4]benzoxazine;

2H-3,4-dihydro-2-phenyl-3-[N-(trifluoroacetyl)-N-carbamoylmethyl-aminomethyl]-6-chloro-[1,4]benzoxazine;

2H-3,4-dihydro-2-phenyl-3-[N-(trifluoroacetyl)-N-carbamoylmethyl-aminomethyl]-6-fluoro-[1,4]benzoxazine;

2H-3,4-dihydro-2-phenyl-3-[N-(trifluoroacetyl)-N-carbamoylmethyl-aminomethyl]-6-hydroxy-[1,4]benzoxazine;

2H-3,4-dihydro-2-phenyl-3-[N-(trifluoroacetyl)-N-carbamoylmethyl-aminomethyl]-6-amino-[1,4]benzoxazine;

2H-3,4-dihydro-2-phenyl-3-[N-(trifluoroacetyl)-N-carbamoylmethyl-aminomethyl]-6-methyl-[1,4]benzoxazine;

2H-3,4-dihydro-2-phenyl-3-[N-(trifluoroacetyl)-N-carbamoylmethyl-aminomethyl]-6-trifluoromethyl-[1,4]benzoxazine;

2H-3,4-dihydro-2-phenyl-3-[N-(trifluoroacetyl)-N-carbamoylmethyl-aminomethyl]-6-methoxy-[1,4]benzoxazine;

2H-3,4-dihydro-2-phenyl-3-[N-(trifluoroacetyl)-N-carbamoylmethyl-aminomethyl]-6-carboxy-[1,4]benzoxazine;

2H-3,4-dihydro-2-phenyl3-[N-(trifluoroacetyl)-N-carbamoylmethyl-aminomethyl]-6-acetamido-[1,4]benzoxazine;

2H-3,4-dihydro-2-phenyl-3-[N-(trifluoroacetyl)-N-carbamoylmethyl-aminomethyl]-6-methylsulfonyl-[1,4]benzoxazine;

2H-3,4-dihydro-2-phenyl-3-[N-(trifluoroacetyl)-N-carbamoylmethyl-aminomethyl]-6-methylsulfonamido-[1,4]benzoxazine.

EXAMPLE 10

To a stirred solution, cooled at $-30°$ C., of 2H-3,4-dihydro-3-aminomethyl-[1,4]benzoxazine (16.4 g; $1.10^{-1}$ moles) in $CH_2Cl_2$ (100 ml) and $Et_3N$ (14 g; $1.5.10^{-1}$ moles), a solution of trifluoroacetic anhydride (21 g) in $CH_2Cl_2$ was added dropwise. After 1 hour at $-30°$ C. the solution was allowed to reach the room temperature, then washed with 5% $NaHCO_3$ and water; by evaporation to dryness,
2H-3,4-dihydro-3-trifluoroacetylaminomethyl-[1,4]benzoxazine was obtained (18.1 g).

Analogously, the following compounds were obtained:

2H-3,4-dihydro-3-trifluoroacetylaminomethyl-6-chloro-[1,4]benzoxazine;

2H-3,4-dihydro-3-trifluoroacetylaminomethyl-6-fluoro-[1,4]benzoxazine;

2H-3,4-dihydro-3-trifluoroacetylaminomethyl-6-hydroxy-[1,4]benzoxazine;

2H-3,4-dihydro-3-trifluoroacetylaminomethyl-6-amino-[1,4]benzoxazine;

2H-3,4-dihydro-3-trifluoroacetylaminomethyl-6-methyl-[1,4]benzoxazine;

2H-3,4-dihydro-3-trifluoroacetylaminomethyl-6-trifluoromethyl-[1,4]benzoxazine;

2H-3,4-dihydro-3-trifluoroacetylaminomethyl-6-methoxy-[1,4]benzoxazine;

2H-3,4-dihydro-3-trifluoroacetylaminomethyl-6-carboxy-[1,4]benzoxazine;

2H-3,4-dihydro-3-trifluoroacetylaminomethyl-6-acetamido-[1,4]benzoxazine;

2H-3,4-dihydro-3-trifluoroacetylaminomethyl-6-methylsulfonyl-[1,4]benzoxazine;

2H-3,4-dihydro-3-trifluoroacetylaminomethyl-6-methylsulfonamido-[1,4]benzoxazine.

EXAMPLE 11

To a solution of 1H,2,3,3a,4-tetrahydro-1,1-dimethyl-8-chloro-imidazo[5,1-c][1,4]benxoxazine (4.8 g; $2.10^{-2}$ moles) in anhydrous dimethylacetamide (60 ml), potassium carbonate (4.6 g; $3.33.10^{-2}$ moles) was added and to the resulting suspension, methyl iodide (2.85 g; $2.10^{-2}$ moles) was added dropwise under stirring. The mixture was kept to 80° C. for 24 hours then poured in water and extracted with ethyl ether.

By evaporation to dryness an oily residue was obtained which, after elution on a silica gel column with benzene: acetone-diethylamine (150:50:2) gave 1H,2,3,3a,4-tetrahydro-1,1,2-trimethyl-8-chloro-imidazo[5,1-c][1,4]benzoxazine (2.3 g).

Analogously, the following compounds were obtained:

1H,2,3,3a,4-tetrahydro-1,1,2-trimethyl-imidazo[5,1-c][1,4]benzoxazine;

1H,2,3,3a,4-tetrahydro-1,1-dimethyl-2-carbamoylmethyl-imidazo[5,1-c][1,4]benzoxazine;

1H,2,3,3a,4-tetrahydro-1,1-dimethyl-2-(2'-carbamoylethyl)-imidazo[5,1-c[[1,4]benzoxazine;

1H,2,3,3a,4-tetrahydro-1,1-dimethyl-2-(1'-carbamoylethyl)-imidazo[5,1-c][1,4]benzoxazine;

1H,2,3,3a,4-tetrahydro-1,1-dimethyl-2-(1'-methyl-1'-carbamoyl-ethyl)-imidazo[5,1-c][1,4]benzoxazine;

1H,2,3,3a,4-tetrahydro-1,1-dimethyl-2-(2'-dimethylaminoethyl)-imidazo[5,1-c][1,4]benzoxazine;

1H,2,3,3a,4-tetrahydro-1,1-dimethyl-2-(3'-dimethylamiopropyl)-imidazo[5,1-c][1,4]benzoxazine;

1H,2,3,3a,4-tetrahydro-1,1-dimethyl-2-propargyl-imidazo[5,1-c][1,4]benzoxazine;

1H,2,3,3a,4-tetrahydro-1,1-dimethyl-2-benzyl-imidazo[5,1-c][1,4]benzoxazine;

1H,2,3,3a,4-tetrahydro-1,1-dimethyl-2-(p-methylsulfonylbenzyl)-imidazo[5,1-c][1,4]benzoxazine;

1H,2,3,3a,4-tetrahydro-1,1-dimethyl-2-(3'-t-amylsulfonylpropyl)-imidazo[5,1-c][1,4]benzoxazine;

1H,2,3,3a,4-tetrahydro-1,1-dimethyl-2-carbamoylmethyl-8-chloro-imidazo[5,1-c][1,4]benzoxazine;

1H,2,3,3a,4-tetrahydro-1,1-dimethyl-2-carbamoylmethyl-8-fluoro-imidazo[5,1-c][1,4]benzoxazine;

1H,2,3,3a;4-tetrahydro-1;1-dimethyl-2-carbamoylmethyl-8-hydroxy-imidazo[5;1-c][1;4]benzaxazine;

1H,2,3,3a,4-tetrahydro-1,1-dimethyl-2-carbamoylmethyl-8-amino-imidazo[5,1-c][1,4]benzoxazine;

1H,2,3,3a,4-tetrahydro-1,1-dimethyl-2-carbamoylmethyl-8-methyl-imidazo[5,1-c][1,4]benzoxazine;

1H,2,3,3a,4-tetrahydro-1,1-dimethyl-2-carbamoylmethyl-8-trifluoromethyl-imidazo[5,1-c][1,4]benzoxazine;

1H,2,3,3a,4-tetrahydro-1,1-dimethyl-2-carbamoylmethyl-8-methoxy-imidazo[5,1-c][1,4]benzoxazine;

1H,2,3,3a,4-tetrahydro-1,1-dimethyl-2-carbamoylmethyl-8-carboxy-imidazo[5,1-c][1,4]benzoxazine;
1H,2,3,3a,4-tetrahydro-1,1-dimethyl-2-carbamoylmethyl-8-acetamido-imidazo[5,1-c][1,4]benzoxazine;
1H,2,3,3a,4-tetrahydro-1,1-dimethyl-2-carbamoylmethyl-8-methylsulfonyl-imidazo[5,1-c][1,4]benzoxazine;
1H,2,3,3a,4-tetrahydro-1,1-dimethyl-2-carbamoylmethyl-8-methylsulfonamido-imidazo[5,1-c][1,4]benzoxazine.

EXAMPLE 12

A solution of 2H-3,4-dihydro-3-aminomethyl-6-chloro-[1,4]benzoxazine (1.99 g; $1.10^{-2}$ moles) and acetone (1 ml) in benzene (150 ml) and p-toluenesolphonic acid (0.01 g) was refluxed for 18 hours, by removing the water with a Dean-Stark apparatus. The resulting solution was cooled, washed with a NaHCO$_3$ diluted solution, then with water, dried on magnesium sulphate and evaporated under vacuum. The solid residue was crystallized from ethyl acetate so obtaining 1H,2,3,3a,4-tetrahydro-1,1-dimethyl-8-chloro-imidazo[5,1-c][1,4]benzoxazine (0.9 g).

Analogously, the following compounds were obtained:
1H,2,3,3a,4-tetrahydro-1,1-dimethyl-imidazo[5,1-c][1,4]benzoxazine;
1H,2,3,3a,4-tetrahydro-1,1-dimethyl-8-fluoro-imidazo[5,1-c][1,4]benzoxazine;
1H,2,3,3a,4-tetrahydro-1,1-dimethyl-8-hydroxy-imidazo[5,1-c][1,4]benzoxazine;
1H,2,3,3a,4-tetrahydro-1,1-dimethyl-8-methyl-imidazo[5,1-c][1,4]benzoxazine;
1H,2,3,3a,4-tetrahydro-1,1-dimethyl-8-trifluoromethyl-imidazo[5,1-c][1,4]benzoxazine;
1H,2,3,3a,4-tetrahydro-1,1-dimethyl-8-methoxy-imidazo[5,1-c][1,4]benzoxazine;
1H,2,3,3a,4-tetrahydro-1,1-dimethyl-8-carboxy-imidazo[5,1-c][1,4]benzoxazine;
1H,2,3,3a,4-tetrahydro-1,1-dimethyl-8-acetamido-imidazo[5,1-c][1,4]benzoxazine;
1H,2,3,3a,4-tetrahydro-1,1-dimethyl-8-methylsulfonyl-imidazo[5,1-c][1,4]benzoxazine;
1H,2,3,3a,4-tetrahydro-1,1-dimethyl-8-methylsulfonamido-imidazo[5,1-c][1,4]benzoxazine.

EXAMPLE 13

To a solution of 1H,2,3,3a,4-tetrahydro-4-phenyl-imidazo[5,1-c][1,4]benzoxazin-1-one (2.5 g; $1.10^{-2}$ moles) in anhydrous dimethylacetamide (50 ml), 50% sodium hydride (0.55 g; $1.1.10^{-2}$ moles) was added and, under stirring, heated at 50° C. for 30 minutes. The solution was then brought to room temperature and chloroacetamide (0.95 g; $1.05.10^{-2}$ moles) dissolved in anhydrous dimethylacetamide (10 ml) was added dropwise. The mixture was heated for 1 hour at 60° C., poured in water and extracted with ethyl acetate. The resulting solution was dried on Na$_2$SO$_4$ and concentrated so obtaining a solid which, after crystallization from dimethylacetamide/water gave 1H,2,3,3a,4-tetrahydro-2-carbamoylmethyl-4-phenyl-imidazo[5,1-c][1,4]benzoxazin-1-one (1.5 g).

Analogously, the following compounds were obtained:
1H,2,3,3a,4-tetrahydro-2-carbamoylmethyl-4-methyl-4-phenyl-imidazo[5,1-c][1,4]benzoxazin-1-one;
1H,2,3,3a,4-tetrahydro-2-(2'-carbamoyl-ethyl)-4-phenyl-imidazo[5,1-c][1,4]benzoxazin-1-one;
1H,2,3,3a,4-tetrahydro-2-(1'-carbamoyl-ethyl)-4-phenyl-imidazo[5,1-c][1,4]benzoxazin-1-one;
1H,2,3,3a,4-tetrahydro-2-(1'-methyl-1'-carbamoyl-ethyl)-4-phenyl-imidazo[5,1-c][1,4]benzoxazin-1-one;
1H,2,3,3a,4-tetrahydro-2-(2'-dimethylaminoethyl)-4-phenyl-imidazo[5,1-c][1,4]benzoxazin-1-one;
1H,2,3,3a,4-tetrahydro-2-(3'-dimethylaminopropyl)-4-phenyl-imidazo[5,1-c][1,4]benzoxazin-1-one;
1H,2,3,3a,4-tetrahydro-2-propargyl-4-phenyl-imidazo[5,1-c][1,4]benzoxazin-1-one;
1H,2,3,3a,4-tetrahydro-2-benzyl-4-phenyl-imidazo[5,1-c][1,4]benzoxazin-1-one;
1H,2,3,3a,4-tetrahydro-2-(p-methylsulfonyl-benzyl)-4-phenyl-imidazo[5,1-c][1,4]benzoxazin-1-one;
1H,2,3,3a,4-tetrahydro-2-(3'-t-amylsulfonylpropyl)-4-phenyl-imidazo[5,1-c][1,4]benzoxazin-1-one;
1H,2,3,3a,4-tetrahydro-2-carbamoylmethyl-4-phenyl-8-chloro-imidazo[5,1-c][1,4]benzoxazin-1-one;
1H,2,3,3a,4-tetrahydro-2-carbamoylmethyl-4-phenyl-8-fluoro-imidazo[5,1-c][1,4]benzoxazin-1-one;
1H,2,3,3a,4-tetrahydro-2-carbamoylmethyl-4-phenyl-8-hydroxy-imidazo[5,1-c][1,4]benzoxazin-1-one;
1H,2,3,3a,4-tetrahydro-2-carbamoylmethyl-4-phenyl-8-amino-imidazo[5,1-c][1,4]benzoxazin-1-one;
1H,2,3,3a,4-tetrahydro-2-carbamoylmethyl-4-phenyl-8-methyl-imidazo[5,1-c][1,4]benzoxazin-1-one;
1H,2,3,3a,4-tetrahydro-2-carbamoylmethyl-4-phenyl-8-trifluoromethyl-imidazo[5,1-c][1,4]benzoxazin-1-one;
1H,2,3,3a,4-tetrahydro-2-carbamoylmethyl-4-phenyl-8-methoxy-imidazo[5,1-c][1,4]benzoxazin-1-one;
1H,2,3,3a,4-tetrahydro-2-carbamoylmethyl-4-phenyl-8-carboxy-imidazo[5,1-c][1,4]benzoxazin-1-one;
1H,2,3,3a,4-tetrahydro-2-carbamoylmethyl-4-phenyl-8-acetamido-imidazo[5,1-c][1,4]benzoxazin-1-one;
1H,2,3,3a,4-tetrahydro-2-carbamoylmethyl-4-phenyl-8-methylsulfonyl-imidazo[5,1-c][1,4]benzoxazin-1-one;
1H,2,3,3a,4-tetrahydro-2-carbamoylmethyl-4-phenyl-8-methylsulfonamido-imidazo[5,1-c][1,4]benzoxazin-1-one;
1H,2,3,3a,4-tetrahydro-2-carbamoylmethyl-4-methyl-4-(2'-methoxyphenyl)-imidazo[5,1-c][1,4]benzoxazin-1-one;
1H,2,3,3a,4-tetrahydro-2-carbamoylmethyl-4-(2'-methoxy-phenyl)-imidazo[5,1-c][1,4]benzoxazin-1-one;
1H,2,3,3a,4-tetrahydro-2-(2'-carbamoyl-ethyl)-4-(2'-methoxy-phenl)-imidazo[5,1-c][1,4]benzoxazin-1-one;
1H,2,3,3a,4-tetrahydro-2-(1'-carbamoyl-ethyl)-4-(2'-methoxy-phenyl)-imidazo[1,5-c][1,4]benzoxazin-1-one;
1H,2,3,3a,4-tetrahydro-2-(1'-methyl-1'-carbamoyl-ethyl)-4-(2'-methoxy-phenyl)-imidazo[5,1-c][1,4]benzoxazin-1-one;
1H,2,3,3a,4-tetrahydro-2-carbamoylmethyl-4-methyl-4-(4'-chlorophenyl)-imidazo[5,1-c][1,4]benzoxazin-1-one;
1H,2,3,3a,4-tetrahydro-2-carbamoylmethyl-4-(4'-chloro-phenyl)-imidazo[5,1-c][1,4]benzoxazin-1-one;
1H,2,3,3a,4-tetrahydro-2-(2'-carbamoyl-ethyl)-4-(4'-chloro-phenyl)-imidazo[5,1-c][1,4]benzoxazin-1-one;
1H,2,3,3a,4-tetrahydro-2-(1'-carbamoyl-ethyl)-4-(4'-chloro-phenyl)-imidazo[5,1-c][1,4]benzoxazin-1-one;
1H,2,3,3a,4-tetrahydro-2-(1'-methyl-1'-carbamoyl-ethyl)-4-(4'-chloro-phenyl)-imidazo[5,1-c][1,4]benzoxazin-1-one.

EXAMPLE 14

By proceeding as described in example 3, starting from 2H-3,4-dihydro-2-phenyl-3-aminomethyl-[1,4]benzoxazine (24 g; $1.10^{-1}$ moles) and urea (7.2 g; $1.2.10^{-1}$ moles), 1H,2,3,3a,4-tetrahydro-4-phenyl-imidazo[5,1-c][1,4]benzoxazin-1-one (17.6 g), (crystallization from isopropyl alcohol) was obtained.

Analogously, the following compounds were obtained:
1H,2,3,3a,4-tetrahydro-4-methyl-4-phenyl-imidazo[5,1-c][1,4]benzoxazin-1-one;
1H,2,3,3a,4-tetrahydro-4-phenyl-8-chloro-imidazo[5,1-c][1,4]benzoxazin-1-one;
1H,2,3,3a,4-tetrahydro-4-phenyl-8-fluoro-imidazo[5,1-c][1,4]benzoxazin-1-one;
1H,2,3,3a,4-tetrahydro-4-phenyl-8-hydroxy-imidazo[5,1-c][1,4]benzoxazin-1-one;
1H,2,3,3a,4-tetrahydro-4-phenyl-8-amino-imidazo[5,1-c][1,4]benzoxazin-1-one;
1H,2,3,3a,4-tetrahydro-4-phenyl-8-methyl-imidazo[5,1-c][1,4]benzoxazin-1-one;
1H,2,3,3a,4-tetrahydro-4-phenyl-8-trifluoromethyl-imidazo[5,1-c][1,4]benzoxazin-1-one;
1H,2,3,3a,4-tetrahydro-4-phenyl-8-methoxy-imidazo[5,1-c][1,4]benzoxazin-1-one;
1H,2,3,3a,4-tetrahydro-4-phenyl-8-carboxy-imidazo[5,1-c][1,4]benzoxazin-1-one;
1H,2,3,3a,4-tetrahydro-4-phenyl-8-acetamido-imidazo[5,1-c][1,4]benzoxazin-1-one;
1H,2,3,3a,4-tetrahydro-4-phenyl-8-methylsulfonyl-imidazo[5,1-c][1,4]benzoxazin-1-one;
1H,2,3,3a,4-tetrahydro-4-phenyl-8-methylsulfonamido-imidazo[5,1-c][1,4]benzoxazin-1-one;
1H,2,3,3a,4-tetrahydro-4-(2'-methoxy-phenyl)-imidazo[5,1-c][1,4]benzoxazin-1-one;
1H,2,3,3a,4-tetrahydro-4-methyl-4-(2'-methoxy-phenyl)-imidazo[5,1-c][1,4]benzoxazin-1-one;
1H,2,3,3a,4-tetrahydro-4-(4'-chloro-phenyl)-imidazo[5,1-c][1,4]benzoxazin-1-one;
1H,2,3,3a,4-tetrahydro-4-methyl-4-(4'-chloro-phenyl)-imidazo[5,1-c][1,4]benzoxazine.

EXAMPLE 15

A solution of 2H-2-phenyl-[1,4]benzoxazine (60 g; 0.277 moles), $Na_2S_2O_5$ (52.7 g; 0.27 moles) and KCN (55.5 g; 0.84 moles) was stirred in dimethylformamide (1000 ml) and water (200 ml) for 70 hours at room temperature, then poured in water and extracted with $CHCl_3$; the extracts were washed with diluted NaOH then with water. After evaporation to dryness the obtained solid residue was ground in benzene so obtaining 2H-3,4-dihydro-3-cyano-2-phenyl-[1,4]benzoxazine (41.6 g).

Analogously, the following compounds were obtained:
2H-3,4-dihydro-3-cyano-2-phenyl-6-chloro-[1,4]benzoxazine;
2H-3,4-dihydro-3-cyano-2-phenyl-6-fluoro-[1,4]benzoxazine;
2H-3,4-dihydro-3-cyano-2phenyl-6-hydroxy-[1,4]benzoxazine;
2H-3,4-dihydro-3-cyano-2-phenyl-6-amino-[1,4]benzoxazine;
2H-3,4-dihydro-3-cyano-2-phenyl-6-methyl-[1,4]benzoxazine;
2H-3,4-dihydro-3-cyano-2-phenyl-6-trifluoromethyl-[1,4]benzoxazine;
2H-3,4-dihydro-3-cyano-2-phenyl-6-methoxy-[1,4]benzoxazine;
2H-3,4-dihydro-3-cyano-2-phenyl-6-carboxy-[1,4]benzoxazine;
2H-3,4-dihydro-3-cyano-2-phenyl-6-acetamido-[1,4]benzoxazine;
2H-3,4-dihydro-3-cyano-2-phenyl-6-methylsulfonyl-[1,4]benzoxazine;
2H-3,4-dihydro-3-cyano-2-phenyl-6-methylsulfonamido-[1,4]benzoxazine;
2H-3,4-dihydro-3-cyano-2-(2'-methoxy-phenyl)-[1,4]benzoxazine;
2H-3,4-dihydro-3-cyano-2-methyl-2-(2'-methoxy-phenyl)-[1,4]benzoxazine;
2H-3,4-dihydro-3-cyano-2-(4'-chloro-phenyl)-[1,4]benzoxazine;
2H-3,4-dihydro-3-cyano-2-methyl-2-(4'-chloro-phenyl)-[1,4]benzoxazine.

EXAMPLE 16

A solution of 1-phenyl-1-(o-nitrophenoxy)-acetyl chloride (10 g; $3.43.10^{-2}$ moles) was dissolved in anhydrous toluene (50 ml), then 5% $Pd/BaSO_4$ (1.5 g) was added and the solution refluxed for 6 hours while a stream of hydrogen was bubbled into the solution until the HCl development was terminated. The catalyst was removed, the toluene was distilled under reduced pressure so obtaining 2H-2-phenyl-[1,4]benzoxazine (5.5 g) by crystallization from isopropyl alcohol.

Analogously, the following compounds were obtained:
2H-2-phenyl-6-fluoro-[1,4]benzoxazine;
2H-2-phenyl-6-hydroxy-[1,4]benzoxazine;
2H-2-phenyl-6-methyl-[1,4]benzoxazine;
2H-2-phenyl-6-trifluoromethyl-[1,4]benzoxazine;
2H-2-phenyl-6-methoxy-[1,4]benzoxazine;
2H-2-phenyl-6-acetamido-[1,4]benzoxazine;
2H-2-phenyl-6-methylsulfonyl-[1,4]benzoxazine;
2H-2-phenyl-6-methylsulfonamido-[1,4]benzoxazine;
2H-2-(2'-methoxy-phenyl)-[1,4]benzoxazine;
2H-2-methyl-2-(2'-methoxy-phenyl)-[1,4]benzoxazine;
2H-2-(4'-chloro-phenyl)-[1,4]benzoxazine;
2H-2-methyl-2-(4'-chloro-phenyl)-[1,4]benzoxazine.

EXAMPLE 17

To a mixture of 1-phenyl-1-(o-nitrophenoxy)-acetic acid (30 g; $1.09.10^{-1}$ moles), $SOCl_2$ (200 ml) was added and the mixture refluxed for 30 minutes. After evaporation to dryness, the solution was taken up twice with toluene, decolourized and evaporated to dryness. By grinding the resulting solid in petroleum ether, 1-phenyl-1-(o-nitrophenoxy)-acetyl chloride (28.0 g) was obtained, m.p. 61°–63° C.

Analogously, the following compounds were obtained:
1-phenyl-1-(4'-chloro-o-nitrophenoxy)-acetyl chloride;
1-phenyl-1-(4'-fluoro-o-nitrophenoxy)-acetyl chloride;
1-phenyl-1-(4'-methyl-o-nitrophenoxy)-acetyl chloride;
1-phenyl-1-(4'-trifluoromethyl-o-nitrophenoxy)-acetyl chloride;
1-phenyl-1-(4'-methoxy-o-nitrophenoxy)-acetyl chloride;
1-phenyl-1-(4'-carbethoxy-o-nitrophenoxy)-acetyl chloride;
1-phenyl-1-(4'-acetamido-o-nitrophenoxy)-acetyl chloride;
1-phenyl-1-(4'-methylsulfonyl-o-nitrophenoxy)-acetyl chloride;

1-(2'-methoxy-phenyl)-1-(o-nitrophenoxy)-acetyl chloride;
1-(4'-chloro-phenyl)-1-(o-nitrophenoxy)-acetyl chloride;
1-phenyl-1-(o-nitrophenoxy)-propionyl chloride;
1-phenyl-1-(4'-chloro-o-nitrophenoxy)-propionyl chloride;
1-phenyl-1-(4'-fluoro-o-nitrophenoxy)-propionyl chloride;
1-phenyl-1-(4'-methyl-o-nitrophenoxy)-propionyl chloride;
1-phenyl-1-(4'-trifluoromethyl-o-nitrophenoxy)-propionyl chloride;
1-phenyl-1-(4'-methoxy-o-nitrophenoxy)-propionyl chloride;
1-phennyl-1-(4'-carbethoxy-o-nitrophenoxy)-propionyl chloride;
1-phenyl-1-(4'-acetamido-o-nitrophenoxy)-propionyl chloride;
1-phenyl-1-(4'-methylsulfonyl-o-nitrophenoxy)-propionyl chloride;
1-(2'-methoxy-phenyl)-1-(o-nitrophenoxy)-propionyl chloride;
1-(4'-chloro-phenyl)-1-(o-nitrophenoxy)-propionyl chloride.

EXAMPLE 18

A solution of ethyl 1-phenyl-1-(o-nitrophenoxy)-acetate (452 g; 1.5 moles) in acetic acid (1.5 l) and water (600 ml) was refluxed for 60 hours. After evaporation to dryness, the solution was taken up twice with toluene and every time evaporated to dryness. The residue was dissolved in ethyl ether and extracted with 5% NaHCO$_3$. The basic extract was at once acidified with 23% HCl, extracted again with ethyl ether, repeatedly washed with water, then dried on Na$_2$SO$_4$, decolourized and evaporated to dryness. The resulting oily residue solidified by vigorously stirring with water; after filtration and washing with water, the dried solid was ground in pentane so obtaining 1-phenyl-1-(o-nitrophenoxy)-acetic acid (275 g; m.p. 94°–97° C.).

Analogously, the following compounds were obtained:
1-phenyl-1-(4'-chloro-o-nitrophenoxy)-acetic;
1-phenyl-1-(4'-fluoro-o-nitrophenoxy)-acetic;
1-phenyl-1-(4'-hydroxy-o-nitrophenoxy)-acetic;
1-phenyl-1-(4'-amino-o-nitrophenoxy)-acetic;
1-phenyl-1-(4'-methyl-o-nitrophenoxy)-acetic;
1-phenyl-1-(4'-trifluoromethyl-o-nitrophenoxy)-acetic;
1-phenyl-1-(4'-methoxy-o-nitrophenoxy)-acetic;
1-phenyl-1-(4'-carboxy-o-nitrophenoxy)-acetic;
1-phenyl-1-(4'-acetamido-o-nitrophenoxy)-acetic;
1-phenyl-1-(4'-methylsulfonyl-o-nitrophenoxy)-acetic.

EXAMPLE 19

To a solution of sodium o-nitrophenate (322 g; 2 moles) in anhydrous dimethylacetamide, ethyl 1-chloro-1-phenyl-acetate (398 g; 2 moles) was added dropwise under a nitrogen steam. The mixture was heated at 70° C. for 45 minutes, then ethyl 1-chloro-1-phenyl-acetate was added (39.8 g), keeping the temperature at 70° C. for 45 minutes: the resulting solution was cooled, poured in water and ice and extracted with ethyl ether. By evaporation of the ether an oil was obtained which solidified by treatment with pentane to give ethyl 1-phenyl-1-(o-nitrophenoxy)-acetate, (324 g; m.p. 59°–61° C.).

Analogously, the following compounds were obtained:
ethyl 1-phenyl-1-(4'-chloro-o-nitrophenoxy)-acetate;
ethyl 1-phenyl-1-(4'-fluoro-o-nitrophenoxy)-acetate;
ethyl 1-phenyl-1-(4'-amino-o-nitrophenoxy)-acetate;
ethyl 1-phenyl-1-(4'-methyl-o-nitrophenoxy)-acetate;
ethyl 1-phenyl-1-(4'-trifluoromethyl-o-nitrophenoxy)-acetate;
ethyl 1-phenyl-1-(4'-methoxy-o-nitrophenoxy)-acetate;
ethyl 1-phenyl-1-(4'-carboxy-o-nitrophenoxy)-acetate;
ethyl 1-phenyl-1-(4'-acetamido-o-nitropheoxy)-acetate;
ethyl 1-phenyl-1-(4'-methylsulfonyl-o-nitrophenoxy)-acetate;
ethyl 1-phenyl-1-(4'-methylsulfonamido-o-nitrophenoxy)-acetate.

EXAMPLE 20

A solution of ethyl 1-phenyl-1-(o-nitrophenoxy)-acetate (20 g; $0.6.10^{-2}$ moles) and methyl iodide (31 ml; $5.10^{-1}$ moles) was dissolved in dimethylformamide (40 ml) under a nitrogen steam. To this solution NaH (19.2 g) was added portionwise at −10° C. After the addition, the mixture was allowed to reach the room temperature and kept to this temperature for 2 hours then, after evaporation to dryness under vacuum, dilution with water and extraction with ethyl ether, the ethereal solution was washed throughly with water, dried on Na$_2$SO$_4$ and evaporated to dryness. By grinding in pentane, the residue oil solidified to give ethyl 1-phenyl-1-(o-nitrophenoxy)-propionate (17.3 g).

Analogously, the following compounds were obtained:
ethyl 1-phenyl-1-(4'-chloro-n-nitrophenoxy)-propionate;
ethyl 1-phenyl-1-(4'-fluoro-o-nitrophenoxy)-propionate;
ethyl 1-phenyl-1-(4'-amino-o-nitrophenoxy)-propionate;
ethyl 1-phenyl-1-(4'-methyl-o-nitrophenoxy)-propionate;
ethyl 1-phenyl-1-(4'-trifluoromethyl-o-nitrophenoxy)-propionate;
ethyl 1-phenyl-1-(4'-methoxy-o-nitrophenoxy)-propionate;
ethyl 1-phenyl-1-(4'-carboxy-o-nitrophenoxy)-propionate;
ethyl 1-phenyl-1-(4'-acetamido-o-nitrophenoxy)-propionate;
ethyl 1-phenyl-1-(4'-methylsulfonyl-o-nitrophenoxy)-propionate;
ethyl 1-phenyl-1-(4'-methylsulfonamido-o-nitrophenoxy)-propionate;
ethyl 1-(2'-methoxyphenyl)-1-(o-nitrophenoxy)-propionate;
ethyl 1-(4'-chlorophenyl)-1-(o-nitrophenoxy)-propionate.

EXAMPLE 21

Starting from 1H,2,3,3a,4-tetrahydro-3a-phenyl-imidazo [5,1-c][1,4]benzoxazin-1-one (2.66 g; $1.10^{-2}$ moles) and working as described in example 1, 1H,2,3,3a,4-tetrahydro-2-carbamoylmethyl-3a-phenyl-imidazo[5,1-c][1,4]benzoxazin-1-one (2.1 g; m.p. 207°–209° C.), was obtained by crystallization from 99% EtOH.

Analogously, the following compounds were obtained:

1H,2,3,3a,4-tetrahydro-2-methyl-3a-phenyl-imidazo[5,1-c][1,4]benzoxazin-1-one;

1H,2,3,3a,4-tetrahydro-2-(2'-carbamoyl-ethyl)-3a-phenyl-imidazo[5,1-c][1,4]benzoxazin-1-one;

1H,2,3,3a,4-tetrahydro-2-(1'-carbamoyl-ethyl)-3a-phenyl-imidazo[5,1-c][1,4]benzoxazin-1-one;

1H,2,3,3a,4-tetrahydro-2-(1'-methyl-1'-carbamoyl-ethyl)-3a-phenyl-imidazo[5,1-c][1,4]benzoxazin-1-one;

1H,2,3,3a,4-tetrahydro-2-(2'-dimethylaminoethyl)-3a-phenyl-imidazo[5,1-c][1,4]benzoxazin-1-one;

1H,2,3,3a,4-tetrahydro-2-(3'-dimethylaminopropyl)-3a-phenyl-imidazo[5,1-c][1,4]benzoxazin-1-one;

1H,2,3,3a,4-tetrahydro-2-propargyl-3a-phenyl-imidazo[5,1-c][benzoxazin-1-one];

1H,2,3,3a,4-tetrahydro-2-benzyl-3a-phenyl-imidazo[5,1-c][1,4]-benzoxazin-1-one;

1H,2,3,3a,4-tetrahydro-2-(p-methylsulfonyl-benzyl)-3a-phenyl-imidazo[5,1c][1,4]benzoxazin-1-one;

1H,2,3,3a,4-tetrahydro-2-(3'-t-amylsulfonylpropyl)-3a-phenyl-imidazo[5,1-c][1,4]benzoxazin-1-one;

1-H,2,3,3a,4-tetrahydro-2-carbamoylmethyl-3a-phenyl-8-chloro-imidazo[5,1-c][1,4]benzoxazin-1-one;

1H,2,3,3a,4-tetrahydro-2-carbamoylmethyl-3a-phenyl-8-fluoro-imidazo[5,1-c][1,4]benzoxazin-1-one;

1H,2,3,3a,4-tetrahydro-2-carbamoylmethyl-3a-phenyl-8-hydroxy-imidazo[5,1-c][1,4]benzoxazin-1-one;

1H,2,3,3a,4-tetrahydro-2-carbamoylmethyl-3a-phenyl-8-amino-imidazo[5,1-c][1,4]benzoxazin-1-one;

1H,2,3,3a,4-tetrahydro-2-carbamoylmethyl-3a-phenyl-8-methyl-imidazo[5,1-c][1,4]benzoxazin-1-one;

1H,2,3,3a,4-tetrahydro-2-carbamoylmethyl-3a-phenyl-8-trifluoromethyl-imidazo[5,1-c][1,4]benzoxazin-1-one;

1H,2,3,3a,4-tetrahydro-2-carbamoylmethyl-3a-phenyl-8-methoxy-imidazo[5,1-c][1,4]-benzoxazin-1-one;

1H,2,3,3a,4-tetrahydro-2-carbamoylmethyl-3a-phenyl-8-carboxy-imidazo[5,1-c][1,4]benzoxazin-1-one;

1H,2,3,3a,4-tetrahydro-2-carbamoylmethyl-3a-phenyl-8-acetamido-imidazo[5,1-c][1,4]benzoxazin-1-one;

1H,2,3,3a,4-tetrahydro-2-carbamoylmethyl-3a-phenyl-8-methylsulfonyl-imidazo[5,1-c][1,4]benzoxazin-1-one;

1H,2,3,3a,4-tetrahydro-2-carbamoylmethyl-3a-phenyl-8-methylsulfonamido-imidazo[5,1-c][1,4]benzoxazin-1-one.

EXAMPLE 22

A mixture of 2H-3,4-dihydro-3-aminomethyl-3-phenyl-[1,4]benzoxazin (2 g) and urea (0.72 g) was heated to fusion under a nitrogen steam for 3 hours at 140° C. then at 180° C. for other 2 hours. After grinding in water, filtration and crystallization from toluene, 1H,2,3,3a,4-tetrahydro-3a-phenyl-imidazo[5,1-c][1,4]benzoxazin-1-one (1.5 g; m.p. 258°–260° C.) was obtained.

Analogously, the following compounds were obtained:

1H,2,3,3a,4-tetrahydro-3a-phenyl-8-chloro-imidazo[5,1-c][1,4]benzoxazin-1-one;

1H,2,3,3a,4-tetrahydro-3a-phenyl-8-fluoro-imidazo[5,1-c][1,4]benzoxazin-1-one;

1H,2,3,3a,4-tetrahydro-3a-phenyl-8-hydroxy-imidazo[5,1-c][1,4]benzoxazin-1-one;

1H,2,3,3a,4-tetrahydro-3a-phenyl-8-amino-imidazo[5,1-c][1,4]benzoxazin-1-one;

1H,2,3,3a,4-tetrahydro-3a-phenyl-8-methyl-imidazo[5,1-c][1,4]benzoxazin-1-one;

1H,2,3,3a,4-tetrahydro-3a-phenyl-8-trifluoromethyl-imidazo[5,1-c][1,4]benzoxazin-1-one;

1H,2,3,3a,4-tetrahydro-3a-phenyl-8-methoxy-imidazo[5,1-c][1,4]benzoxazin-1-one;

1H,2,3,3a,4-tetrahydro-3a-phenyl-8-carboxy-imidazo[5,1-c][1,4]benzoxazin-1-one;

1H,2,3,3a,4-tetrahydro-3a-phenyl-8-acetamido-imidazo[5,1-c][1,4]benzoxazin-1-one;

1H,2,3,3a,4-tetrahydro-3a-phenyl-8-methylsulfonyl-imidazo[5,1-c][1,4]benzoxazin-1-one;

1H,2,3,3a,4-tetrahydro-3a-phenyl-8-methylsulfonamido-imidazo[5,1-c][1,4]benzoxazin-1-one.

EXAMPLE 23

A solution of 2H-3,4-dihydro-3-cyano-3-phenyl-[1,4]benzoxazine (10 g; $4.2 \cdot 10^{-2}$ moles) in EtOH (300 ml) was first saturated with $NH_3$ and then reduced with Nickel/Raney at room temperature and at 4 atmospheres. After 4 hours the reduction was complete. After filtration, evaporation to dryness and crystallization from ethyl ether, 2H-3,4-dihydro-3-aminomethyl-3-phenyl-[1,4]benzoxazine (5.4 g; m.p. 87°–89° C.) was obtained.

Analogously, the following compounds were obtained:

2H-3,4-dihydro-3-aminomethyl-3-phenyl-6-fluoro-[1,4]benzoxazine;

2H-3,4-dihydro-3-aminomethyl-3-phenyl-6-hydroxy-[1,4]benzoxazine;

2H-3,4-dihydro-3-aminomethyl-3-phenyl-6-amino-[1,4]benzoxazine;

2H-3,4-dihydro-3-aminomethyl-3-phenyl-6-methyl-[1,4]benzoxazine;

2H-3,4-dihydro-3-aminomethyl-3-phenyl-6-trifluoromethyl-[1,4]benzoxazine;

2H-3,4-dihydro-3-aminomethyl-3-phenyl-6-methoxy-[1,4]benzoxazine;

2H-3,4-dihydro-3-aminomethyl-3-phenyl-6-carboxy-[1,4]benzoxazine;

2H,3,4-dihydro-3-aminomethyl-3-phenyl-6-acetamido-[1,4]benzoxazine;

2H-3,4-dihydro-3-aminomethyl-3-phenyl-6-methylsulfonyl-[1,4]benzoxazine.

2H-3,4-dihydro-3-aminomethyl-3-phenyl-6-methylsulfonamido-[1,4]benzoxazine.

EXAMPLE 24

A solution of 2H-3-phenyl-[1,4]benzoxazine (60 g; 0.277 moles), $Na_2S_2O_5$ (52.7 g; 0.27 moles) and KCN (55.5 g; 0.84 moles) was stirred in dimethylformamide (1000 ml) and water (200 ml) for 70 hours at room temperature, then poured in water and extracted with $CHCl_3$; the extracts were washed with diluted NaOH then with water. After evaporation to dryness the obtained solid residue was ground in benzene so obtaining 2H-3,4-dihydro-3-cyano-3-phenyl-[1,4]benzoxazine (49 g; m.p. 91°–94° C.).

Analogously, the following compounds were obtained:

2H-3,4-dihydro-3-cyano-3-phenyl-6-chloro-[1,4]benzoxazine;

2H-3,4-dihydro-3-cyano-3-phenyl-6-fluoro-[1,4]benzoxazine;

2H-3,4-dihydro-3-cyano-3-phenyl-6-hydroxy-[1,4]benzoxazine;

2H-3,4-dihydro-3-cyano-3-phenyl-6-amino-[1,4]benzoxazine;

2H-3,4-dihydro-3-cyano-3-phenyl-6-methyl-[1,4]benzoxazine;
2H-3,4-dihydro-3-cyano-3-phenyl-6-trifluoromethyl-[1,4]benzoxazine;
2H-3,4-dihydro-3-cyano-3-phenyl-6-methoxy-[1,4]benzoxazine;
2H-3,4-dihydro-3-cyano-3-phenyl-6-carboxy-[1,4]benzoxazine;
2H-3,4-dihydro-3-cyano-3-phenyl-6-acetamido-[1,4]benzoxazine;
2H-3,4-dihydro-3-cyano-3-phenyl-6-methylsulfonyl-[1,4]benzoxazine;
2H-3,4-dihydro-3-cyano-3-phenyl-6-methylsulfonamido-[1,4]benzoxazine.

EXAMPLE 25

Proceeding as described in example 1, starting from 1H,2,3,3a,4-tetrahydro-4,4-dimethyl-imidazo[5,1-c][1,4]benzoxazine (2.36 g; $2.10^{-2}$ moles), 1H,2,3,3a,4-tetrahydro-2-carbamoylmethyl-4,4-dimethyl-imidazo[5,1-c][1,4]benzoxazine (2.3 g) was obtained.

Analogously, the following compounds were obtained:
1H,2,3,3a,4-tetrahydro-2-methyl-4,4-dimethyl-imidazo[5,1-c][1,4]benzoxazine;
1H,2,3,3a,4-tetrahydro-2-(2'-carbamoyl-ethyl)-4,4-dimethyl-imidazo[5,1-c][1,4]benzoxazine;
1H,2,3,3a,4-tetrahydro-2-(1'-carbamoyl-ethyl)-4,4-dimethyl-imidazo[5,1-c][1,4]benzoxazine;
1H,2,3,3a,4-tetrahydro-2-(1'-methyl-1'-carbamoyl-ethyl)-4,4-dimethyl-imidazo[5,1-c][1,4]benzoxazine;
1H,2,3,3a,4-tetrahydro-2-(2'-dimethylaminoethyl)-4,4-dimethyl-imidazo[5,1-c][1,4]benzoxazine;
1H,2,3,3a,4-tetrahydro-2-(3'-dimethylaminopropyl)-4,4-dimethyl-imidazo[5,1-c][1,4]benzoxazine;
1H,2,3,3a,4-tetrahydro-2-propargyl-4,4-dimethyl-imidazo[5,1-c][1,4]benzoxazine;
1H,2,3,3a,4-tetrahydro-2-benzyl-4,4-dimethyl-imidazo[5,1-c][1,4]benzoxazine;
1H,2,3,3a,4-tetrahydro-2-(p-methylsulfonyl-benzyl)-4,4-dimethyl-imidazo[5,1-c][1,4]benzoxazine;
1H,2,3,3a,4-tetrahydro-2-(3'-t-amylsulfonylpropyl)-4,4-dimethyl-imidazo[5,1-c][1,4]benzoxazine;
1H,2,3,3a,4-tetrahydro-2-carbamoylmethyl-4,4-dimethyl-8-chloro-imidazo[5,1-c][1,4]benzoxazine;
1H,2,3,3a,4-tetrahydro-2-carbamoylmethyl-4,4-dimethyl-8-fluoro-imidazo[5,1-c][1,4]benzoxazine;
1H,2,3,3a,4-tetrahydro-2-carbamoylmethyl-4,4-dimethyl-8-hydroxy-imidazo[5,1-c][1,4]benzoxazine;
1H,2,3,3a,4-tetrahydro-2-carbamoylmethyl-4,4-dimethyl-8-amino-imidazo[5,1-c][1,4]benzoxazine;
1H,2,3,3a,4-tetrahydro-2-carbamoylmethyl-4,4-dimethyl-8-methyl-imidazo[5,1-c][1,4]benzoxazine;
1H,2,3,3a,4-tetrahydro-2-carbamoylmethyl-4,4-dimethyl-8-trifluoromethyl-imidazo[5,1-c][1,4]benzoxazine;
1H,2,3,3a,4-tetrahydro-2-carbamoylmethyl-4,4-dimethyl-8-methoxy-imidazo[5,1-c][1,4]benzoxazine;
1H,2,3,3a,4-tetrahydro-2-carbamoylmethyl-4,4-dimethyl-8-carboxy-imidazo[5,1-c][1,4]benzoxazine;
1H,2,3,3a,4-tetrahydro-2-carbamoylmethyl-4,4-dimethyl-8-acetamido-imidazo[5,1-c][1,4]benzoxazine;
1H,2,3,3a,4-tetrahydro-2-carbamoylmethyl-4,4-dimethyl-8-methylsulfonyl-imidazo[5,1-c][1,4]benzoxazine;
1H,2,3,3a,4-tetrahydro-2-carbamoylmethyl-4,4-dimethyl-8-methylsulfonamido-imidazo[5,1-c][1,4]benzoxazine.

EXAMPLE 26

To a solution of 2H-2,2-dimethyl-3-succinimidomethyl-[1,4]benzoxazine (2.74 g; $1.10^{-2}$ moles) in MeOH, NaBH$_4$ (1 g) was added; the solution was stirred at room temperature for 3 hours then poured in water and brought to pH = 3 with diluted HCl. After evaporation of the methanol excess under vacuum, the solution was alkalized with a Na$_2$CO$_3$ saturated solution and extracted with chloroform; the extracts were washed with water, dried on Na$_2$SO$_4$ and evaporated to dryness so obtaining, after crystallization from anhydrous ethanol, 2H-3,4-dihydro-2,2-dimethyl-3-succinimidomethyl-[1,4]benzoxazine (2.3 g).

Analogously, the following compounds were obtained:
2H-3,4-dihydro-2,2-dimethyl-3-succinimidomethyl-6-chloro-[1,4]benzoxazine;
2H-3,4-dihydro-2,2-dimethyl-3-succinimidomethyl-6-fluoro-[1,4]benzoxazine;
2H-3,4-dihydro-2,2-dimethyl-3-succinimidomethyl-6-hydroxy-[1,4]benzoxazine;
2H-3,4-dihydro-2,2-dimethyl-3-succinimidomethyl-6-amino-[1,4]benzoxazine;
2H-3,4-dihydro-2,2-dimethyl-3-succinimidomethyl-6-methyl-[1,4]benzoxazine;
2H-3,4-dihydro-2,2-dimethyl-3-succinimidomethyl-6-trifluoromethyl-[1,4]benzoxazine;
2H-3,4-dihydro-2,2-dimethyl-3-succinimidomethyl-6-methoxy-[1,4]benzoxazine;
2H-3,4-dihydro-2,2-dimethyl-3-succinimidomethyl-6-carboxy-[1,4]benzoxazine;
2H-3,4-dihydro-2,2-dimethyl-3-succinimidomethyl-6-acetamido-[1,4]benzoxazine;
2H-3,4-dihydro-2,2-dimethyl-3-succinimidomethyl-6-methylsulfonyl-[1,4]benzoxazine;
2H-3,4-dihydro-2,2-dimethyl-3-succinimidomethyl-6-methylsulfonamido-[1,4]benzoxazine.

EXAMPLE 27

1-succinimido-3,3-dimethyl-3-(o-nitrophenoxy)-2-propanone (3 g) was catalitically reduced at room temperature with 10% Pd/C (0.3 g) at 4 atmospheres. After 4 hours the solution was filtered and concentrated to little volume, so obtaining the precipitation of 2H-2,2-dimethyl-3-succinimidomethyl-[1,4]benzoxazine (1.8 g; m.p. 177°–178° C.

Analogously, the following compounds were obtained:
2H-2,2-dimethyl-3-succinimidomethyl-6-fluoro-[1,4]benzoxazine;
2H-2,2-dimethyl-3-succinimidomethyl-6-hydroxy-[1,4]benzoxazine;
2H-2,2-dimethyl-3-succinimidomethyl-6-amino-[1,4]benzoxazine;
2H-2,2-dimethyl-3-succinimidomethyl-6-methyl-[1,4]benzoxazine;
2H-2,2-dimethyl-3-succinimidomethyl-6-trifluoromethyl-[1,4]benzoxazine;
2H-2,2-dimethyl-3-succinimidomethyl-6-methoxy-[1,4]benzoxazine;
2H-2,2-dimethyl-3-succinimidomethyl-6-carboxy-[1,4]benzoxazine;
2H-2,2-dimethyl-3-succinimidomethyl-6-acetamido-[1,4]benzoxazine;
2H-2,2-dimethyl-3-succinimidomethyl-6-methylsulfonyl-[1,4]benzoxazine;

2H-2,2-dimethyl-3-succinimidomethyl-6-methylsulfonamido-[1,4]benzoxazine.

EXAMPLE 28

To a suspension of NaH (1.6 g; $3.3.10^{-2}$ moles) in dimethylformamide (100 ml), succinimide (3.25 g; $3.3.10^{-2}$ moles) was added under a nitrogen steam; after stirring for 1 hour at room temperature, the solution was cooled at 0° C. and a solution of 1-bromo-3,3-dimethyl-3-(o-nitrophenoxy)-2-propanone (10 g; $3.3.10^{-2}$ moles) dissolved in dimethylformamide, was added dropwise. The solution was kept 2 hours at 0° C. then poured in water and extracted with Et$_2$O. The extracts were dried, treated with bleaching charcoal and concentrated, so obtaining the precipitation of 1-succinimido-3,3-dimethyl-3-(o-nitrophenoxy)-2-propanone (0.75 g; m.p. 90°-93° C.).

Analogously, the following compounds were obtained:
1-succinimido-3,3-dimethyl-3-(2-nitro-4-chlorophenoxy)-2-propanone;
1-succinimido-3,3-dimethyl-3-(2-nitro-4-fluorophenoxy)-2-propanone;
1-succinimido-3,3-dimethyl-3-(2-nitro-4-hydroxyphenoxy)-2-propanone;
1-succinimido-3,3-dimethyl-3-(2-nitro-4-aminophenoxy)-2-propanone;
1-succinimido-3,3-dimethyl-3-(2-nitro-4-methylphenoxy)-2-propanone;
1-succinimido-3,3-dimethyl-3-(2-nitro-4-trifluoromethylphenoxy)-2-propanone;
1-succinimido-3,3-dimethyl-3-(2-nitro-4-methoxyphenoxy)-2-propanone;
1-succinimido-3,3-dimethyl-3-(2-nitro-4-carboxyphenoxy)-2-propanone;
1-succinimido-3,3-dimethyl-3-(2-nitro-4-acetamidophenoxy)-2-propanone;
1-succinimido-3,3-dimethyl-3-(2-nitro-4-methylsulfonylphenoxy)-2-propanone;
1-succinimido-3,3-dimethyl-3-(2-nitro-4-methylsulfonamidophenoxy)-2-propanone.

EXAMPLE 29

A solution of 2-(o-nitrophenoxy)-2-methyl-propionyl chloride (28.5 g; $1.17.10^{-2}$ moles) in ethyl ether (500 ml) was added dropwise at 0° C. to an ethyl ether solution of diazomethane (14.8 g; $3.51.10^{-2}$ moles). The mixture was allowed to reach spontaneously the room temperature and kept to this temperature for 8 hours; then after cooling again at 0° C., a steam of gaseous HBr was bubbled for 40 minutes. Water was then added and the resulting solution was washed with 10% Na$_2$CO$_3$ and then with water until neutral. After drying on Na$_2$SO$_4$ and evaporation to dryness, 1-bromo-3,3-dimethyl-3-(o-nitrophenoxy)-2-propanone (27.7 g) was obtained as an oil which solidified spontaneously giving a solid melting at 32°-34° C.

Analogously, the following compounds were obtained;
1-bromo-3,3-dimethyl-3-(2-nitro-4-chlorophenoxy)-2-propanone;
1-bromo-3,3-dimethyl-3-(2-nitro-4-fluorophenoxy)-2-propanone;
1-bromo-3,3-dimethyl-3-(2-nitro-4-aminophenoxy)-2-propanone;
1-bromo-3,3-dimethyl-3-(2-nitro-4-methylphenoxy)-2-propanone;
1-bromo-3,3-dimethyl-3-(2-nitro-4-trifluoromethylphenoxy)-2-propanone;
1-bromo-3,3-dimethyl-3-(2-nitro-4-methoxyphenoxy)-2-propanone;
1-bromo-3,3-dimethyl-3-(2-nitro-4-acetamidophenoxy)-2-propanone;
1-bromo-3,3-dimethyl-3-(2-nitro-4-methylsulfonylphenoxy)-2-propanone;
1-bromo-3,3-dimethyl-3-(2-nitro-4-methylsulfonamidophenoxy)-2-propanone.

EXAMPLE 30

To a solution of 1H,2,3,3a,4-tetrahydro-imidazo[5,1-c][1,4]benzothiazin-1-one (2.06 g; $1.10^{-2}$ moles) in anhydrous dimethylacetamide (50 ml), 50% NaH (0.55 g; $1.1.10^{-2}$ moles) was added under stirring and the mixture was heated at 50° C. for 30 minutes. The temperature was then brought to the room temperature and chloroacetamide (0.95 g; $1.05.10^{-2}$ moles) dissolved in anhydrous dimethylacetamide (10 ml) was added dropwise. The mixture was heated at 60° C. for 1 hour, poured in water and extracted with ethyl acetate. The extracts were dried on Na$_2$SO$_4$, filtered and concentrated so obtaining, after crystallization from chloroform/methanol, 1H,2,3,3a,4-tetrahydro-2-carbamoylmethyl-imidazo[5,1-c][1,4]benzothiazin-1-one (1.65 g).

Analogously, the following compounds were obtained:
1H,2,3,3a,4-tetrahydro-2-methyl-imidazo[5,1-c][1,4]benzothiazin-1-one;
1H,2,3,3a,4-tetrahydro-2-(2'-carbamoyl-ethyl)-imidazo[5,1-c][1,4]benzothiazin-1-one;
1H,2,3,3a,4-tetrahydro-2-(1'-carbamoyl-ethyl)-imidazo[5,1-c][1,4]benzothiazin-1-one;
1H,2,3,3a,4-tetrahydro-2-(1'-methyl-1'-carbamoyl-ethyl)-imidazo[5,1-c][1,4]benzothiazin-1-one;
1H,2,3,3a,4-tetrahydro-2-(2'-dimethylaminoethyl)-imidazo[5,1-c][1,4]benzothiazin-1-one;
1H,2,3,3a,4-tetrahydro-2-(3'-dimethylaminopropyl)-imidazo[5,1-c][1,4]benzothiazin-1-one;
1H,2,3,3a,4-tetrahydro-2-propargyl-imidazo[5,1-c][1,4]benzothiazin-1-one;
1H,2,3,3a,4-tetrahydro-2-benzyl-imidazo[5,1-c][1,4]benzothiazin-1-one;
1H,2,3,3a,4-tetrahydro-2-(p-methylsulfonyl-benzyl)-imidazo[5,1-c][1,4]benzothiazin-1-one;
1H,2,3,3a,4-tetrahydro-2-(3'-t-amylsulfonylpropyl)-imidazo[5,1-c][1,4]benzothiazin-1-one;
1H,2,3,3a,4-tetrahydro-2-carbamoylmethyl-8-chloro-imidazo[5,1-c][1,4]benzothiazin-1-one;
1H,2,3,3a,4-tetrahydro-2-carbamoylmethyl-8-fluoro-imidazo[5,1-c][1,4]benzothiazin-1-one;
1H,2,3,3a,4-tetrahydro-2-carbamoylmethyl-8-hydroxy-imidazo[5,1-c][1,4]benzothiazin-1-one;
1H,2,3,3a,4-tetrahydro-2-carbamoylmethyl-8-amino-imidazo[5,1-c][1,4]benzothiazin-1-one;
1H,2,3,3a,4-tetrahydro-2-carbamoylmethyl-8-methyl-imidazo[5,1-c][1,4]benzothiazin-1-one;
1H,2,3,3a,4-tetrahydro-2-carbamoylmethyl-8-trifluoromethyl-imidazo[5,1-c][1,4]benzothiazin-1-one;
1H,2,3,3a,4-tetrahydro-2-carbamoylmethyl-8-methoxy-imidazo[5,1-c][1,4]benzothiazin-1-one;
1H,2,3,3a,4-tetrahydro-2-carbamoylmethyl-8-carboxy-imidazo[5,1-c][1,4]benzothiazin-1-one;
1H,2,3,3a,4-tetrahydro-2-carbamoylmethyl-8-acetamido-imidazo[5,1-c][1,4]benzothiazin-1-one;
1H,2,3,3a,4-tetrahydro-2-carbamoylmethyl-8-methylsulfonyl-imidazo[5,1-c][1,4]benzothiazin-1-one;

1H,2,3,3a,4-tetrahydro-2-carbamoylmethyl-8-methyl-sulfonamido-imidazo[5,1-c][1,4]benzothiazin-1-one;
1H,2,3,3a,4-tetrahydro-2-carbamoylmethyl-3a-phenyl-imidazo[5,1-c][1,4]benzothiazin-1-one;
1H,2,3,3a,4-tetrahydro-2-carbamoylmethyl-4-phenyl-imidazo[5,1-c][1,4]benzothiazin-1-one;
1H,2,3,3a,4-tetrahydro-2-carbamoylmethyl-4,4-dimethyl-imidazo[5,1-c][1,4]benzothiazin-1-one.

EXAMPLE 31

To a suspension of NaBH$_4$ (7.8 g; 2.1.10$^{-1}$ moles) in tetrahydrofuran (170 ml), an ethyl ether solution of BF$_3$ (d. 1.126; 24.2 ml) was added at −5° C. By keeping the temperature at −5° C., a solution of 1,2,3,4,4a,5-hexahydro-1-phenyl-3-methyl-pyrazo[2,1-c][1,4]benzoxazin-2-one (10 g; 3.4.10$^{-2}$ moles) in tetrahydrofuran (100 ml) was added dropwise. The mixture was allowed to reach the room temperature and then kept at this temperature for 12 hours. Water was then added cautiously and the resulting solution as evaporated to dryness; the residue was taken up with water, the solution alkalized with 2N NaOH and extracted with Et$_2$O. The ethereal phase was washed with water, dried on Na$_2$SO$_4$ and evaporated to dryness so obtaining a solid, which was crystallized twice from ethanol to give 1,2,3,4,4a,5-hexahydro-1-phenyl-3-methyl-pyrazo[2,1-c][1,4-benzoxazine (3.6 g; m.p. 126°–129° C.).

Analogously, the following compounds were obtained:
1,2,3,4,4a,5-hexahydro-1-phenyl-pyrazo[2,1-c][1,4]benzoxazine;
1,2,3,4,4a,5-hexahydro-1-phenyl-3-(2'-dimethylaminoethyl)-pyrazo[2,1-c][1,4]benzoxazine;
1,2,3,4,4a,5-hexahydro-1-phenyl-3-(3'-dimethylaminopropyl)-pyrazo[2,1-c][1,4]benzoxazine.

EXAMPLE 32

To a solution of 1,2,3,4,4a,5-hexahydro-1-phenyl-pyrazo[2,1-c][1,4-benzoxazine (2.7 g; 1.10$^{-2}$ moles) in dimethylformamide containing an excess of potassium carbonate chloroacetamide (1.12 g; 1.2.10$^{-2}$ moles) was added. The solution was kept 8 hours at 50° C. then poured in water and extracted many times with ethyl ether; the extracts were dried and evaporated to dryness and the residue crystallized from EtOH so obtaining 1,2,3,4,4a,5-hexahydro-3-carbamoylmethyl-1-phenyl-pyrazo[2,1-c][1,4]benzoxazine (2.1 g), m.p. 200°–201° C.

Analogously, the following compounds were obtained:
1,2,3,4,4a,5-hexahydro-3-methyl-1-phenyl-pyrazo[2,1-c][1,4]benzoxazine, m.p. 126°–129° C.;
1,2,3,4,4a,5-hexahydro-3-(2'-carbamoyl-ethyl)-1-phenyl-pyrazo[2,1-c][1,4]benzoxazine;
1,2,3,4,4a,5-hexahydro-3-(1'-carbamoyl-ethyl)-1-phenyl-pyrazo[2,1-c][1,4]benzoxazine;
1,2,3,4,4a,5-hexahydro-3-(1'-methyl-1'-carbomoyl-ethyl)-1-phenyl-pyrazo[2,1-c][1,4]benzoxazine;
1,2,3,4,4a,5-hexahydro-3-(2'-dimethylaminoethyl)-1-phenyl-pyrazo[2,1-c][1,4]benzoxazine;
1,2,3,4,4a,5-hexahydro-3-(3'-dimethylaminopropyl)-1-phenyl-pyrazo[2,1-c][1,4]benzoxazine;
1,2,3,4,4a,5-hexahydro-3-propargyl-1-phenyl-pyrazo[2,1-c][1,4]benzoxazine;
1,2,3,4,4a,5-hexahydro-3-benzyl-1-phenyl-pyrazo[2,1-c][1,4]benzoxazine;
1,2,3,4,4a,5-hexahydro-3-(p-methylsulfonyl-benzyl)-1-phenyl-pyrazo[2,1-c][1,4]benzoxazine;
1,2,3,4,4a,5-hexahydro-3-(3'-t-amylsulfonylpropyl)-1-phenyl-pyrazo[2,1-c][1,4]benzoxazine;
1,2,3,4,4a,5-hexahydro-3-carbamoylmethyl-1-phenyl-9-chloro-pyrazo[2,1-c][1,4]benzoxazine.

EXAMPLE 33

Starting from 1,2,3,4,4a,5-hexahydro-1-phenyl-pyrazo[2,1-c][1,4]benzoxazin-2-one (2.85 g; 1.10$^{-2}$ moles) and proceeding as described in example 1, 1,2,3,4,4a,5-hexahydro-1-phenyl-3-methyl-pyrazo[2,1-c][1,4]benzoxazin-2-one (2.3 g) m.p. 189°–192° C., was obtained after crystallization from methanol.

Analogously, the following compounds were obtained:
1,2,3,4,4a,5-hexahydro-1-phenyl-3-carbamoylmethyl-pyrazo[2,1-c][1,4]benzoxazin-2-one;
1,2,3,4,4a,5-hexahydro-1-phenyl-3-(2'-carbamoyl-ethyl)-pyrazo[2,1-c][1,4]benzoxazin-2-one;
1,2,3,4,4a,5-hexahydro-1-phenyl-3-(1'-carbamoyl-ethyl)-pyrazo[2,1-c][1,4]benzoxazin-2-one;
1,2,3,4,4a,5-hexahydro-1-phenyl-3-(1'-methyl-1'-carbamoyl-ethyl)-pyrazo[2,1-c][1,4]benzoxazin-2-one;
1,2,3,4,4a,5-hexahydro-1-phenyl-3-(2'-dimethylaminoethyl)-pyrazo[2,1-c][1,4]benzoxazin-2-one;
1,2,3,4,4a,5-hexahydro-1-phenyl-3-(3'-dimethylaminopropyl)-pyrazo[2,1-c][1,4]benzoxazin-2-one;
1,2,3,4,4a,5-hexahydro-1-phenyl-3-propargyl-pyrazo[2,1-c][1,4]benzoxazin-2-one;
1,2,3,4,4a,5-hexahydro-1-phenyl-3-benzyl-pyrazo[2,1-c][1,4]benzoxazin-2-one;
1,2,3,4,4a,5-hexahydro-1-phenyl-3-(p-methylsulfonyl-benzyl)-pyrazo[2,1-c][1,4]benzoxazin-2-one;
1,2,3,4,4a,5-hexahydro-1-phenyl-3-(3'-t-amylsulfonylpropyl)-pyrazo[2,1-c][1,4]benzoxazin-2-one;
1,2,3,4,4a,5-hexahydro-1-phenyl-3-carbamoylmethyl-9-chloro-pyrazo[2,1-c][1,4]benzoxazin-2-one;
1,2,3,4,4a,5-hexahydro-1-phenyl-3-carbamoylmethyl-9-fluoro-pyrazo[2,1-c][1,4]benzoxazin-2-one;
1,2,3,4,4a,5-hexahydro-1-phenyl-3-carbamoylmethyl-9-hydroxy-pyrazo[2,1-c][1,4]benzoxazin-2-one;
1,2,3,4,4a,5-hexahydro-1-phenyl-3-carbamoylmethyl-9-amino-pyrazo[2,1-c][1,4]benzoxazin-2-one;
1,2,3,4,4a,5-hexahydro-1-phenyl-3-carbamoylmethyl-9-methyl-pyrazo[2,1-c][1,4]benzoxazin-1-one;
1,2,3,4,4a,5-hexahydro-1-phenyl-3-carbamoylmethyl-9-trifluoromethyl-pyrazo[2,1-c][1,4]benzoxazin-2-one;
1,2,3,4,4a,5-hexahydro-1-phenyl-3-carbamoylmethyl-9-methoxy-pyrazo[2,1-c][1,4]benzoxazin-2-one;
1,2,3,4,4a,5-hexahydro-1-phenyl-3-carbamoylmethyl-9-carboxy-pyrazo[2,1-c][1,4]benzoxazin-2-one;
1,2,3,4,4a,5-hexahydro-1-phenyl-3-carbamoylmethyl-9-acetamido-pyrazo[2,1-c][1,4]benzoxazin-2-one;
1,2,3,4,4a,5-hexahydro-1-phenyl-3-carbamoylmethyl-9-methylsulfonyl-pyrazo[2,1-c][1,4]benzoxazin-2-one;
1,2,3,4,4a,5-hexahydro-1-phenyl-3-carbamoylmethyl-9-methylsulfonamido-pyrazo[2,1-c][1,4]benzoxazin-2-one.

EXAMPLE 34

To a solution of 3-[N-(1'-chloro-1'-phenyl)-acetyl]-aminomethyl-[1,4]benzoxazine (26 g; 8.2.10$^{-2}$ moles) in 90% EtOH (150 ml), KJ (25 g) was added and the mixture refluxed for 3 hours. The solid was filtered off and the ethyl ether was evaporated to dryness so obtaining an oil which by elution on a silica gel column [CHCl$_3$:MeOH:NH$_3$ (190:10:0.5)], gave 1,2,3,4,4a,5-hexahydro-1-phenyl-pyrazo[2,1-c][1,4]benzoxazin-2-one (19.7 g), m.p. 216°–219° C.

Analogously, the following compounds were obtained:

1,2,3,4,4a,5-hexahydro-1-phenyl-9-chloro-pyrazo[2,1-c][1,4]benzoxazin-2-one;
1,2,3,4,4a,5-hexahydro-1-phenyl-9-fluoro-pyrazo[2,1-c][1,4]benzoxazin-2-one;
1,2,3,4,4a,5-hexahydro-1-phenyl-9-hydroxy-pyrazo[2,1-c][1,4]-benzoxazin-2-one;
1,2,3,4,4a,5-hexahydro-1-phenyl-9-amino-pyrazo[2,1-c][1,4]benzoxazin-2-one;
1,2,3,4,4a,5-hexahydro-1-phenyl-9-methyl-pyrazo[2,1-c][1,4]benzoxazin-2-one;
1,2,3,4,4a,5-hexahydro-1-phenyl-9-trifluoromethyl-pyrazo[2,1-c][1,4]benzoxazin-2-one;
1,2,3,4,4a,5-hexahydro-1-phenyl-9-methoxy-pyrazo[2,1-c][1,4]benzoxazin-2-one;
1,2,3,4,4a,5-hexahydro-1-phenyl-9-carboxy-pyrazo[2,1-c][1,4]benzoxazin-2-one;
1,2,3,4,4a,5-hexahydro-1-phenyl-9-acetamido-pyrazo[2,1-c][1,4]benzoxazin-2-one;
1,2,3,4,4a,5-hexahydro-1-phenyl-9-methylsulfonyl-pyrazo[2,1-c][1,4]benzoxazin-2-one;
1,2,3,4,4a,5-hexahydro-1-phenyl-9-methylsulfonamido-pyrazo[2,1-c][1,4]benzoxazin-2-one.

EXAMPLE 35

To a solution of 3-aminomethyl-[1,4]benzoxazine (16.4 g; 1.10$^{-1}$ moles) in CH$_2$Cl$_2$ (1000 ml) and triethylamine (15 ml), 1-chloro-1-phenyl-acetyl chloride (14.7 ml) dissolved in CHCl$_3$ (200 ml) was added at −50° C. The solution was allowed to reach spontaneously the room temperature, washed with a 5% bicarbonate solution and with water until neutral, then dried and evaporated to dryness so obtaining, as a T.L.C. pure oil 3-[N-(1'-chloro-1'-phenyl)-acetyl]-aminomethyl-[1,4]benzoxazine (22.0 g).

Analogously, the following compounds were obtained:

3-[N-(1'-chloro-1'-phenyl)-acetyl]-aminomethyl-6-chloro-[1,4]benzoxazine;
3-[N-(1'-chloro-1'-phenyl)-acetyl]-aminomethyl-6-fluoro-[1,4]benzoxazine;
3-[N-(1'-chloro-1'-phenyl)-acetyl]-aminomethyl-6-hydroxy-[1,4]benzoxazine;
3-[N-(1'-chloro-1'-phenyl)-acetyl]-aminomethyl-6-amino-[1,4]benzoxazine;
3-[N-(1'-chloro-1'-phenyl)-acetyl]-aminomethyl-6-methyl-[1,4]benzoxazine;
3-[N-(1'-chloro-1'-phenyl)-acetyl]-aminomethyl-6-trifluoromethyl-[1,4]benzoxazine;
3-[N-(1'-chloro-1'-phenyl)-acetyl]-aminomethyl-6-methoxy-[1,4]benzoxazine;
3-[N-(1'-chloro-1'-phenyl)-acetyl]-aminomethyl-6-carboxy-[1,4]benzoxazine;
3-[N-(1'-chloro-1'-phenyl)-acetyl]-aminomethyl]-6-acetamido-[1,4]benzoxazine;
3-[N-(1'-chloro-1'-phenyl)-acetyl]-aminomethyl-6-methylsulfonyl-[1,4]benzoxazine;
3-[N-(1'-chloro-1'-phenyl)-acetyl]-aminomethyl-6-methylsulfonamido-[1,4]benzoxazine.

EXAMPLE 36

Starting from 1,2,3,4,4a,5-hexahydro-pyrazo[2,1-c][1,4]benzoxazin-2-one (4.1 g; 2.10$^{-1}$ moles) and proceeding as described in example 1, 1,2,3,4,4a,5-hexahydro-3-carbamoylmethyl-pyrazo[2,1-c][1,4]benzoxazin-2-one, (3.0 g) m.p. 230°–232° C. was obtained.

Analogously, the following compounds are obtained:

1,2,3,4,4a,5-hexahydro-3-methyl-pyrazo[2,1-c][1,4]benzoxazin-2-one;
1,2,3,4,4a,5-hexahydro-3-(2'-carbamoyl-ethyl)-pyrazo[2,1-c][1,4]benzoxazin-2-one;
1,2,3,4,4a,5-hexahydro-3-(1'-carbamoyl-ethyl)-pyrazo[2,1-c][1,4]benzoxazin-2-one;
1,2,3,4,4a,5-hexahydro-3-(1'-methyl-1'-carbamoyl-ethyl)-pyrazo[2,1-c][1,4]benzoxazin-2-one;
1,2,3,4,4a,5-hexahydro-3-(2'-dimethylaminoethyl)-pyrazo[2,1-c][1,4]benzoxazin-2-one;
1,2,3,4,4a,5-hexahydro-3-(3'-dimethylaminopropyl)-pyrazo[2,1-c][1,4]benzoxazin-2-one, m.p. 108°–110° C.;
1,2,3,4,4a,5-hexahydro-3-propargyl-pyrazo[2,1-c][1,4]benzoxazin-2-one;
1,2,3,4,4a,5-hexahydro-3-benzyl-pyrazo[2,1-c][1,4]benzoxazin-2-one;
1,2,3,4,4a,5-hexahydro-3-(p-methylsulfonyl-benzyl)-pyrazo[2,1-c][1,4]benzoxazin-2-one;
1,2,3,4,4a,5-hexahydro-3-(3'-t-amylsulfonylpropyl)-pyrazo[2,1-c][1,4]benzoxazin-2-one;
1,2,3,4,4a,5-hexahydro-3-carbamoylmethyl-9-chloro-pyrazo[2,1-c][1,4]benzoxazin-2-one;
1,2,3,4,4a,5-hexahydro-3-carbamoylmethyl-9-fluoro-pyrazo[2,1-c][1,4]benzoxazin-2-one;
1,2,3,4,4a,5-hexahydro-3-carbamoylmethyl-9-hydroxy-pyrazo[2,1-c][1,4]benzoxazin-2-one;
1,2,3,4,4a,5-hexahydro-3-carbamoylmethyl-9-amino-pyrazo[2,1-c][1,4]benzoxazin-2-one;
1,2,3,4,4a,5-hexahydro-3-carbamoylmethyl-9-methyl-pyrazo[2,1-c][1,4]benzoxazin-2-one;
1,2,3,4,4a,5-hexahydro-3-carbamoylmethyl-9-trifluoromethyl-pyrazo[2,1-c][1,4]benzoxazin-2-one;
1,2,3,4,4a,5-hexahydro-3-carbamoylmethyl-9-methoxy-pyrazo[2,1-c][1,4]benzoxazin-2-one;
1,2,3,4,4a,5-hexahydro-3-carbamoylmethyl-9-carboxy-pyrazo[2,1-c][1,4]benzoxazin-2-one;
1,2,3,4,4a,5-hexahydro-3-carbamoylmethyl-9-acetamido-pirazo[2,1-c][1,4]benzoxazin-2-one;
1,2,3,4,4a,5-hexahydro-3-carbamoylmethyl-9-methylsulfonyl-pyrazo[2,1-c][1,4]benzoxazin-2-one;
1,2,3,4,4a,5-hexahydro-3-carbamoylmethyl-9-methylsulfonamido-pyrazo[2,1-c][1,4]benzoxazin-2-one;
1,2,3,4,4a,5-hexahydro-3-carbamoylmethyl-5-phenyl-pyrazo[2,1-c][1,4]benzoxazin-2-one;
1,2,3,4,4a,5-hexahydro-3-methyl-5-phenyl-pyrazo[2,1-c][1,4]benzoxazin-2-one;
1,2,3,4,4a,5-hexahydro-3-(2'-carbamoyl-ethyl)-5-phenyl-pyrazo[2,1-c][1,4]benzoxazin-2-one;
1,2,3,4,4a,5-hexahydro-3-(1'-carbamoyl-ethyl)-5-phenyl-pyrazo[2,1-c][1,4]benzoxazin-2-one;
1,2,3,4,4a,5-hexahydro-3-(1'-methyl-1'-carbamoyl-ethyl)-5-phenyl-pyrazo[2,1-c][1,4]benzoxazin-2-one;
1,2,3,4,4a,5-hexahydro-3-(2'-dimethylaminoethyl)-5-phenyl-pyrazo[2,1-c][1,4]benzoxazin-2-one;
1,2,3,4,4a,5-hexahydro-3-(3'-dimethylaminopropyl)-5-phenyl-pyrazo[2,1-c][1,4]benzoxazin-2-one;
1,2,3,4,4a,5-hexahydro-3-propargyl-5-phenyl-pyrazo[2,1-c][1,4]benzoxazin-2-one;
1,2,3,4,4a,5-hexahydro-3-benzyl-5-phenyl-pyrazo[2,1-c][1,4]benzoxazin-2-one;
1,2,3,4,4a,5-hexahydro-3-(p-methylsulfonyl-benzyl)-5-phenyl-pyrazo[2,1-c][1,4]benzoxazin-2-one;
1,2,3,4,4a,5-hexahydro-3-(3'-t-amylsulfonylpropyl)-5-phenyl-pyrazo[2,1-c][1,4]benzoxazin-2-one;
1,2,3,4,4a,5-hexahydro-3-carbamoylmethyl-5-(2'-methoxyphenyl)-pyrazo[2,1-c][1,4]benzoxazin-2-one;

1,2,3,4,4a,5-hexahydro-3-methyl-5-(2'-methoxyphenyl)-pyrazo[2,1-c][1,4]benzoxazin-2-one;
1,2,3,4,4a,5-hexahydro-3-(2'-carbamoyl-ethyl)-5-(2'-methoxyphenyl)-pyrazo[2,1-c][1,4]benzoxazin-2-one;
1,2,3,4,4a,5-hexahydro-3-(1'-carbamoyl-ethyl)-5-(2'-methoxyphenyl)-pyrazo[2,1-c][1,4]benzoxazin-2-one;
1,2,3,4,4a,5-hexahydro-3-(1'-methyl-1'-carbamoyl-ethyl)-5-(2'-methoxyphenyl)-pyrazo[2,1-c][1,4]benzoxazin-2-one;
1,2,3,4,4a,5-hexahydro-3-(2'-dimethylaminoethyl)-5-(2'-methoxyphenyl)-pyrazo[2,1-c][1,4]benzoxazin-2-one;
1,2,3,4,4a,5-hexahydro-3-(3'-dimethylaminopropyl)-5-(2'-methoxyphenyl)-pyrazo[2,1-c][1,4]benzoxazin-2-one;
1,2,3,4,4a,5-hexahydro-3-propargyl-5-(2'-methoxyphenyl)-pyrazo[2,1-c][1,4]benzoxazin-2-one;
1,2,3,4,4a,5-hexahydro-3-benzyl-5-(2'-methoxyphenyl)-pyrazo[2,1-c][1,4]benzoxazin-2-one;
1,2,3,4,4a,5-hexahydro-3-(p-methylsulfonyl-benzyl)-5-(2'-methoxyphenyl)-pyrazo[2,1-c][1,4]benzoxazin-2-one;
1,2,3,4,4a,5-hexahydro-3-(3'-t-amylsulfonylpropyl)-5-(2'-methoxyphenyl)-pyrazo[2,1-c][1,4]benzoxazin-2-one;
1,2,3,4,4a,5-hexahydro-3-carbamoylmethyl-5-(4'-chlorophenyl)-pyrazo[2,1-c][1,4]benzoxazin-2-one;
1,2,3,4,4a,5-hexahydro-3-methyl-5-(4'-chlorophenyl)-pyrazo[2,1-c][1,4]benzoxazin-2-one;
1,2,3,4,4a,5-hexahydro-3-(2'-carbamoyl-ethyl)-5-(4'-chlorophenyl)pyrazo[2,1-c][1,4]benzoxazin-2-one;
1,2,3,4,4a,5-hexahydro-3-(1'-carbamoyl-ethyl)-5-(4'-chlorophenyl)-pyrazo[2,1-c][1,4]benzoxazin-2-one;
1,2,3,4,4a,5-hexahydro-3-(1'-methyl-1'-carbamoyl-ethyl)-5-(4'-chlorophenyl)-pyrazo[2,1-c][1,4]benzoxazin-2-one;
1,2,3,4,4a,5-hexahydro-3-(2'-dimethylaminoethyl)-5-(4'-chlorophenyl)-pyrazo[2,1-c][1,4]benzoxazin-2-one;
1,2,3,4,4a,5-hexahydro-3-(3'-dimethylaminopropyl)-5-(4'-chlorophenyl)-pyrazo[2,1-c][1,4]benzoxazin-2-one;
1,2,3,4,4a,5-hexahydro-3-propargyl-5-(4'-chlorophenyl)-pyrazo[2,1-c][1,4]benzoxazin-2-one;
1,2,3,4,4a,5-hexahydro-3-benzyl-5-(4'-chlorophenyl)-pyrazo[2,1-c][1,4]benzoxazin-2-one;
1,2,3,4,4a,5-hexahydro-3-(p-methylsulfonyl-benzyl)-5-(4'-chlorophenyl)-pyrazo[2,1-c][1,4]benzoxazin-2-one;
1,2,3,4,4a,5-hexahydro-3-(3'-t-amylsulfonylpropyl)-5-(4'-chlorophenyl)-pyrazo[2,1-c][1,4]benzoxazin-2-one.

EXAMPLE 37

A solution of 2H-3,4-dihydro-3-succinimidomethyl-4-ethylcarboxymethyl-[1,4]benzoxazine (8.8 g; $2.67.10^{-2}$ moles) in 37% HCl (88 ml) was refluxed for 8 hours. After evaporation to dryness, the residue was taken up with acetone and filtered so obtaining 2H-3,4-dihydro-3-aminomethyl-4-carboxymethyl-[1,4]benzoxazine-hydrochloride (3.2 g), m.p. 210° C. (dec.) as a solid. 2.1 g ($8.1.10^{-3}$ moles) of this compound was added to a solution of $K_2CO_3$ (0.6 g; $4.35.10^{-3}$ moles) in dimethylacetamide (21 ml); the mixture was boiled for 10 minutes, then water (100 ml) was added and the resulting solution filtered so obtaining 1,2,3,4,4a,5-hexahydro-pyrazo[2,1-c][1,4]benzoxazin-2-one (1.05 g) m.p. 243°–245° C.

Analogously, the following compounds were obtained:

1,2,3,4,4a,5-hexahydro-9-chloro-pyrazo[2,1-c][1,4]benzoxazin-2-one;
1,2,3,4,4a,5-hexahydro-9-fluoro-pyrazo[2,1-c][1,4]benzoxazin-2-one;
1,2,3,4,4a,5-hexahydro-9-hydroxy-pyrazo[2,1-c][1,4]benzoxazin-2-one;
1,2,3,4,4a,5-hexahydro-9-amino-pyrazo[2,1-c][1,4]benzoxazin-2-one;
1,2,3,4,4a,5-hexahydro-9-methyl-pyrazo[2,1-c][1,4]benzoxazin-2-one;
1,2,3,4,4a,5-hexahydro-9-trifluoromethyl-pyrazo[2,1-c][1,4]benzoxazin-2-one;
1,2,3,4,4a,5-hexahydro-9-methoxy-pyrazo[2,1-c][1,4]benzoxazin-2-one;
1,2,3,4,4a,5-hexahydro-9-carboxy-pyrazo[2,1-c][1,4]benzoxazin-2-one;
1,2,3,4,4a,5-hexahydro-9-methylsulfonyl-pyrazo[2,1-c][1,4]benzoxazin-2-one;
1,2,3,4,4a,5-hexahydro-5-phenyl-pyrazo[2,1-c][1,4]benzoxazin-2-one;
1,2,3,4,4a,5-hexahydro-5-(2'-methoxyphenyl)-pyrazo[2,1-c][1,4]benzoxazin-2-one;
1,2,3,4,4a,5-hexahydro-5-(4'-chlorophenyl)-pyrazo[2,1-c][1,4]benzoxazin-2-one.

EXAMPLE 38

A solution of 2H-3,4-dihydro-3-succinimidomethyl-4-ethylcarboxymethyl-[1,4]benzoxazine (45.5 g; $1.38.10^{-1}$ moles) in 37% HCl (455 ml) was refluxed for 8 hours. The solution was brought to pH 4.5 with 35% NaOH and then to pH 8.5 with solid $Na_2CO_3$. The resulting suspension was refluxed for 3 hours, so obtaining a solid which was filtered so obtaining 1,2,3,4,4a,5-hexahydro-pyrazo[2,1-c][1,4]benzoxazin-2-one (21.8 g), m.p. 243°–245° C.

Analogously, the following compounds were obtained:

1,2,3,4,4a,5-hexahydro-9-chloro-pyrazo[2,1-c][1,4]benzoxazin-2-one;
1,2,3,4,4a,5-hexahydro-9-fluoro-pyrazo[2,1-c][1,4]benzoxazin-2-one;
1,2,3,4,4a,5-hexahydro-9-hydroxy-pyrazo[2,1-c][1,4]benzoxazin-2-one;
1,2,3,4,4a,5-hexahydro-9-amino-pyrazo[2,1-c][1,4]benzoxazin-2-one;
1,2,3,4,4a,5-hexahydro-9-methyl-pyrazo[2,1-c][1,4]benzoxazin-2-one;
1,2,3,4,4a,5-hexahydro-9-trifluoromethyl-pyrazo[2,1-c][1,4]benzoxazin-2-one;
1,2,3,4,4a,5-hexahydro-9-methoxy-pyrazo[2,1-c][1,4]benzoxazin-2-one;
1,2,3,4,4a,5-hexahydro-9-carboxy-pyrazo[2,1-c][1,4]benzoxazin-2-one;
1,2,3,4,4a,5-hexahydro-9-methylsulfonyl-pyrazo[2,1-c][1,4]benzoxazin-2-one;
1,2,3,4,4a,5-hexahydro-5-phenyl-pyrazo[2,1-c][1,4]benzoxazin-2-one;
1,2,3,4,4a,5-hexahydro-5-(2'-methoxyphenyl)-pyrazo[2,1-c][1,4]benzoxazin-2-one;
1,2,3,4,4a,5-hexahydro-5-(4'-chlorophenyl)-pyrazo[2,1-c][1,4]benzoxazin-2-one.

EXAMPLE 39

To a solution of 2H-3,4-dihydro-3-succinimidomethyl-[1,4]benzoxazine (3 g; $1.16.10^{-2}$ moles) in anhydrous dimethylacetamide (45 ml), $Na_2CO_3$ (2.57 g; $1.8.10^{-2}$ moles) and ethylbromoacetate (2.64 g; $1.58.10^{-2}$ moles) was added. The mixture was kept at 150° C. for 24 hours then water was added cautiously and the resulting solution was extracted with ethyl ether; after drying on Na$_2$SO$_4$ and concentration to dryness under vacuum, an oil was obtained which solidified by treatment with pentane. By crystallization of the solid from isopropanol, 2H-3,4-dihydro-3-succinimidomethyl-4-ethylcarboxymethyl-[1,4]benzoxazine (2.5 g, m.p. 105°–110° C. was obtained.

Analogously, the following compounds were obtained:
2H-3,4-dihydro-3-succinimidomethyl-4-ethylcarboxymethyl-6-chloro-[1,4]benzoxazine;
2H-3,4-dihydro-3-succinimidomethyl-4-ethylcarboxymethyl-6-fluoro-[1,4]benzoxazine;
2H-3,4-dihydro-3-succinimidomethyl-4-ethylcarboxymethyl-6-methyl-[1,4]benzoxazine;
2H-3,4-dihydro-3-succinimidomethyl-4-ethylcarboxymethyl-6-trifluoromethyl-[1,4]benzoxazine;
2H-3,4-dihydro-3-succinimidomethyl-4-ethylcarboxymethyl-6-methoxy-[1,4]benzoxazine;
2H-3,4-dihydro-3-succinimidomethyl-4-ethylcarboxymethyl-6-carboxy-[1,4]benzoxazine;
2H-3,4-dihydro-3-succinimidomethyl-4-ethylcarboxymethyl-6-acetamido-[1,4]benzoxazine;
2H-3,4-dihydro-3-succinimidomethyl-4-ethylcarboxymethyl-6-methylsulfonyl-[1,4]benzoxazine;
2H-3,4-dihydro-3-succinimidomethyl-4-ethylcarboxymethyl-6-methylsulfonamido-[1,4]benzoxazine.

EXAMPLE 40

To a solution of 1,2,3,4,4a,5-hexahydro-pyrazo[2,1-c][1,4]benzoxazin-1-one (4.1 g; 2.10$^{-2}$ moles) and methyl iodide (2.8 g; 2.10$^{-2}$ moles) in anhydrous dimethylacetamide (100 ml), potassium carbonate (2.8 g) was added and the mixture was stirred at 100° C. for 48 hours, then poured in water. The obtained raw yellow solid was filtered (6.4 g); after crystallization from dimethylformamide/water, gave 1,2,3,4,4a,5-hexahydro-3-methyl-pyrazo[2,1-c][1,4]benzoxazin-1-one (2.9 g), m.p. 198°–201° C.

Analogously, the following compounds were obtained:
1,2,3,4,4a,5-hexahydro-3-carbamoylmethyl-pyrazo[2,1-c][1,4]benzoxazin-1-one;
1,2,3,4,4a,5-hexahydro-3-(2'-carbamoyl-ethyl)-pyrazo[2,1-c][1,4]benzoxazin-1-one;
1,2,3,4,4a,5-hexahydro-3-(1'-carbamoyl-ethyl)-pyrazo[2,1-c][1,4]benzoxazin-1-one;
1,2,3,4,4a,5-hexahydro-3-(1'-methyl-1'-carbamoyl-ethyl)-pyrazo[2,1-c][1,4]benzoxazin-1-one;
1,2,3,4,4a,5-hexahydro-3-(2'-dimethylaminoethyl)-pyrazo[2,1-c][1,4]benzoxazin-1-one;
1,2,3,4,4a,5-hexahydro-3-(3'-dimethylaminopropyl)-pyrazo[2,1-c][1,4]benzoxazin-1-one;
1,2,3,4,4a,5-hexahydro-3-propargyl-pyrazo[2,1-c][1,4]benzoxazin-1-one;
1,2,3,4,4a,5-hexahydro-3-benzyl-pyrazo[2,1-c][1,4]benzoxazin-1-one;
1,2,3,4,4a,5-hexahydro-3-(p-methylsulfonyl-benzyl)-pyrazo[2,1-c][1,4]benzoxazin-1-one;
1,2,3,4,4a,5-hexahydro-3-(3'-t-amylsulfonylpropyl)-pyrazo[2,1-c][1,4]benzoxazin-1-one;
1,2,3,4,4a,5-hexahydro-3-carbamoylmethyl-9-chloro-pyrazo[2,1-c][1,4]benzoxazin-1-one;
1,2,3,4,4a,5-hexahydro-3-carbamoylmethyl-9-fluoro-pyrazo[2,1-c][1,4]benzoxazin-1-one;
1,2,3,4,4a,5-hexahydro-3-carbamoylmethyl-9-methyl-pyrazo[2,1-c][1,4]benzoxazin-1-one;
1,2,3,4,4a,5-hexahydro-3-carbamoylmethyl-9-trifluoromethyl-pyrazo[2,1-c][1,4]benzoxazin-1-one;
1,2,3,4,4a,5-hexahydro-3-carbamoylmethyl-9-methoxy-pyrazo[2,1-c][1,4]benzoxazin-1-one;
1,2,3,4,4a,5-hexahydro-3-carbamoylmethyl-9-carboxy-pyrazo[2,1-c][1,4]benzoxazin-1-one;
1,2,3,4,4a,5-hexahydro-3-carbamoylmethyl-9-acetamido-pyrazo[2,1-c][1,4]benzoxazin-1-one;
1,2,3,4,4a,5-hexahydro-3-carbamoylmethyl-9-methylsulfonyl-pyrazo[2,1-c][1,4]benzoxazin-1-one;
1,2,3,4,4a,5-hexahydro-3-carbamoylmethyl-9-methylsulfonamido-pyrazo[2,1-c][1,4]benzoxazin-1-one;
1,2,3,4,4a,5-hexahydro-3-carbamoylmethyl-5-phenyl-pyrazo[2,1-c][1,4]benzoxazin-1-one;
1,2,3,4,4a,5-hexahydro-3-methyl-5-phenyl-pyrazo[2,1-c][1,4]benzoxazin-1-one;
1,2,3,4,4a,5-hexahydro-3-(2'-carbamoyl-ethyl)-5-phenyl-pyrazo[2,1-c][1,4]benzoxazin-1-one;
1,2,3,4,4a,5-hexahydro-3-(1'-carbamoyl-ethyl)-5-phenyl-pyrazo[2,1-c][1,4]benzoxazin-1-one;
1,2,3,4,4a,5-hexahydro-3-(1'-methyl-1'-carbamoyl-ethyl)-5-phenyl-pyrazo[2,1-c][1,4]benzoxazin-1-one;
1,2,3,4,4a,5-hexahydro-3-(2'-dimethylaminoethyl)-5-phenyl-pyrazo[2,1-c][1,4]benzoxazin-1-one;
1,2,3,4,4a,5-hexahydro-3-(3'-dimethylaminopropyl)-5-phenyl-pyrazo[2,1-c][1,4]benzoxazin-1-one;
1,2,3,4,4a,5-hexahydro-3-propargyl-5-phenyl-pyrazo[2,1-c][1,4]benzoxazin-1-one;
1,2,3,4,4a,5-hexahydro-3-benzyl-5-phenyl-pyrazo[2,1-c][1,4]benzoxazin-1-one;
1,2,3,4,4a,5-hexahydro-3-(p-methylsulfonyl-benzyl)-5-phenyl-pyrazo[2,1-c][1,4]benzoxazin-1-one;
1,2,3,4,4a,5-hexahydro-3-(3'-t-amylsulfonylpropyl)-5-phenyl-pyrazo[2,1-c][1,4]benzoxazin-1-one;
1,2,3,4,4a,5-hexahydro-3-carbamoylmethyl-5-phenyl-9-chloro-pyrazo[2,1-c][1,4]benzoxazin-1-one;
1,2,3,4,4a,5-hexahydro-3-carbamoylmethyl-5-phenyl-9-fluoro-pyrazo[2,1-c][1,4]benzoxazin-1-one;
1,2,3,4,4a,5-hexahydro-3-carbamoylmethyl-5-phenyl-9-methyl-pyrazo[2,1-c][1,4]benzoxazin-1-one;
1,2,3,4,4a,5-hexahydro-3-carbamoylmethyl-5-phenyl-9-trifluoromethyl-pyrazo[2,1-c][1,4]benzoxazin-1-one;
1,2,3,4,4a,5-hexahydro-3-carbamoylmethyl-5-phenyl-9-methoxy-pyrazo[2,1-c][1,4]benzoxazin-1-one;
1,2,3,4,4a,5-hexahydro-3-carbamoylmethyl-5-phenyl-9-carboxy-pyrazo[2,1-c][1,4]benzoxazin-1-one;
1,2,3,4,4a,5-hexahydro-3-carbamoylmethyl-5-phenyl-9-acetamido-pyrazo[2,1-c][1,4]benzoxazin-1-one;
1,2,3,4,4a,5-hexahydro-3-carbamoylmethyl-5-phenyl-9-methylsulfonyl-pyrazo[2,1-c][1,4]benzoxazin-1-one;
1,2,3,4,4a,5-hexahydro-3-carbamoylmethyl-5-phenyl-9-methylsulfonamido-pyrazo[2,1-c][1,4]benzoxazin-1-one.

EXAMPLE 41

A solution of 1,2,3,4,4a,5-hexahydro-3-trifluoroacetyl-pyrazo[2,1-c][1,4]benzoxazin-1-one (0.73 g; 2.44.10$^{-3}$ moles) in ethanol (30 ml) was reduced with a NaBH$_4$ excess for 1 hour under reflux, then poured in water and extracted with CH$_3$Cl so obtaining 1,2,3,4,4a,5-hexahydro-pyrazo[2,1-c][1,4]benzoxazin-1-one (0.43 g).

Analogously, the following compounds were obtained:
1,2,3,4,4a,5-hexahydro-9-chloro-pyrazo[2,1-c][1,4]benzoxazin-1-one;
1,2,3,4,4a,5-hexahydro-9-fluoro-pyrazo[2,1-c][1,4]benzoxazin-1-one;

1,2,3,4,4a,5-hexahydro-9-hydroxy-pyrazo[2,1-c][1,4]benzoxazin-1-one;
1,2,3,4,4a,5-hexahydro-9-amino-pyrazo[2,1-c][1,4]benzoxazin-1-one;
1,2,3,4,4a,5-hexahydro-9-methyl-pyrazo[2,1-c][1,4]benzoxazin-1-one;
1,2,3,4,4a,5-hexahydro-9-trifluoromethyl-pyrazo[2,1-c][1,4]benzoxazin-1-one;
1,2,3,4,4a,5-hexahydro-9-methoxy-pyrazo[2,1-c][1,4]benzoxazin-1-one;
1,2,3,4,4a,5-hexahydro-9-carboxy-pyrazo[2,1-c][1,4]benzoxazin-1-one;
1,2,3,4,4a,5-hexahydro-9-acetamido-pyrazo[2,1-c][1,4]benzoxazin-1-one;
1,2,3,4,4a,5-hexahydro-9-methylsulfonyl-pyrazo[2,1-c][1,4]benzoxazin-1-one;
1,2,3,4,4a,5-hexahydro-9-methylsulfonamido-pyrazo[2,1-c][1,4]benzoxazin-1-one;
1,2,3,4,4a,5-hexahydro-5-phenyl-pyrazo[2,1-c][1,4]benzoxazin-1-one;
1,2,3,4,4a,5-hexahydro-5-phenyl-9-chloro-pyrazo[2,1-c][1,4]benzoxazin-1-one;
1,2,3,4,4a,5-hexahydro-5-phenyl-9-fluoro-pyrazo[2,1-c][1,4]-benzoxazin-1-one;
1,2,3,4,4a,5-hexahydro-5-phenyl-9-hydroxy-pyrazo[2,1-c][1,4]benzoxazin-1-one;
1,2,3,4,4a,5-hexahydro-5-phenyl-9-amino-pyrazo[2,1-c][1,4]benzoxazin-1-one;
1,2,3,4,4a,5-hexahydro-5-phenyl-9-methyl-pyrazo[2,1-c][1,4]benzoxazin-1-one;
1,2,3,4,4a,5-hexahydro-5-phenyl-9-trifluoromethyl-pyrazo[2,1-c][1,4]benzoxazin-1-one;
1,2,3,4,4a,5-hexahydro-5-phenyl-9-methoxy-pyrazo[2,1-c][1,4]benzoxazin-1-one;
1,2,3,4,4a,5-hexahydro-5-phenyl-9-carboxy-pyrazo[2,1-c][1,4]benzoxazin-1-one;
1,2,3,4,4a,5-hexahydro-5-phenyl-9-acetamido-pyrazo[2,1-c][1,4]benzoxazin-1-one;
1,2,3,4,4a,5-hexahydro-5-phenyl-9-methylsulfonyl-pyrazo[2,1-c][1,4]benzoxazin-1-one;
1,2,3,4,4a,5-hexahydro-5-phenyl-9-methylsulfonamido-pyrazo[2,1-c][1,4]benzoxazin-1-one.

EXAMPLE 42

To a solution of 2H-3,4-dihydro-3-trifluoroacetylaminomethyl-4-chloroacetyl-[1,4]benzoxazine (2 g; $6.10^{-3}$ moles) in dimethylacetamide (50 ml), 50% NaH (0.6 g; $1.2.10^{-2}$ moles) was added and the solution brought to 60° C. for 2 hours, then water was added cautiously; the solution was extracted with ethyl acetate, dried on $Na_2SO_4$ and evaporated to dryness so obtaining an oil which, after elution on a silica gel column [benzene:acetone:diethylamine (150:50:2)], gave 1,2,3,4,4a,5-hexahydro-3-trifluoroacetyl-pyrazo[2,1-c][1,4]benzoxazin-1-one (1.1 g), as oil.

Analogously, the following compounds were obtained:
1,2,3,4,4a,5-hexahydro-3-trifluoroacetyl-9-chloro-pyrazo[2,1-c][1,4]benzoxazin-1-one;
1,2,3,4,4a,5-hexahydro-3-trifluoroacetyl-9-fluoro-pyrazo[2,1-c][1,4]benzoxazin-1-one;
1,2,3,4,4a,5-hexahydro-3-trifluoroacetyl-9-hydroxy-pyrazo[2,1-c][1,4]benzoxazin-1-one;
1,2,3,4,4a,5-hexahydro-3-trifluoroacetyl-9-amino-pyrazo[2,1-c][1,4]benzoxazin-1-one;
1,2,3,4,4a,5-hexahydro-3-trifluoroacetyl-9-methyl-pyrazo[2,1-c][1,4]benzoxazin-1-one;
1,2,3,4,4a,5-hexahydro-3-trifluoroacetyl-9-trifluoromethyl-pyrazo[2,1-c][1,4]benzoxazin-1-one;
1,2,3,4,4a,5-hexahydro-3-trifluoroacetyl-9-methoxy-pyrazo[2,1-c][1,4]benzoxazin-1-one;
1,2,3,4,4a,5-hexahydro-3-trifluoroacetyl-9-carboxy-pyrazo[2,1-c][1,4]benzoxazin-1-one;
1,2,3,4,4a,5-hexahydro-3-trifluoroacetyl-9-acetamido-pyrazo[2,1-c][1,4]benzoxazin-1-one;
1,2,3,4,4a,5-hexahydro-3-trifluoroacetyl-9-methylsulfonyl-pyrazo[2,1-c][1,4]benzoxazin-1-one;
1,2,3,4,4a,5-hexahydro-3-trifluoroacetyl-9-methylsulfonamido-pyrazo[2,1-c][1,4]benzoxazin-1-one;
1,2,3,4,4a,5-hexahydro-3-trifluoroacetyl-5-phenyl-pyrazo[2,1-c][1,4]benzoxazin-1-one;
1,2,3,4,4a,5-hexahydro-3-trifluoroacetyl-5-phenyl-9-chloro-pyrazo[2,1-c][1,4]benzoxazin-1-one;
1,2,3,4,4a,5-hexahydro-3-trifluoroacetyl-5-phenyl-9-fluoro-pyrazo[2,1-c][1,4]benzoxazin-1-one;
1,2,3,4,4a,5-hexahydro-3-trifluoroacetyl-5-phenyl-9-hydroxy-pyrazo[2,1-c][1,4]benzoxazin-1-one;
1,2,3,4,4a,5-hexahydro-3-trifluoroacetyl-5-phenyl-9-amino-pyrazo[2,1-c][1,4]benzoxazin-1-one;
1,2,3,4,4a,5-hexahydro-3-trifluoroacetyl-5-phenyl-9-methyl-pyrazo[2,1-c][1,4]benzoxazin-1-one;
1,2,3,4,4a,5-hexahydro-3-trifluoroacetyl-5-phenyl-9-trifluoromethyl-pyrazo[2,1-c][1,4]benzoxazin-1-one;
1,2,3,4,4a,5-hexahydro-3-trifluoroacetyl-5-phenyl-9-methoxy-pyrazo[2,1-c][1,4]benzoxazin-1-one;
1,2,3,4,4a,5-hexahydro-3-trifluoroacetyl-5-phenyl-9-carboxy-pyrazo[2,1-c][1,4]benzoxazin-1-one;
1,2,3,4,4a,5-hexahydro-3-trifluoroacetyl-5-phenyl-9-acetamido-pyrazo[2,1-c][1,4]benzoxazin-1-one;
1,2,3,4,4a,5-hexahydro-3-trifluoroacetyl-5-phenyl-9-methyl-pyrazo[2,1-c][1,4]benzoxazin-1-one;
1,2,3,4,4a,5-hexahydro-3-trifluoroacetyl-5-phenyl-9-methyl-pyrazo[2,1-c][1,4]benzoxazin-1-one.

EXAMPLE 43

A solution of 2H-3,4-dihydro-3-trifluoroacetamidomethyl-[1,4]benzoxazine (9.8 g; $3.76.10^{-2}$ moles) in anhydrous benzene (300 ml) was reacted with the stoichiometric amount of chloroacetylchloride (4.3 g) for 1 hour at 40° C. in the presence of an excess of $Na_2CO_2$. The resulting solution was washed with 5% $NaHCO_3$ and water, then dried on $Na_2SO_4$ and evaporated to dryness; by crystallization from ethyl acetate, 2H-3,4-dihydro-3-trifluoroacetamido-methyl-4-chloroacetyl-[1,4]benzoxazine (6.3 g) was obtained.

Analogously, the following compounds were obtained:
2H-3,4-dihydro-3-trifluoroacetamidomethyl-4-chloroacetyl-6-chloro-[1,4]benzoxazine;
2H-3,4-dihydro-3-trifluoroacetamidomethyl-4-chloroacetyl-6-fluoro-[1,4]benzoxazine;
2H-3,4-dihydro-3-trifluoroacetamidomethyl-4-chloroacetyl-6-hydroxy-[1,4]benzoxazine;
2H-3,4-dihydro-3-trifluoroacetamidomethyl-4-chloroacetyl-6-methyl-[1,4]benzoxazine;
2H-3,4-dihydro-3-trifluoroacetamidomethyl-4-chloroacetyl-6-trifluoromethyl-[1,4]benzoxazine;
2H-3,4-dihydro-3-trifluoroacetamidomethyl-4-chloroacetyl-6-methoxy-[1,4]benzoxazine;
2H-3,4-dihydro-3-trifluoroacetamidomethyl-4-chloroacetyl-6-carboxy-[1,4]benzoxazine;
2H-3,4-dihydro-3-trifluoroacetamidomethyl-4-chloroacetyl-6-acetamido-[1,4]benzoxazine;
2H-3,4-dihydro-3-trifluoroacetamidomethyl-4-chloroacetyl-6-methylsulfonyl-[1,4]benzoxazine;

2H-3,4-dihydro-3-trifluoroacetamidomethyl-4-chloroacetyl-6-methylsulfonamido-[1,4]benzoxazine;
2H-3,4-dihydro-2-phenyl-3-trifluoroacetamidomethyl-4-chloroacetyl-[1,4]benzoxazine;
2H-3,4-dihydro-2-phenyl-3-trifluoroacetamidomethyl-4-chloroacetyl-6-chloro-[1,4]benzoxazine;
2H-3,4-dihydro-2-phenyl-3-trifluoroacetamidomethyl-4-chloroacetyl-6-fluoro-[1,4]benzoxazine;
2H-3,4-dihydro-2-phenyl-3-trifluoroacetamidomethyl-4-chloroacetyl-6-hydroxy-[1,4]benzoxazine;
2H-3,4-dihydro-2-phenyl-3-trifluoroacetamidomethyl-4-chloroacetyl-6-methyl-[1,4]benzoxazine;
2H-3,4-dihydro-2-phenyl-3-trifluoroacetamidomethyl-4-chloroacetyl-6-trifluoromethyl-[1,4]benzoxazine;
2H-3,4-dihydro-2-phenyl-3-trifluoroacetamidomethyl-4-chloroacetyl-6-methoxy-[1,4]benzoxazine;
2H-3,4-dihydro-2-phenyl-3-trifluoroacetamidomethyl-4-chloroacetyl-6-carboxy-[1,4]benzoxazine;
2H-3,4-dihydro-2-phenyl-3-trifluoroacetamidomethyl-4-chloroacetyl-6-acetamido-[1,4]benzoxazine;
2H-3,4-dihydro-2-phenyl-3-trifluoroacetamidomethyl-4-chloroacetyl-6-methylsulfonyl-[1,4]benzoxazine;
2H-3,4-dihydro-2-phenyl-3-trifluoroacetamidomethyl-4-chloroacetyl-6-methylsulfonamido-[1,4]benzoxazine.

EXAMPLE 44

A solution of 2H-3,4-dihydro-3-benzylaminomethyl-4-(2',2'-diethoxy)-ethyl-[1,4]benzoxazine (5 g; $1.2 \cdot 10^{-2}$ moles) in glacial acetic acid (150 ml) was refluxed for 3 hours and 30 minutes. After evaporation to dryness, 3,4,4a,5-tetrahydro-3-benzyl-pyrazo[2,1-c][1,4]benzoxazine (3.6 g) was obtained as a T.L.C. pure oil.

Analogously, the following compounds were obtained:
3,4,4a,5-tetrahydro-3-methyl-pyrazo[2,1-c][1,4]benzoxazine;
3,4,4a,5-tetrahydro-3-carbamoylmethyl-pyrazo[2,1-c][1,4]benzoxazine;
3,4,4a,5-tetrahydro-3-(2'-carbamoyl-ethyl)-pyrazo[2,1-c][1,4]benzoxazine;
3,4,4a,5-tetrahydro-3-(1'-carbamoyl-ethyl)-pyrazo[2,1-c][1,4]benzoxazine;
3,4,4a,5-tetrahydro-3-(1'-methyl-1'-carbamoyl-ethyl)-pyrazo[2,1-c][1,4]benzoxazine;
3,4,4a,5-tetrahydro-3-(2'-dimethylaminoethyl)-pyrazo[2,1-c][1,4]benzoxazine;
3,4,4a,5-tetrahydro-3-(3'-dimethylaminopropyl)-pyrazo[2,1-c][1,4]benzoxazine;
3,4,4a,5-tetrahydro-3-propargyl-pyrazo[2,1-c][1,4]benzoxazine;
3,4,4a,5-tetrahydro-3-(p-methylsulfonyl-benzyl)-pyrazo[2,1-c][1,4]benzoxazine;
3,4,4a,5-tetrahydro-3-(3'-t-amylsulfonylpropyl)-pyrazo[2,1-c][1,4]benzoxazine;
3,4,4a,5-tetrahydro-3-carbamoylmethyl-9-chloro-pyrazo[2,1-c][1,4]benzoxazine;
3,4,4a,5-tetrahydro-3-carbamoylmethyl-9-fluoro-pyrazo[2,1-c][1,4]benzoxazine;
3,4,4a,5-tetrahydro-3-carbamoylmethyl-9-methyl-pyrazo[2,1-c][1,4]benzoxazine;
3,4,4a,5-tetrahydro-3-carbamoylmethyl-9-trifluoromethyl-pyrazo[2,1-c][1,4]benzoxazine;
3,4,4a,5-tetrahydro-3-carbamoylmethyl-9-methoxy-pyrazo[2,1-c][1,4]benzoxazine;
3,4,4a,5-tetrahydro-3-carbamoylmethyl-9-carboxy-pyrazo[2,1-c][1,4]-benzoxazine;
3,4,4a,5-tetrahydro-3-carbamoylmethyl-9-methylsulfonyl-pyrazo[2,1-c][1,4]benzoxazine;
3,4,4a,5-tetrahydro-3-benzyl-5-phenyl-pyrazo[2,1-c][1,4]benzoxazine;
3,4,4a,5-tetrahydro-3-methyl-5-phenyl-pyrazo[2,1-c][1,4]benzoxazine;
3,4,4a,5-tetrahydro-3-carbamoylmethyl-5-phenyl-pyrazo[2,1-c][1,4]benzoxazine;
3,4,4a,5-tetrahydro-3-(2'-carbamoyl-ethyl)-5-phenyl-pyrazo[2,1-c][1,4]benzoxazine;
3,4,4a,5-tetrahydro-3-(1'-carbamoyl-ethyl)-5-phenyl-pyrazo[2,1-c][1,4]benzoxazine;
3,4,4a,5-tetrahydro-3-(1'-methyl-1'-carbamoyl-ethyl)-5-phenyl-pyrazo[2,1-c][1,4]benzoxazine;
3,4,4a,5-tetrahydro-3-(2'-dimethylaminoethyl)-5-phenyl-pyrazo[2,1-c][1,4]benzoxazine;
3,4,4a,5-tetrahydro-3-(3'-dimethylaminopropyl)-5-phenyl-pyrazo[2,1-c][1,4]benzoxazine;
3,4,4a,5-tetrahydro-3-propargyl-5-phenyl-pyrazo[2,1-c][1,4]-benzoxazine;
3,4,4a,5-tetrahydro-3-(p-methylsulfonyl-benzyl)-5-phenyl-pyrazo[2,1-c][1,4]benzoxazine;
3,4,4a,5-tetrahydro-3-(3'-t-amylsulfonylpropyl)-5-phenyl-pyrazo[2,1-c][1,4]benzoxazine.

EXAMPLE 45

A solution of 2H-3,4-dihydro-3-(N-benzyl-N-trifluoroacetylaminomethyl)-4-(2',2'-diethoxy)-[1,4]benzoxazine (2.47 g; $5.3 \cdot 10^{-3}$ mole) in ethanol (40 ml) was reduced with an excess of NaBH$_4$ and refluxed for 1 hour, then poured in water and extracted with ethyl ether. The extract was dried up and concentrated so obtaining 2H-3,4-dihydro-3-benzylaminomethyl-4-(2',2'-diethoxyethyl-ethyl)-[1,4]benzoxazine, as a yellow oil.

Analogously, the following compounds were obtained:
2H-3,4-dihydro-3-methyl-4-(2',2'-diethoxy-ethyl)-[1,4]benzoxazine;
2H-3,4-dihydro-3-(2'-carbamoyl-ethyl)-4-(2',2'-diethoxy-ethyl)-[1,4]benzoxazine;
2H-3,4-dihydro-3-(1'-carbamoyl-ethyl)-4-(2',2'-diethoxy-ethyl)-[1,4]benzoxazine;
2H-3,4-dihydro-3-(1'-methyl-1'-carbamoyl-ethyl)-4-(2',2'-diethoxy-ethyl)-[1,4]benzoxazine;
2H-3,4-dihydro-3-(2'-dimethylaminoethyl)-4-(2',2'-diethoxy-ethyl)-[1,4]benzoxazine;
2H-3,4-dihydro-3-(3'-dimethylaminopropyl)-4-(2',2'-diethoxy-ethyl)-[1,4]benzoxazine;
2H-3,4-dihydro-3-propargyl-4-(2',2'-diethoxy-ethyl)-[1,4]benzoxazine;
2H-3,4-dihydro-3-benzyl-4-(2',2'-diethoxy-ethyl)-[1,4]benzoxazine;
2H-3,4-dihydro-3-(p-methylsulfonyl-benzyl)-4-(2',2'-diethoxy-ethyl)-[1,4]benzoxazine;
2H-3,4-dihydro-3-(3'-t-amylsulfonylpropyl)-4-(2',2'-diethoxy-ethyl)-[1,4]benzoxazine;
2H-3,4-dihydro-3-carbamoylmethyl-4-(2',2'-diethoxy-ethyl)-6-chloro-[1,4]benzoxazine;
2H-3,4-dihydro-3-carbamoylmethyl-4-(2',2'-diethoxy-ethyl)-6-fluoro-[1,4]benzoxazine;
2H-3,4-dihydro-3-carbamoylmethyl-4-(2',2'-diethoxy-ethyl)-6-methyl-[1,4]benzoxazine;
2H-3,4-dihydro-3-carbamoylmethyl-4-(2',2'-diethoxy-ethyl)-6-trifluoromethyl-[1,4]benzoxazine;
2H-3,4-dihydro-3-carbamoylmethyl-4-(2',2'-diethoxy-ethyl)-6-methoxy-[1,4]benzoxazine;

2H-3,4-dihydro-3-carbamoylmethyl-4-(2',2'-diethoxy-ethyl)-6-carboxy-[1,4]benzoxazine;
2H-3,4-dihydro-3-carbamoylmethyl-4-(2',2'-diethoxy-ethyl)-6-methylsulfonyl-[1,4]benzoxazine;
2H-3,4-dihydro-2-phenyl-3-benzylaminomethyl-4-(2',2'-diethoxy-ethyl)-[1,4]benzoxazine;
2H-3,4-dihydro-2-phenyl-3-methyl-4-(2',2'-diethoxy-ethyl)-[1,4]benzoxazine;
2H-3,4-dihydro-2-phenyl-3-carbamoylmethyl-4-(2',2'-diethoxy-ethyl)-[1,4]benzoxazine;
2H-3,4-dihydro-2-phenyl-3-(2'-carbamoyl-ethyl)-4-(2',2'-diethoxy-ethyl)-[1,4]benzoxazine;
2H-3,4-dihydro-2-phenyl-3-(1'-carbamoyl-ethyl)-4-(2',2'-diethoxy-ethyl)-[1,4]benzoxazine;
2H-3,4-dihydro-2-phenyl-3-(1'-methyl-1'-carbamoyl-ethyl)-4-(2',2'-diethoxy-ethyl)-[1,4]benzoxazine;
2H-3,4-dihydro-2-phenyl-3-(2'-dimethylaminoethyl)-4-(2',2'-diethoxy-ethyl)-[1,4]benzoxazine;
2H-3,4-dihydro-2-phenyl-3-(3'-dimethylaminopropyl)-4-(2',2'-diethoxy-ethyl)-[1,4]benzoxazine;
2H-3,4-dihydro-2-phenyl-3-propargyl-4-(2',2'-diethoxy-ethyl)-[1,4]benzoxazine;
2H-3,4-dihydro-2-phenyl-3-benzyl-4-(2',2'-diethoxy-ethyl)-[1,4]benzoxazine;
2H-3,4-dihydro-2-phenyl-3-(p-methylsulfonyl-benzyl)-4-(2',2'-diethoxy-ethyl)-[1,4]benzoxazine;
2H-3,4-dihydro-2-phenyl-3-(3'-t-amylsulfonylpropyl)-4-(2',2'-diethoxy-ethyl)-[1,4]benzoxazine.

EXAMPLE 46

To a solution of 2H-3,4-dihydro-3-(N-benzyl-N-trifluoroacetylaminomethyl)-[1,4]benzoxazine (23.5 g; $6.7.10^{-2}$ moles) in anhydrous dimethylformamide (150 ml), $Na_2CO_3$ (11 g; $8.10^{-2}$ moles) and bromo-acetaldehyde-diethylacetal (13.2 g; $6.7.10^{-2}$ moles) was added and the mixture stirred for 8 hours at 70° C. The solid was filtered off and the remaining solution evaporated to dryness so obtaining 2H-3,4-dihydro-3-(N-benzyl-N-trifluoroacetylaminomethyl)-4-(2',2'-diethoxy-ethyl)-[1,1]benzoxazine (14 g) as an oily residue.

Analogously, the following compounds were obtained:
2H-3,4-dihydro-3-methyl-4-(2',2'-diethoxy-ethyl)-[1,4]benzoxazine;
2H-3,4-dihydro-3-carbamoylmethyl-4-(2',2'-diethoxy-ethyl)-[1,4]benzoxazine;
2H-3,4-dihydro-3-(2'-carbamoyl-ethyl)-4-(2',2'-diethoxy-ethyl)-[1,4]benzoxazine;
2H-3,4-dihydro-3-(1'-carbamoyl-ethyl)-4-(2',2'-diethoxy-ethyl)-[1,4]benzoxazine;
2H-3,4-dihydro-3-(1'-methyl-1'-carbamoyl-ethyl)-4-(2',2'-diethoxy-ethyl)-[1,4]benzoxazine;
2H-3,4-dihydro-3-(2'-dimethylaminoethyl)-4-(2',2'-diethoxy-ethyl)-[1,4]benzoxazine;
2H-3,4-dihydro-3-(3'-dimethylaminopropyl)-4-(2',2'-diethoxy-ethyl)-[1,4]benzoxazine;
2H-3,4-dihydro-3-propargyl-4-(2',2'-diethoxy-ethyl)-[1,4]benzoxazine;
2H-3,4-dihydro-3-benzyl-4-(2',2'-diethoxy-ethyl)-[1,4]benzoxazine;
2H-3,4-dihydro-3-(p-methylsulfonyl-benzyl)-4-(2',2'-diethoxy-ethyl)-[1,4]benzoxazine;
2H-3,4-dihydro-3-(3'-t-amylsulfonylpropyl)-4-(2',2'-diethoxy-ethyl)-[1,4]benzoxazine;
2H-3,4-dihydro-3-carbamoylmethyl-4-(2',2'-diethoxy-ethyl)-6-chloro-[1,4]benzoxazine;
2H-3,4-dihydro-3-carbamoylmethyl-4-(2',2'-diethoxy-ethyl)-6-fluoro-[1,4]benzoxazine;
2H-3,4-dihydro-3-carbamoylmethyl-4-(2',2'-diethoxy-ethyl)-6-hydroxy-[1,4]benzoxazine;
2H-3,4-dihydro-3-carbamoylmethyl-4-(2',2'-diethoxy-ethyl)-6-methyl-[1,4]benzoxazine;
2H-3,4-dihydro-3-carbamoylmethyl-4-(2',2'-diethoxy-ethyl)-6-trifluoromethyl-[1,4]benzoxazine;
2H-3,4-dihydro-3-carbamoylmethyl-4-(2',2'-diethoxy-ethyl)-6-methoxy-[1,4]benzoxazine;
2H-3,4-dihydro-3-carbamoylmethyl-4-(2',2'-diethoxy-ethyl)-6-carboxy-[1,4]benzoxazine;
2H-3,4-dihydro-3-carbamoylmethyl-4-(2',2'-diethoxy-ethyl)-6-acetamido-[1,4]benzoxazine;
2H-3,4-dihydro-3-carbamoylmethyl-4-(2',2'-diethoxy-ethyl)-6-methylsulfonyl-[1,4]benzoxazine;
2H-3,4-dihydro-3-carbamoylmethyl-4-(2',2'-diethoxy-ethyl)-6-methylsulfonamido-[1,4]benzoxazine;
2H-3,4-dihydro-2-phenyl-3-(N-benzyl-N-trifluoroacetylaminomethyl)-4-(2',2'-diethoxy-ethyl)-[1,4]benzoxazine;
2H-3,4-dihydro-2-phenyl-3-methyl-4-(2',2'-diethoxy-ethyl)-[1,4]benzoxazine;
2H-3,4-dihydro-2-phenyl-3-(2'-carbamoyl-ethyl)-4-(2',2'-diethoxy-ethyl)-[1,4]benzoxazine;
2H-3,4-dihydro-2-phenyl-3-(1'-carbamoyl-ethyl)-4-(2',2'-diethoxy-ethyl)-[1,4]benzoxazine;
2H-3,4-dihydro-2-phenyl-3-(1'-methyl-1'-carbamoyl-ethyl)-4-(2',2'-diethoxy-ethyl)-[1,4]benzoxazine;
2H-3,4-dihydro-2-phenyl-3-(2'-dimethylaminoethyl)-4-(2',2'-diethoxy-ethyl)-[1,4]benzoxazine;
2H-3,4-dihydro-2-phenyl-3-(3'-dimethylaminopropyl)-4-(2',2'-diethoxy-ethyl)-[1,4]benzoxazine;
2H-3,4-dihydro-2-phenyl-3-propargyl-4-(2',2'-diethoxy-ethyl)-[1,4]benzoxazine;
2H-3,4-dihydro-2-phenyl-3-benzyl-4-(2',2'-diethoxy-ethyl)-[1,4]benzoxazine;
2H-3,4-dihydro-2-phenyl-3-(p-methylsulfonyl-benzyl)-4-(2',2'-diethoxy-ethyl)-[1,4]benzoxazine;
2H-3,4-dihydro-2-phenyl-3-(3'-t-amylsulfonylpropyl)-4-(2',2'-diethoxy-ethyl)-[1,4]benzoxazine.

EXAMPLE 47

Starting from 2H-3,4-dihydro-3-N-trifluoroacetylaminomethyl-[1,4]benzoxazine (2.60 g; $1.10^{-2}$ moles) and proceeding as described in example 1, 2H-3,4-dihydro-3-(N-benzyl-N-trifluoroacetylaminomethyl)-[1,4]benzoxazine (2.4 g) was obtained.

Analogously, the following compounds were obtained:
2H-3,4-dihydro-3-(N-methyl-N-trifluoroacetylaminomethyl)-[1,4]benzoxazine;
2H-3,4-dihydro-3-(N-carbamoylmethyl-N-trifluoroacetylaminomethyl)-[1,4]benzoxazine;
2H-3,4-dihydro-3-[N-(2'-carbamoyl-ethyl)-N-trifluoroacetylaminomethyl]-[1,4]benzoxazine;
2H-3,4-dihydro-3-[N-(1'-carbamoyl-ethyl)-N-trifluoroacetylaminomethyl]-[1,4]benzoxazine;
2H-3,4-dihydro-3-[N-(1'-methyl-1'-carbamoyl-ethyl)-N-trifluoroacetylaminomethyl]-[1,4]benzoxazine;
2H-3,4-dihydro-3-[N-(2'-dimethylaminoethyl)-N-trifluoroacetylaminomethyl]-[1,4]benzoxazine;
2H-3,4-dihydro-3-[N-(3'-dimethylaminopropyl)-N-trifluoroacetylaminomethyl]-[1,4]benzoxazine;
2H-3,4-dihydro-3-(N-propargyl-N-trifluoroacetylaminomethyl)-[1,4]benzoxazine;
2H-3,4-dihydro-3-[N-(p-methylsulfonyl-benzyl)-N-trifluoroacetylaminomethyl]-[1,4]benzoxazine;

2H-3,4-dihydro-3-[N-(3'-t-amylsulfonylpropyl)-N-trifluoroacetylaminomethyl]-[1,4]benzoxazine;
2H-3,4-dihydro-2-phenyl-3-(N-benzyl-N-trifluoroacetylaminomethyl)-[1,4]benzoxazine;
2H-3,4-dihydro-2-phenyl-3-(N-methyl-N-trifluoroacetylaminomethyl)-[1,4]benzoxazine;
2H-3,4-dihydro-2-phenyl-3-(N-carbamoylmethyl-N-trifluoroacetylaminomethyl)-[1,4]benzoxazine;
2H-3,4-dihydro-2-phenyl-3-[N-(2'-carbamoyl-ethyl)-N-trifluoroacetylaminomethyl]-[1,4]benzoxazine;
2H-3,4-dihydro-2-phenyl-3-[N-(1'-carbamoyl-ethyl)-N-trifluoroacetylaminomethyl]-[1,4]benzoxazine;
2H-3,4-dihydro-2-phenyl-3-[N-(1'-methyl-1'-carbamoyl-ethyl)-N-trifluoroacetylaminomethyl]-[1,4]benzoxazine;
2H-3,4-dihydro-2-phenyl-3-[N-(2'-dimethylaminoethyl)-N-trifluoroacetylaminomethyl]-[1,4]benzoxazine;
2H-3,4-dihydro-2-phenyl-3-[N-(3'-dimethylaminopropyl)-N-trifluoroacetylaminomethyl]-[1,4]-benzoxazine;
2H-3,4-dihydro-2-phenyl-3-(N-propargyl-N-trifluoroacetylaminomethyl)-[1,4]benzoxazine;
2H-3,4-dihydro-2-phenyl-3-[N-(p-methylsulfonyl-benzyl)-N-trifluoroacetylaminomethyl]-[1,4]benzoxazine;
2H-3,4-dihydro-2-phenyl-3-[N-(3'-t-amylsulfonylpropyl)-N-trifluoroacetylaminomethyl]-[1,4]benzoxazine;
2H-3,4-dihydro-3-(N-carbamoylmethyl-N-trifluoroacetylaminomethyl)-6-chloro-[1,4]benzoxazine;
2H-3,4-dihydro-3-(N-carbamoylmethyl-N-trifluoroacetylaminomethyl)-6-fluoro-[1,4]benzoxazine;
2H-3,4-dihydro-3-(N-carbamoylmethyl-N-trifluoroacetylaminomethyl)-6-hydroxy-[1,4]benzoxazine;
2H-3,4-dihydro-3-(N-carbamoylmethyl-N-trifluoroacetylaminomethyl)-6-amino-[1,4]benzoxazine;
2H-3,4-dihydro-3-(N-carbamoylmethyl-N-trifluoroacetylaminomethyl)-6-methyl-[1,4]benzoxazine;
2H-3,4-dihydro-3-(N-carbamoylmethyl-N-trifluoroacetylaminomethyl)-6-trifluoromethyl-[1,4]benzoxazine;
2H-3,4-dihydro-3-(N-carbamoylmethyl-N-trifluoroacetylaminomethyl)-6-methoxy-[1,4]benzoxazine;
2H-3,4-dihydro-3-(N-carbamoylmethyl-N-trifluoroacetylaminomethyl)-6-carboxy-[1,4]benzoxazine;
2H-3,4-dihydro-3-(N-carbamoylmethyl-N-trifluoroacetylaminomethyl)-6-acetamido-[1,4]benzoxazine;
2H-3,4-dihydro-3-(N-carbamoylmethyl-N-trifluoroacetylaminomethyl)-6-methylsulfonyl-[1,4]benzoxazine;
2H-3,4-dihydro-3-(N-carbamoylmethyl-N-trifluoroacetylaminomethyl)-6-methylsulfonamido-[1,4]benzoxazine.

EXAMPLE 48

To a solution of 1H,2,3,3a,4-tetrahydro-2-carbamoylmethyl-imidazo[5,1-c][1,4]benzoxazin-1-one (1 g; $4.10^{-3}$ moles) in benzene (50 ml), $P_2S_5$ (0.46 g; $2.10^{-3}$ moles) was added. The mixture was refluxed 1 hour and 30 minutes then cooled poured in water and the organic phases removed. The aqueous phase was extracted many times with chloroform; the chloroform extracts were collected, dried on $Na_2SO_4$ and evaporated to dryness. The residue, after elution on silica gel column [benzene:acetone:diethylamine (150:50:2)], gave 1H,2,3,3a,4-tetrahydro-2-carbamoyl-methyl-imidazo[5,1-c][1,4]benzoxazin-1-thione (0.55 g), m.p. 230°–232° C. (dec.).

Analogously, the following compounds were obtained:
1H,2,3,3a,4-tetrahydro-2-methyl-imidazo[5,1-c][1,4]benzoxazin-1-thione;
1H,2,3,3a,4-tetrahydro-2-(2'-carbamoyl-ethyl)-imidazo[5,1-c][1,4]benzoxazin-1-thione;
1H,2,3,3a,4-tetrahydro-2-(1'-carbamoyl-ethyl)-imidazo[5,1-c][1,4]benzoxazin-1-thione;
1H,2,3,3a,4-tetrahydro-2-(1'-methyl-1'-carbamoyl-ethyl)-imidazo[5,1-c][1,4]benzoxazin-1-thione;
1H,2,3,3a,4-tetrahydro-2-(2'-dimethylaminoethyl)-imidazo[5,1-c][1,4]benzoxazin-1-thione;
1H,2,3,3a,4-tetrahydro-2-(3'-dimethylaminopropyl)-imidazo[5,1-c][1,4]benzoxazin-1-thione;
1H,2,3,3a,4-tetrahydro-2-propargyl-imidazo[5,1-c][1,4]benzoxazin-1-thione;
1H,2,3,3a,4-tetrahydro-2-benzyl-imidazo[5,1-c][1,4]benzoxazin-1-thione;
1H,2,3,3a,4-tetrahydro-2-(p-methylsulfonyl-benzyl)-imidazo[5,1-c][1,4]benzoxazin-1-thione;
1H,2,3,3a,4-tetrahydro-2-(3'-t-amylsulfonylpropyl)-imidazo[5,1-c][1,4]benzoxazin-1-thione;
1H,2,3,3a,4-tetrahydro-2-carbamoylmethyl-8-chloro-imidazo[5,1-c][;b 1,4]benzoxazin-1-thione;
1H,2,3,3a,4-tetrahydro-2-carbamoylmethyl-8-fluoro-imidazo[5,1-c][1,4]benzoxazin-1-thione;
1H,2,3,3a,4-tetrahydro-2-carbamoylmethy-8-hydroxy-imidazo[5,1-c][1,4]benzoxazin-1-thione;
1H,2,3,3a,4-tetrahydro-2-carbamoylmethyl-8-amino-imidazo[5,1-c][1,4]benzoxazin-1-thione;
1H,2,3,3a,4-tetrahydro-2-carbamoylmethyl-8-methyl-imidazo[5,1-c][1,4]benzoxazin-1-thione;
1H,2,3,3a,4-tetrahydro-2-carbamoylmethyl-8-trifluoromethyl-imidazo[5,1-c][1,4]benzoxazin-1-thione;
1H,2,3,3a,4-tetrahydro-2-carbamoylmethyl-8-methoxy-imidazo[5,1-c][1,4]benzoxazin-1-thione;
1H,2,3,3a,4-tetrahydro-2-carbamoylmethyl-8-carboxy-imidazo[5,1-c][1,4]benzoxazin-1-thione;
1H,2,3,3a,4-tetrahydro-2-carbamoylmethyl-8-acetamido-imidazo[5,1-c][1,4]benzoxazin-1-thione;
1H,2,3,3a,4-tetrahydro-2-carbamoylmethyl-8-methylsulfonyl-imidazo[5,1-c][1,4]benzoxazin-1-thione;
1H,2,3,3a,4-tetrahydro-2-carbamoylmethyl-8-methylsulfonamido-imidazo[5,1-c][1,4]benzoxazin-1-thione;
1H-2,3,3a,4-tetrahydro-2-carbamoylmethyl-imidazo[5,1-c][1,4]benzothiazin-1-thione;
1H,2,3,3a,4-tetrahydro-2-methyl-imidazo[5,1-c][1,4]benzothiazin-1-thione;
1H,2,3,3a,4-tetrahydro-2-(2'-carbamoyl-ethyl)-imidazo[5,1-c][1,4]benzothiazin-1-thione;
1H,2,3,3a,4-tetrahydro-2-(1'-carbamoyl-ethyl)-imidazo[5,1-c][1,4]benzothiazin-1-thione;
1H,2,3,3a,4-tetrahydro-2-(1'-methyl-1'-carbamoyl-ethyl)-imidazo[5,1-c][1,4]benzothiazin-1-thione;
1H,2,3,3a,4-tetrahydro-2-(2'-dimethylaminoethyl)-imidazo[5,1-c][1,4]benzothiazin-1-thione;
1H,2,3,3a,4-tetrahydro-2-(3'-dimethylaminopropyl)-imidazo[5,1-c][1,4]benzothiazin-1-thione;
1H,2,3,3a,4-tetrahydro-2-propargyl-imidazo[5,1-c][1,4]benzothiazin-1-thione;

1H,2,3,3a,4-tetrahydro-2-benzyl-imidazo[5,1-c][1,4]benzothiazin-1-thione;

1H,2,3,3a,4-tetrahydro-2-(p-methylsulfonyl-benzyl)-imidazo[5,1-c][1,4]benzothiazin-1-thione;

1H,2,3,3a,4-tetrahydro-2-(3'-t-amylsulfonylpropyl)-imidazo[5,1-c][1,4]benzothiazin-1-thione;

1H,2,3,3a,4-tetrahydro-2-carbamoylmethyl-8-chloro-imidazo[5,1-c][1,4]benzothiazin-1-thione;

1H,2,3,3a,4-tetrahydro-2-carbamoylmethyl-8-fluoro-imidazo[5,1-c][1,4]benzothiazin-1-thione;

1H,2,3,3a,4-tetrahydro-2-carbamoylmethyl-8-hydroxy-imidazo[5,1-c][1,4]benzothiazin-1-thione;

1H,2,3,3a,4-tetrahydro-2-carbamoylmethyl-8-amino-imidazo[5,1-c][1,4]benzothiazin-1-thione;

1H,2,3,3a,4-tetrahydro-2-carbamoylmethyl-8-methyl-imidazo[5,1-c][1,4]benzothiazin-1-thione;

1H-2,3,3a,4-tetrahydro-2-carbamoylmethyl-8-trifluoromethyl-imidazo[5,1-c][1,4]benzothiazin-1-thione;

1H,2,3,3a,4-tetrahydro-2-carbamoylmethyl-8-methoxy-imidazo[5,1-c][1,4]benzothiazin-1-thione;

1H,2,3,3a,4-tetrahydro-2-carbamoylmethyl-8-carboxy-imidazo[5,1-c][1,4]benzothiazin-1-thione;

1H,2,3,3a,4-tetrahydro-2-carbamoylmethyl-8-acetamido-imidazo[5,1-c][1,4]benzothiazin-1-thione;

1H,2,3,3a,4-tetrahydro-2-carbamoylmethyl-8-methylsulfonyl-imidazo[5,1-c][1,4]benzothiazin-1-thione;

1H,2,3,3a,4-tetrahydro-2-carbamoylmethyl-8-methylsulfonamido-imidazo[5,1-c][1,4]benzothiazin-1-thione;

1H,2,3,3a,4-tetrahydro-2-carbamoylmethyl-3a-phenyl-imidazo[5,1-c][1,4]benzoxazin-1-thione;

1H,2,3,3a,4-tetrahydro-2-carbamoylmethyl-4-phenyl-imidazo[5,1-c][1,4]benzoxazin-1-thione;

1H,2,3,3a,4-tetrahydro-2-carbamoylmethyl-4,4-dimethyl-imidazo[5,1-c][1,4]benzoxazin-1-thione;

1H,2,3,3a,4-tetrahydro-2-carbamoylmethyl-3a-phenyl-imidazo[5,1-c][1,4]benzothiazin-1-thione;

1H,2,3,3a,4-tetrahydro-2-carbamoylmethyl-4-phenyl-imidazo[5,1-c][1,4-benzothiazin-1-thione;

1H,2,3,3a,4-tetrahydro-2-carbamoylmethyl-4,4-dimethyl-imidazo[5,1-c][1,4]benzothiazin-1-thione.

EXAMPLE 49

To a solution of 1H,2,3,3a,4-tetrahydro-2-carbamoylmethyl-imidazo[5,1-c][1,4]benzoxazin-1-one (1 g; 4.10$^{-3}$ moles) in toluene (50 ml), P$_2$S$_5$ (0.92 g; 1.10$^{-3}$ moles) was added. The mixture was refluxed for 1 hour, then cooled and poured in water and the organic phase evaporated. By proceeding as described in example 43 also as regards the elution on silica gel column, 1H,2,3,3a,4-tetrahydro-2-thiocarbamoylmethyl-imidazo[5,1-c][1,4]benzoxazin-1-thione (0.36 g), was obtained.

Analogously, the following compounds were obtained:

1H,2,3,3a,4-tetrahydro-2-(2'-thiocarbamoyl-ethyl)-imidazo[5,1-c][1,4]benzoxazin-1-thione;

1H,2,3,3a,4-tetrahydro-2-(1'-thiocarbamoyl-ethyl)-imidazo[5,1-c][1,4]benzoxazin-1-thione;

1H,2,3,3a,4-tetrahydro-2-(1'-methyl-1'-thiocarbamoyl-ethyl)-imidazo[5,1-c][1,4]benzoxazin-1-thione;

1H,2,3,3a,4-tetrahydro-2-thiocarbamoylmethyl-8-chloro-imidazo[5,1-c][1,4]benzoxazin-1-thione;

1H,2,3,3a,4-tetrahydro-2-thiocarbamoylmethyl-8-fluoro-imidazo[5,1-c][1,4]benzoxazin-1-thione;

1H,2,3,3a,4-tetrahydro-2-thiocarbamoylmethyl-8-hydroxy-imidazo[5,1-c][1,4]benzoxazin-1-thione;

1H,2,3,3a,4-tetrahydro-2-thiocarbamoylmethyl-8-amino-imidazo[5,1-c][1,4]benzoxazin-1-thione;

1H,2,3,3a,4-tetrahydro-2-thiocarbamoylmethyl-8-methyl-imidazo[5,1-c][1,4]benzoxazin-1-thione;

1H,2,3,3a,4-tetrahydro-2-thiocarbamoylmethyl-8-trifluoromethyl-imidazo[5,1-c][1,4]benzoxazin-1-thione;

1H,2,3,3a,4-tetrahydro-2-thiocarbamoylmethyl-8-methoxy-imidazo[5,1-c][1,4]benzoxazin-1-thione;

1H,2,3,3a,4-tetrahydro-2-thiocarbamoylmethyl-8-carboxy-imidazo[5,1-c][1,4]benzoxazin-1-thione;

1H,2,3,3a,4-tetrahydro-2-thiocarbamoylmethyl-8-acetamido-imidazo[5,1-c][1,4]benzoxazin-1-thione;

1H,2,3,3a,4-tetrahydro-2-thiocarbamoylmethyl-8-methylsulfonyl-imidazo[5,1-c][1,4]benzoxazin-1-thione;

1H,2,3,3a,4-tetrahydro-2-thiocarbamoylmethyl-8-methylsulfonamido-imidazo[5,1-c][1,4]benzoxazin-1-thione;

1H,2,3,3a,4-tetrahydro-2-thiocarbamoylmethyl-imidazo[5,1-c][1,4]benzoxazin-1-thione;

1H,2,3,3a,4-tetrahydro-2-(2'-thiocarbamoyl-ethyl)-imidazo[5,1-c][1,4]benzoxazin-1-thione;

1H,2,3,3a,4-tetrahydro-2-(1'-thiocarbamoyl-ethyl)-imidazo[5,1-c][1,4]benzoxazin-1-thione;

1H,2,3,3a,4-tetrahydro-2-(1'-methyl-1'-thiocarbamoylethyl)-imidazo[5,1-c][1,4]benzothiazin-1-thione;

1H,2,3,3a,4-tetrahydro-2-thiocarbamoylmethyl-8-chloro-imidazo[5,1-c][1,4]benzothiazin-1-thione;

1H,2,3,3a,-tetrahydro-2-thiocarbamoylmethyl-8-fluoro-imidazo[5,1-c][1,4]benzothiazin-1-one;

1H,2,3,3a,4-tetrahydro-2-thiocarbamoylmethyl-8-hydroxy-imidazo[5,1-c][1,4]benzothiazin-1-thione;

1H,2,3,3a,4-tetrahydro-2-thiocarbamoylmethyl-8-amino-imidazo[5,1-c][1,4]benzothiazin-1-thione;

1H,2,3,3a,4-tetrahydro-2-thiocarbamoylmethyl-8-methyl-imidazo[5,1-c][1,4]benzothiazin-1-thione;

2H,2,3,3a,4-tetrahydro-2-thiocarbamoylmethyl-8-trifluoromethyl-imidazo[5,1-c][1,4]benzothiazin-1-thione;

1H, 2,3,3a,4-tetrahydro-2-thiocarbamoylmethyl-8-methoxy-imidazo[5,1-c][1,4]benzothiazin-1thione;;

1H,2,3,3a,4-tetrahydro-2-thiocarbamoylmethyl-8-carboxy-imidazo[5,1-c][1,4]benzothiazin-1-thione;

1H,2,3,3a,4-tetrahydro-2-thiocarbamoylmethyl-8-acetamidoimidazo[5,1-c][1,4]benzothiazin-1-thione;

1H,2,3,3a,4-tetrahydro-2-thiocarbamoylmethyl-8-methylsulfonyl-imidazo[5,1-c][1,4]benzothiazin-1-thione;

1H,2,3,3a,4-tetrahydro-2-thiocarbamoylmethyl-8-methylsulfonamido-imidazo[5,1-c][1,4]benzothiazin-1-thione;

1H,2,3,3a,4-tetrahydro-2-thiocarbamoylmethyl-3a-phenylimidazo[5,1-c][1,4]benzoxazin-1-thione;

1H,2,3,3a,4-tetrahydro-2-thiocarbamoylmethyl-4-phenylimidazo[5,1-c][1,4]benzoxazin-1-thione;

1H-2,3,3a,4-tetrahydro-2-thiocarbamoylmethyl-4,4-dimethylimidazo[5,1-c][1,4]benzoxazin-1-thione;

1H,2,3,3a,4-tetrahydro-2-thiocarbamoylmethyl-3a-phenylimidazo[5,1-c][1,4-benzothiazin-1-thione;

1H,2,3,3a,4-tetrahydro-2-thiocarbamoylmethyl-4-phenylimidazo[5,1-c][1,4]benzothiazin-1-thione;

1H,2,3,3a,4-tetrahydro-2-thiocarbamoylmethyl-4,4-dimethylimidazo[5,1-c][1,4]benzothiazin-1-thione.

We claim:

1. Compound of the formula

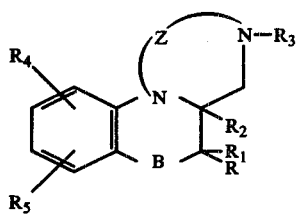

(I)

wherein

B is an oxygen atom;

R and $R_1$ are independently selected from the group consisting of hydrogen, $C_1$-$C_6$ alkyl and

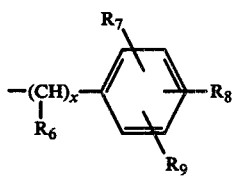

wherein x is zero or an integer of 1 to 6, $R_6$ is hydrogen or $C_1$-$C_6$ alkyl and $R_7$, $R_8$ and $R_9$ are independently selected from the group consisting of hydrogen, halogen, $C_1$-$C_6$ alkyl, $C_1$-$C_6$ trihaloalkyl, hydroxy, carboxy and one of the radicals —$OR_{10}$, —$SO_2R_{10}$ and —$COOR_{10}$, wherein $C_1$-$C_6$ alkyl; $R_2$ is hydrogen, $C_1$-$C_6$ alkyl or

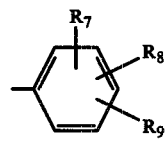

wherein $R_7$, $R_8$ and $R_9$ are as defined above; $R_3$ is hydrogen; carbamoyl; thiocarbamoyl; $C_1$-$C_6$ alkyl, $C_2$-$C_6$ alkenyl or $C_2$-$C_6$ alkynyl, each of the alkyl, alkenyl and alkynyl groups being unsubstituted or substituted by one or more substituents selected from the group consisting of (a) halogen; (b) carboxy; (c) hydroxy; (d) $C_1$-$C_6$ alkoxy; (e) one of the radicals —$SO_2R_{11}$, —$COOR_{11}$, and —$COR_{11}$, wherein $R_{11}$ is $C_1$-$C_6$ alkyl or

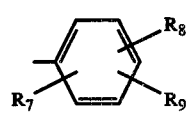

wherein $R_7$, $R_8$ and $R_9$ are as defined above;

(f)

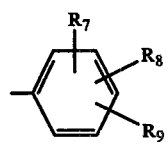

wherein $R_7$, $R_8$ and $R_9$ are as defined above; (g) one of the radicals

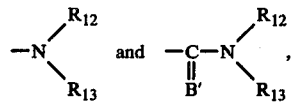

wherein B' is an oxygen or sulfur atom and $R_{12}$ and $R_{13}$ are independently selected from the group consisting of hydrogen and $C_1$-$C_6$ alkyl; $R_4$ and $R_5$ are independently selected from the group consisting of hydrogen; halogen; amino; $C_1$-$C_6$ alkanoylamino; $C_1$-$C_6$ alkyl; $C_1$-$C_6$ trihaloalkyl; hydroxy; carboxy; $C_1$-$C_6$ alkoxy; $R_{10}$—$SO_2$—NH—, wherein $R_{10}$ is as defined above; one of the radicals —$SO_2R_{11}$ and —$COOR_{11}$, wherein $R_{11}$ is as defined above; or $R_4$ and $R_5$, taken together with two adjacent carbon atoms of the benzene ring, form a carbocyclic ring; Z is >C=B, wherein B is as defined above; as well as the pharmaceutically acceptable salts thereof.

2. A method of treating depression in a patient in need of such treatment, said method comprising administering to said patient a therapeutically effective amount of a compound of claim 1.

3. A pharmaceutical composition comprising a compound according to claim 1 and a pharmaceutically acceptable carrier therefor.

4. Composition of claim 3, wherein said compound is 1H,2,3,3a,4-tetrahydro-2-carbamoylmethyl-imidazo[5,1-c][1,4]benzoxazin-1-one.

5. Composition of claim 3, wherein said compound is 1H,2,3,3a,4-tetrahydro-2-carbamoylmethyl-8-chloro-imidazo[5,1-c][1,4]benzoxazin-1-one.

6. Compound of the formula (II)

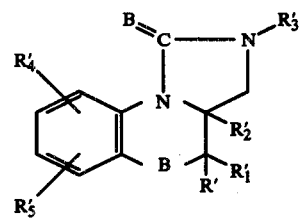

(II)

wherein B is an oxygen atom;

R' and $R'_1$ are independently selected from the group consisting of hydrogen, $C_1$-$C_6$ alkyl and

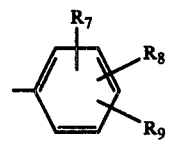

wherein $R_7$, $R_8$ and $R_9$ are as defined in claim 1; $R'_2$ is hydrogen, $C_1$-$C_6$ alkyl or

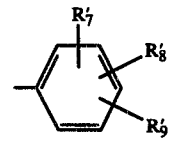

wherein $R'_7$, $R'_8$ and $R'_9$ are independently selected from the group consisting of hydrogen, halogen, $C_1$-$C_6$ alkyl, trifluoromethyl, hydroxy, and $C_1$-$C_6$ alkoxy; $R'_3$ is hydrogen or $C_1$-$C_6$ alkyl, unsubstituted or substituted by one or more substituents selected from the group consisting of (a') carboxy; (b') hydroxy; (c') $C_1$-$C_6$ alkoxy; (d') —$COOR_{10}$, wherein $R_{10}$ is as defined in claim 1

(e')

wherein $R_7$, $R_8$ and $R_9$ are as defined in claim 1; and
(f') one of the radicals $$-N\begin{matrix}R'_{12}\\R'_{13}\end{matrix} \quad \text{and} \quad -\underset{\underset{B'}{\|}}{C}-N\begin{matrix}R'_{12}\\R'_{13}\end{matrix}$$

wherein B' is as defined in claim 1, and $R'_{12}$ and $R'_{13}$ are independently selected from the group consisting of hydrogen and $C_1$-$C_6$ alkyl;
$R'_4$ and $R'_5$ are independently selected from the group consisting of hydrogen, halogen, amino, $C_1$-$C_6$ alkanoylamino, trifluoromethyl, hydroxy, carboxy, $C_1$-$C_6$ alkyl, $C_1$-$C_6$ alkoxy and one of the radicals $R_{10}$—$SO_2$—NH— and —$SO_2R_{11}$, wherein $R_{10}$ and $R_{11}$ are as defined in claim 1; and the pharmaceutically acceptable salts thereof.

7. A pharmaceutical composition comprising a compound according to claim 6, and a pharmaceutically acceptable carrier therefor.

8. Compound of the formula (III)

(III)

wherein B is oxygen, and $R'_2$ is as defined in claim 6; R'' and $R''_1$ are independently selected from the group consisting of hydrogen, $C_1$-$C_6$ alkyl, and wherein $R'_7$, $R'_8$ and $R'_9$ are as defined in claim 6; $R''_3$ is hydrogen or $C_1$-$C_6$ alkyl, unsubstituted or substituted by one or more substituents selected from the group consisting of (a'') carboxy; (b'') hydroxy; (c'') $C_1$-$C_6$ alkoxy; (d'') —$COOR_{10}$, wherein $R_{10}$ is $C_1$-$C_6$ alkyl; and (e'') one of the radicals $$-N\begin{matrix}R''_{12}\\R''_{13}\end{matrix} \quad \text{and} \quad -\underset{\underset{B'}{\|}}{C}-N\begin{matrix}R''_{12}\\R''_{13}\end{matrix}$$

wherein B' is an oxygen or sulfur atom and $R''_{12}$ and $R''_{13}$ are independently selected from the group consisting of hydrogen and $C_1$-$C_6$ alkyl; $R''_4$ and $R''_5$ are independently selected from the group consisting of hydrogen, halogen, amino, acetamido, trifluoromethyl, hydroxy, carboxy, $C_1$-$C_6$ alkyl, $C_1$-$C_6$ alkoxy, $CH_3$-$SO_2$-NH— and —$SO_2$—$R'_{11}$, wherein $R'_{11}$ is $C_1$-$C_6$ alkyl or wherein $R'_7$, $R'_8$ and $R'_9$ are as defined in claim 6; as well as the pharmaceutically acceptable salts thereof.

9. A pharmaceutical composition comprising a compound according to claim 8, and a pharmaceutically acceptable carrier therefor.

10. 1H,2,3,3a,4-tetrahydro-2-carbamoylmethyl-imidazo[5,1-c][1,4]benzoxazin-1-one; and pharmaceutically acceptable salts thereof.

11. 1H,2,3,3a,4-tetrahydro-2-methyl-imidazo[5,1-c][1,4]benzoxazin-1-one, as claimed in claim 1, and pharmaceutically acceptable salts thereof.

12. 1H,2,3,3a,4-tetrahydro-2-(2'-carbamoyl-ethyl)-imidazo[5,1-c][1,4]benzoxazin-1-one, as claimed in claim 1, and pharmaceutically acceptable salts thereof.

13. 1H,2,3,3a,4-tetrahydro-2-(1'-carbamoyl-ethyl)-imidazo[5,1-c][1,4]benzoxazin-1-one, as claimed in claim 1, and pharmaceutically acceptable salts thereof.

14. 1H,2,3,3a,4-tetrahydro-2-(1'-methyl-1'-carbamoyl-ethyl)-imidazo[5,1-c][1,4]benzoxazin-1-one, as claimed in claim 1, and pharmaceutically acceptable salts thereof.

15. 1H,2,3,3a,4-tetrahydro-2-(2'-dimethylaminoethyl)-imidazo[5,1-c][1,4]benzoxazin-1-one, as claimed in claim 1, and pharmaceutically acceptable salts thereof.

16. 1H,2,3,3a,4-tetrahydro-2-(3'-dimethylaminopropyl)-imidazo[5,1-c][1,4]benzoxazin-1-one, as claimed in claim 1, and pharmaceutically acceptable salts thereof.

17. 1H,2,3,3a,4-tetrahydro-2-carbamoylmethyl-8-chloro-imidazo[5,1-c][1,4]benzoxazin-1-one, and pharmaceutically acceptable salts thereof.

18. 1H,2,3,3a,4-tetrahydro-2-(2'-carbamoyl-ethyl)-8-chloro-imidazo[5,1-c][1,4]benzoxazin-1-one, as claimed in claim 1, and pharmaceutically acceptable salts thereof.

19. 1H,2,3,3a,4-tetrahydro-2-carbamoylmethyl-8-fluoro-imidazo[5,1-c][1,4]benzoxazin-1-one, as claimed in claim 1, and pharmaceutically acceptable salts thereof.

20. 1H,2,3,3a,4-tetrahydro-2-carbamoylmethyl-8-hydroxy-imidazo[5,1-c][1,4]benzoxazin-1-one, as claimed in claim 1, and pharmaceutically acceptable salts thereof.

21. 1H,2,3,3a,4-tetrahydro-2-carbamoylmethyl-8-amino-imidazo[5,1-c][1,4]benzoxazin-1-one, as claimed in claim 1, and pharmaceutically acceptable salts thereof.

22. 1H,2,3,3a,4-tetrahydro-2-carbamoylmethyl-8-methyl-imidazo[5,1-c][1,4]benzoxazin-1-one, as claimed in claim 1, and pharmaceutically acceptable salts thereof.

23. 1H,2,3,3a,4-tetrahydro-2-carbamoylmethyl-8-trifluoromethyl-imidazo[5,1-c][1,4]benzoxazin-1-one, as claimed in claim 1, and pharmaceutically acceptable salts thereof.

24. 1H,2,3,3a,4-tetrahydro-2-carbamoyl-8-methoxy-imidazo[5,1-c][1,4]benzoxazin-1-one, as claimed in claim 1, and pharmaceutically acceptable salts thereof.

25. 1H,2,3,3a,4-tetrahydro-2-carbamoylmethyl-8-carboxy-imidazo[5,1-c][1,4]benzoxazin-1-one, as claimed in claim 1, and pharmaceutically acceptable salts thereof.

26. 1H,2,3,3a,4-tetrahydro-2-carbamoylmethyl-8-acetamido-imidazo[5,1-c][1,4]benzoxazin-1-one, as claimed in claim 1, and pharmaceutically acceptable salts thereof.

27. 1H,2,3,3a,4-tetrahydro-2-carbamoylmethyl-8-methylsulfonyl-imidazo[5,1-c][1,4]benzoxazin-1-one, as claimed in claim 1, and pharmaceutically acceptable salts thereof.

28. 1H,2,3,3a,4-tetrahydro-2-carbamoylmethyl-8-methylsulfonamido-imidazo[5,1-c][1,4]benzoxazin-1-one, as claimed in claim 1, and pharmaceutically acceptable salts thereof.

29. 1H,2,3,3a,4-tetrahydro-2-(3'-dimethylaminopropyl)-4-phenyl-imidazo[5,1-c][1,4]benzoxazin-1-one, as claimed in claim 1, and pharmaceutically acceptable salts thereof.

30. 1H,2,3,3a,4-tetrahydro-2-carbamoylmethyl-4-phenyl-imidazo[5,1-c][1,4]benzoxazin-1-one, as claimed in claim 1, and pharmaceutically acceptable salts thereof.

31. 1H,2,3,3a,4-tetrahydro-2-(2'-carbamoyl-ethyl)-4-phenyl-imidazo[5,1-c][1,4]benzoxazin-1-one, as claimed in claim 1, and pharmaceutically acceptable salts thereof.

32. 1H,2,3,3a,4-tetrahydro-2-(1'-carbamoyl-ethyl)-4-phenyl-imidazo[5,1-c][1,4]benzoxazin-1-one, as claimed in claim 1, and pharmaceutically acceptable salts thereof.

33. 1H,2,3,3a,4-tetrahydro-2-(1'-methyl-1'-carbamoyl-ethyl)-4-phenyl-imidazo[5,1-c][1,4]benzoxazin-1-one, as claimed in claim 1, and pharmaceutically acceptable salts thereof.

34. 1H,2,3,3a,4-tetrahydro-2-(2'-dimethylaminoethyl)-4-phenyl-imidazo[5,1-c][1,4]benzoxazin-1-one, as claimed in claim 1, and pharmaceutically acceptable salts thereof.

35. 1H,2,3,3a,4-tetrahydro-2-(3'-dimethylaminopropyl)-4-phenyl-8-chloro-imidazo[5,1-c][1,4]benzoxazin-1-one, as claimed in claim 1, and pharmaceutically acceptable salts thereof.

36. 1H,2,3,3a,4-tetrahydro-2-carbamoylmethyl-4-phenyl-8-chloro-imidazo[5,1-c][1,4]benzoxazin-1-one, as claimed in claim 1, and pharmaceutically acceptable salts thereof.

37. 1H,2,3,3a,4-tetrahydro-2-carbamoylmethyl-4-phenyl-8-fluoro-imidazo[5,1-c][1,4]benzoxazin-1-one, as claimed in claim 1, and pharmaceutically acceptable salts thereof.

38. 1H,2,3,3a,4-tetrahydro-2-carbamoylmethyl-4-phenyl-8-hydroxy-imidazo[5,1-c][1,4]benzoxazin-1-one, as claimed in claim 1, and pharmaceutically acceptable salts thereof.

39. 1H,2,3,3a,4-tetrahydro-2-carbamoylmethyl-4-phenyl-8-amino-imidazo[5,1-c][1,4]benzoxazin-1-one, as claimed in claim 1, and pharmaceutically acceptable salts thereof.

40. 1H,2,3,3a,4-tetrahydro-2-carbamoylmethyl-4-phenyl-8-methyl-imidazo[5,1-c][1,4]benzoxazin-1-one, as claimed in claim 1, and pharmaceutically acceptable salts thereof.

41. 1H,2,3,3a,4-tetrahydro-2-carbamoylmethyl-4-phenyl-8-trifluoromethyl-imidazo[5,1-c][1,4]benzoxazin-1-one, as claimed in claim 1, and pharmaceutically acceptable salts thereof.

42. 1H,2,3,3a,4-tetrahydro-2-carbamoylmethyl-4-phenyl-8-methoxy-imidazo[5,1-c][1,4]benzoxazin-1-one, as claimed in claim 1, and pharmaceutically acceptable salts thereof.

43. 1H,2,3,3a,4-tetrahydro-2-carbamoylmethyl-4-phenyl-8-carboxy-imidazo[5,1-c][1,4]benzoxazin-1-one, as claimed in claim 1, and pharmaceutically acceptable salts thereof.

44. 1H,2,3,3a,4,tetrahydro-2-carbamoylmethyl-4-phenyl-8-acetamido-imidazo[5,1-c][1,4]benzoxazin-1-one, as claimed in claim 1, and pharmaceutically acceptable salts thereof.

45. 1H,2,3,3a,4-tetrahydro-2-carbamoylmethyl-4-phenyl-8-methylsulfonyl-imidazo[5,1-c][1,4]benzoxazin-1-one, as claimed in claim 1, and pharmaceutically acceptable salts thereof.

46. 1H,2,3,3a,4-tetrahydro-2-carbamoylmethyl-4-phenyl-8-methylsulfonamido-imidazo[5,1-c][1,4]benzoxazin-1-one, as claimed in claim 1, and pharmaceutically acceptable salts thereof.

47. 1H,2,3,3a,4-tetrahydro-2-carbamoylmethyl-4-(2'-methoxy-phenyl)-imidazo[5,1-c][1,4]benzoxazin-1-one, as claimed in claim 1, and pharmaceutically acceptable salts thereof.

48. 1H,2,3,3a,4-tetrahydro-2-carbamoylmethyl-4-(4'-chlorophenyl)-imidazo[5,1-c][1,4]benzoxazin-1-one, as claimed in claim 1, and pharmaceutically acceptable salts thereof.

49. 1H,2,3,3a,4-tetrahydro-2-methyl-3a-phenyl-imidazo[5,1-c][1,4]benzoxazin-1-one, as claimed in claim 1, and pharmaceutically acceptable salts thereof.

50. 1H,2,3,3a,4-tetrahydro-2-(2'-carbamoyl-ethyl)-3a-phenyl-imidazo[5,1-c][1,4]benzoxazin-1-one, as claimed in claim 1, and pharmaceutically acceptable salts thereof.

51. 1H,2,3,3a,4-tetrahydro-2-(1'-carbamoyl-ethyl)-3a-phenyl-imidazo[5,1-c][1,4]benzoxazin-1-one, as claimed in claim 1, and pharmaceutically acceptable salts thereof.

52. 1H,2,3,3a,4-tetrahydro-2-(1'-methyl-1'-carbamoyl-ethyl)-3a-phenyl-imidazo[5,1-c][1,4]benzoxazin-1-one, as claimed in claim 1, and pharmaceutically acceptable salts thereof.

53. 1H,2,3,3a,4-tetrahydro-2-(2'-dimethylaminoethyl)-3a-phenyl-imidazo[5,1-c][1,4]benzoxazin-1-one, as claimed in claim 1, and pharmaceutically acceptable salts thereof.

54. 1H,2,3,3a,4-tetrahydro-2-(3'-dimethylaminopropyl)-3a-phenyl-imidazo[5,1-c][1,4]benzoxazin-1-one, as claimed in claim 1, and pharmaceutically acceptable salts thereof.

55. 1H,2,3,3a,4-tetrahydro-2-carbamoylmethyl-3a-phenyl-8-chloro-imidazo[5,1-c][1,4]benzoxazin-1-one, as claimed in claim 1, and pharmaceutically acceptable salts thereof.

56. 1H,2,3,3a,4-tetrahydro-2-carbamoylmethyl-3a-phenyl-8-fluoro-imidazo[5,1-c][1,4]benzoxazin-1-one, as claimed in claim 1, and pharmaceutically acceptable salts thereof.

57. 1H,2,3,3a,4-tetrahydro-2-carbamoylmethyl-3a-phenyl-8-hydroxy-imidazo[5,1-c][1,4]benzoxazin-1-one, as claimed in claim 1, and pharmaceutically acceptable salts thereof.

58. 1H,2,3,3a,4-tetrahydro-2-carbamoylmethyl-3a-phenyl-8-amino-imidazo[5,1-c][1,4]benzoxazin-1-one, as claimed in claim 1, and pharmaceutically acceptable salts thereof.

59. 1H,2,3,3a,4-tetrahydro-2-carbamoylmethyl-3a-phenyl-8-methyl-imidazo[5,1-c][1,4]benzoxazin-1-one, as claimed in claim 1, and pharmaceutically acceptable salts thereof.

60. 1H,2,3,3a,4-tetrahydro-2-carbamoylmethyl-3a-phenyl-8-trifluoromethyl-imidazo[5,1-c][1,4]benzoxazin-1-one, as claimed in claim 1, and pharmaceutically acceptable salts thereof.

61. 1H,2,3,3a,4-tetrahydro-2-carbamoylmethyl-3a-phenyl-8-methoxy-imidazo[5,1-c][1,4]benzoxazin-1-one, as claimed in claim 1, and pharmaceutically acceptable salts thereof.

62. 1H,2,3,3a,4-tetrahydro-2-carbamoylmethyl-3a-phenyl-8-carboxy-imidazo[5,1-c][1,4]benzoxazin-1-one, as claimed in claim 1, and pharmaceutically acceptable salts thereof.

63. 1H,2,3,3a,4-tetrahydro-2-carbamoylmethyl-3a-phenyl-8-acetamido-imidazo[5,1-c][1,4]benzoxazin-1-one, as claimed in claim 1, and pharmaceutically acceptable salts thereof.

64. 1H,2,3,3a,4-tetrahydro-2-carbamoylmethyl-3a-phenyl-8-methylsulfonyl-imidazo[5,1-c][1,4]benzoxazin-1-one, as claimed in claim 1, and pharmaceutically acceptable salts thereof.

65. 1H,2,3,3a,4-tetrahydro-2-carbamoylmethyl-3a-phenyl-8-methylsulfonamido-imidazo[5,1-c][1,4]benzoxazin-1-one, as claimed in claim 1, and pharmaceutically acceptable salts thereof.

* * * * *